(12) United States Patent
Simpson et al.

(10) Patent No.: US 7,657,297 B2
(45) Date of Patent: Feb. 2, 2010

(54) IMPLANTABLE ANALYTE SENSOR

(75) Inventors: Peter C. Simpson, Del Mar, CA (US);
Mark Shults, Madison, WI (US);
Rathbun K. Rhodes, Madison, WI (US);
Paul V. Goode, Jr., Murrieta, CA (US);
Arnold L. Holmquist, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 910 days.

(21) Appl. No.: 10/838,909

(22) Filed: May 3, 2004

(65) Prior Publication Data

US 2005/0245795 A1 Nov. 3, 2005

(51) Int. Cl.
*A61B 5/05* (2006.01)
*A61B 5/00* (2006.01)
*G01N 27/26* (2006.01)

(52) U.S. Cl. ............... 600/347; 600/345; 600/365; 204/403.01; 204/412

(58) Field of Classification Search ......... 600/345–366, 600/309; 435/283.1, 287.1; 204/193, 400, 204/403.01, 403.1, 403.11, 412

See application file for complete search history.

(56) References Cited

U.S. PATENT DOCUMENTS

| | | | |
|---|---|---|---|
| 3,219,533 A | 11/1965 | Mullins | |
| 3,775,182 A | 11/1973 | Patton et al. | |
| 3,979,274 A | 9/1976 | Newman | |
| 4,197,840 A | 4/1980 | Beck et al. | |
| 4,225,410 A | 9/1980 | Pace | |
| 4,240,889 A | 12/1980 | Yoda et al. | |
| 4,255,500 A | 3/1981 | Hooke | |
| 4,324,257 A | 4/1982 | Albarda et al. | |
| 4,374,013 A | 2/1983 | Enfors | |
| 4,418,148 A | 11/1983 | Oberhardt | |
| 4,431,507 A | 2/1984 | Nankai et al. | |

(Continued)

FOREIGN PATENT DOCUMENTS

EP 0 127 958 12/1984

(Continued)

OTHER PUBLICATIONS

Beach, et al. 1999. Subminiature implantable potentiostat and modified commercial telemetry device for remote glucose monitoring. *IEEE Transactions on Instrumentation and Measurement*, 48(6):1239-1245.

(Continued)

*Primary Examiner*—Charles A Marmor, II
*Assistant Examiner*—Navin Natnithithadha
(74) *Attorney, Agent, or Firm*—Knobbe Martens Olson & Bear LLP

(57) ABSTRACT

An implantable analyte sensor including a sensing region for measuring the analyte and a non-sensing region for immobilizing the sensor body in the host. The sensor is implanted in a precisely dimensioned pocket to stabilize the analyte sensor in vivo and enable measurement of the concentration of the analyte in the host before and after formation of a foreign body capsule around the sensor. The sensor further provides a transmitter for RF transmission through the sensor body, electronic circuitry, and a power source optimized for long-term use in the miniaturized sensor body.

28 Claims, 20 Drawing Sheets

U.S. PATENT DOCUMENTS

| | | | |
|---|---|---|---|
| 4,477,314 A * | 10/1984 | Richter et al. | 205/782.5 |
| RE31,916 E * | 6/1985 | Oswin et al. | 204/412 |
| RE32,361 E | 2/1987 | Duggan | |
| 4,663,824 A | 5/1987 | Kenmochi | |
| 4,721,677 A | 1/1988 | Clark, Jr. | |
| 4,750,496 A | 6/1988 | Reinhart et al. | |
| 4,805,624 A * | 2/1989 | Yao et al. | 600/345 |
| 4,871,440 A | 10/1989 | Nagata et al. | |
| 4,883,057 A * | 11/1989 | Broderick | 600/302 |
| 4,927,407 A | 5/1990 | Dorman | |
| 4,927,516 A | 5/1990 | Yamaguchi et al. | |
| 4,953,552 A | 9/1990 | DeMarzo | |
| 4,974,929 A | 12/1990 | Curry | |
| 5,034,112 A | 7/1991 | Murase et al. | |
| 5,130,231 A | 7/1992 | Kennedy et al. | |
| 5,171,689 A | 12/1992 | Kawaguri et al. | |
| 5,190,041 A | 3/1993 | Palti | |
| 5,222,980 A | 6/1993 | Gealow | |
| 5,249,576 A | 10/1993 | Goldberger et al. | |
| 5,282,848 A | 2/1994 | Schmitt | |
| 5,312,361 A | 5/1994 | Zadini et al. | |
| 5,322,063 A | 6/1994 | Allen et al. | |
| 5,337,747 A | 8/1994 | Neftel | |
| 5,352,351 A | 10/1994 | White | |
| 5,368,028 A | 11/1994 | Palti | |
| 5,372,133 A | 12/1994 | Hogen Esch | |
| 5,384,028 A | 1/1995 | Ito | |
| 5,411,647 A | 5/1995 | Johnson et al. | |
| 5,431,160 A | 7/1995 | Wilkins | |
| 5,458,631 A | 10/1995 | Xavier et al. | |
| 5,462,645 A | 10/1995 | Albery et al. | |
| 5,466,356 A | 11/1995 | Schneider et al. | |
| 5,469,846 A | 11/1995 | Khan | |
| 5,482,473 A | 1/1996 | Lord et al. | |
| 5,529,066 A | 6/1996 | Palti | |
| 5,564,439 A | 10/1996 | Picha | |
| 5,569,186 A | 10/1996 | Lord et al. | |
| 5,569,462 A | 10/1996 | Martinson et al. | |
| 5,571,395 A | 11/1996 | Park et al. | |
| 5,575,930 A | 11/1996 | Tietje-Girault et al. | |
| 5,589,133 A * | 12/1996 | Suzuki | 422/79 |
| 5,607,565 A | 3/1997 | Azarnia et al. | |
| 5,611,900 A | 3/1997 | Worden | |
| 5,628,890 A | 5/1997 | Carter et al. | |
| 5,640,954 A | 6/1997 | Pfeiffer | |
| 5,686,829 A | 11/1997 | Girault | |
| 5,704,354 A | 1/1998 | Preidel et al. | |
| 5,706,807 A | 1/1998 | Picha | |
| 5,711,861 A | 1/1998 | Ward et al. | |
| 5,741,330 A | 4/1998 | Brauker et al. | |
| 5,749,907 A | 5/1998 | Mann | |
| 5,787,900 A | 8/1998 | Butler et al. | |
| 5,791,344 A | 8/1998 | Schulman et al. | |
| 5,800,420 A * | 9/1998 | Gross et al. | 604/890.1 |
| 5,807,375 A * | 9/1998 | Gross et al. | 604/890.1 |
| 5,814,599 A | 9/1998 | Mitragotri et al. | |
| 5,820,622 A * | 10/1998 | Gross et al. | 604/890.1 |
| 5,833,603 A | 11/1998 | Kovacs et al. | |
| 5,837,728 A | 11/1998 | Purcell | |
| 5,861,019 A | 1/1999 | Sun et al. | |
| 5,871,514 A | 2/1999 | Wiklund et al. | |
| 5,897,578 A | 4/1999 | Wiklund et al. | |
| 5,913,998 A | 6/1999 | Butler et al. | |
| 5,917,346 A | 6/1999 | Gord | |
| 5,919,215 A | 7/1999 | Wiklund et al. | |
| 5,944,661 A * | 8/1999 | Swette et al. | 600/345 |
| 5,964,261 A | 10/1999 | Neuenfeldt et al. | |
| 5,964,993 A | 10/1999 | Blubaugh et al. | |
| 5,985,129 A | 11/1999 | Gough et al. | |
| 5,989,409 A | 11/1999 | Kurnik et al. | |
| 5,999,848 A | 12/1999 | Gord et al. | |
| 6,001,067 A | 12/1999 | Shults et al. | |
| 6,011,984 A | 1/2000 | Van Antwerp et al. | |
| 6,013,113 A | 1/2000 | Mika | |
| 6,016,448 A | 1/2000 | Busacker et al. | |
| 6,049,727 A | 4/2000 | Crothall | |
| 6,066,083 A | 5/2000 | Slater et al. | |
| 6,066,448 A | 5/2000 | Wohlstadter et al. | |
| 6,081,736 A | 6/2000 | Colvin et al. | |
| 6,088,608 A | 7/2000 | Schulman et al. | |
| 6,107,083 A | 8/2000 | Collins et al. | |
| 6,115,634 A | 9/2000 | Donders et al. | |
| 6,117,290 A | 9/2000 | Say | |
| 6,119,028 A | 9/2000 | Schulman et al. | |
| 6,122,536 A | 9/2000 | Sun et al. | |
| 6,167,614 B1 | 1/2001 | Tuttle et al. | |
| 6,175,752 B1 | 1/2001 | Say et al. | |
| 6,201,980 B1 | 3/2001 | Darrow et al. | |
| 6,201,993 B1 | 3/2001 | Kruse et al. | |
| 6,208,894 B1 | 3/2001 | Schulman et al. | |
| 6,212,416 B1 | 4/2001 | Ward et al. | |
| 6,214,185 B1 | 4/2001 | Offenbacher et al. | |
| 6,233,080 B1 | 5/2001 | Brenner et al. | |
| 6,233,471 B1 | 5/2001 | Berner et al. | |
| 6,248,067 B1 | 6/2001 | Causey, III et al. | |
| 6,256,522 B1 | 7/2001 | Schultz | |
| 6,259,937 B1 | 7/2001 | Schulman et al. | |
| 6,264,825 B1 | 7/2001 | Blackburn et al. | |
| 6,275,717 B1 * | 8/2001 | Gross et al. | 600/345 |
| 6,284,478 B1 | 9/2001 | Heller et al. | |
| 6,285,897 B1 | 9/2001 | Kilcoyne et al. | |
| 6,300,002 B1 | 10/2001 | Webb et al. | |
| 6,309,526 B1 | 10/2001 | Fujiwara et al. | |
| 6,325,979 B1 | 12/2001 | Hahn et al. | |
| 6,329,161 B1 | 12/2001 | Heller et al. | |
| 6,329,929 B1 | 12/2001 | Weijand et al. | |
| 6,330,464 B1 | 12/2001 | Colvin, Jr. et al. | |
| 6,360,888 B1 | 3/2002 | MeIver et al. | |
| 6,366,794 B1 * | 4/2002 | Moussy et al. | 600/345 |
| 6,368,274 B1 | 4/2002 | Van Antwerp et al. | |
| 6,372,244 B1 | 4/2002 | Antanavich et al. | |
| 6,400,974 B1 | 6/2002 | Lesho | |
| 6,406,066 B1 | 6/2002 | Uegane | |
| 6,409,674 B1 | 6/2002 | Brockway et al. | |
| 6,424,847 B1 | 7/2002 | Mastrototaro et al. | |
| 6,442,413 B1 | 8/2002 | Silver | |
| 6,447,448 B1 | 9/2002 | Ishikawa et al. | |
| 6,447,542 B1 | 9/2002 | Weadock | |
| 6,454,710 B1 | 9/2002 | Ballerstadt et al. | |
| 6,466,810 B1 | 10/2002 | Ward et al. | |
| 6,477,395 B2 | 11/2002 | Schulman et al. | |
| 6,484,046 B1 | 11/2002 | Say et al. | |
| 6,498,043 B1 | 12/2002 | Schulman et al. | |
| 6,512,939 B1 | 1/2003 | Colvin et al. | |
| 6,541,107 B1 | 4/2003 | Zhong et al. | |
| 6,544,212 B2 | 4/2003 | Galley et al. | |
| 6,546,268 B1 | 4/2003 | Ishikawa et al. | |
| 6,547,839 B2 | 4/2003 | Zhang et al. | |
| 6,558,320 B1 | 5/2003 | Causey | |
| 6,579,498 B1 | 6/2003 | Eglise | |
| 6,585,763 B1 | 7/2003 | Keilman et al. | |
| 6,587,705 B1 | 7/2003 | Kim et al. | |
| 6,589,229 B1 | 7/2003 | Connelly et al. | |
| 6,591,125 B1 * | 7/2003 | Buse et al. | 600/347 |
| 6,605,072 B2 | 8/2003 | Struys et al. | |
| 6,618,934 B1 * | 9/2003 | Feldman et al. | 29/830 |
| 6,654,625 B1 | 11/2003 | Say et al. | |
| 6,673,596 B1 | 1/2004 | Sayler et al. | |
| 6,699,383 B2 | 3/2004 | Lemire et al. | |
| 6,702,857 B2 | 3/2004 | Brauker et al. | |
| 6,721,587 B2 | 4/2004 | Gough | |
| 6,731,976 B2 | 5/2004 | Penn et al. | |
| 6,741,877 B1 | 5/2004 | Shults et al. | |
| 6,773,565 B2 | 8/2004 | Kunimoto et al. | |

| | | |
|---|---|---|
| 6,793,632 B2 | 9/2004 | Sohrab |
| 6,793,802 B2 | 9/2004 | Lee et al. |
| 6,802,957 B2 | 10/2004 | Jung et al. |
| 6,809,507 B2 | 10/2004 | Morgan et al. |
| 6,809,653 B1 | 10/2004 | Mann et al. |
| 6,862,465 B2 | 3/2005 | Shults et al. |
| 6,893,552 B1 | 5/2005 | Wang et al. |
| 6,952,604 B2 * | 10/2005 | DeNuzzio et al. ............ 600/345 |
| 7,025,743 B2 | 4/2006 | Mann et al. |
| 7,058,437 B2 * | 6/2006 | Buse et al. ................. 600/347 |
| 7,074,307 B2 | 7/2006 | Simpson et al. |
| 7,081,195 B2 * | 7/2006 | Simpson et al. .......... 205/777.5 |
| 7,108,778 B2 | 9/2006 | Simpson et al. |
| 7,166,074 B2 | 1/2007 | Reghabit et al. |
| 7,169,289 B2 * | 1/2007 | Schulein et al. .......... 205/777.5 |
| 7,225,535 B2 * | 6/2007 | Feldman et al. ................ 29/831 |
| 7,426,408 B2 * | 9/2008 | DeNuzzio et al. ............ 600/345 |
| 2002/0042561 A1 | 4/2002 | Schulman et al. |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0065254 A1 | 4/2003 | Schulman et al. |
| 2003/0070548 A1 | 4/2003 | Clausen |
| 2003/0078560 A1 | 4/2003 | Miller et al. |
| 2003/0125613 A1 | 7/2003 | Enegren et al. |
| 2003/0130616 A1 | 7/2003 | Steil et al. |
| 2003/0187338 A1 | 10/2003 | Say et al. |
| 2003/0211625 A1 | 11/2003 | Cohan |
| 2004/0011671 A1 | 1/2004 | Shults et al. |
| 2004/0015063 A1 * | 1/2004 | DeNuzzio et al. ............ 600/347 |
| 2004/0045879 A1 | 3/2004 | Shults et al. |
| 2004/0074785 A1 | 4/2004 | Holker |
| 2004/0078219 A1 | 4/2004 | Kaylor |
| 2004/0106857 A1 | 6/2004 | Gough |
| 2004/0167801 A1 | 8/2004 | Say et al. |
| 2004/0186362 A1 | 9/2004 | Brauker et al. |
| 2004/0199059 A1 | 10/2004 | Brauker et al. |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 * | 5/2005 | DeNuzzio et al. ............ 600/345 |
| 2005/0112169 A1 | 5/2005 | Brauker et al. |
| 2005/0154271 A1 | 7/2005 | Rasdal et al. |
| 2005/0192557 A1 | 9/2005 | Brauker et al. |
| 2005/0211571 A1 * | 9/2005 | Schulein et al. .......... 205/777.5 |
| 2005/0242479 A1 | 11/2005 | Petisce et al. |
| 2005/0245799 A1 | 11/2005 | Brauker et al. |
| 2006/0015020 A1 | 1/2006 | Neale et al. |
| 2006/0200022 A1 | 9/2006 | Brauker et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2007/0032718 A1 | 2/2007 | Shults et al. |

FOREIGN PATENT DOCUMENTS

| | | |
|---|---|---|
| EP | 0 353 328 | 2/1990 |
| EP | 0 396 788 | 11/1990 |
| EP | 0 534 074 | 3/1993 |
| EP | 0 539 625 | 5/1993 |
| EP | 0 967 788 | 12/1999 |
| FR | 2656423 | 6/1991 |
| FR | 2760962 | 9/1998 |
| JP | 62083649 | 4/1987 |
| JP | 2002-189015 | 7/2002 |
| WO | WO 92/07525 | 5/1992 |
| WO | WO 92/13271 | 8/1992 |
| WO | WO 94/22367 | 10/1994 |
| WO | WO 95/07109 | 3/1995 |
| WO | WO 97/43633 | 11/1997 |
| WO | WO 98/24358 | 6/1998 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 01/12158 | 2/2001 |
| WO | WO 01/34243 A1 | 5/2001 |
| WO | WO 01/43660 | 6/2001 |

OTHER PUBLICATIONS

Bowman, L.; Meindl, J. D. The packaging of implantable integrated sensors. IEEE Trans Biomed Eng 1986, 33, 248-255.

Cai, Q.; Zeng, K.; Ruan, C.; Desai, T. A.; Grimes, C. A. A wireless, remote query glucose biosensor based on a pH-sensitive polymer. Anal Chem 2004, 76, 4038-4043.

D'Arrigo, et al. Poro -Si based bioreactors for glucose monitoring and drugs production. Proc. of SPIE 2003, 4982, 178-184.

El-Sa'ad, L.; Yates, D. Moisture Absorption by Epoxy Resins: the Reverse Thermal Effect. Journal of Materials Science 1990, 25, 3577-3582.

Garg, S.; Schwartz, S.; Edelman, S. Improved Glucose Excursions Using an Implantable Real-Time Continuous Glucose Sensor in Adults with Type I Diabetes. Diabetes Care 2004, 27, 734-738.

Gilligan, et al. 1994. Evaluation of a subcutaneous glucose sensor out to 3 months in a dog model. *Diabetes Care*, 17(8):882-887.

Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.

Heise, et al. 2003. Hypoglycemia warning signal and glucose sensors: Requirements and concepts. *Diabetes Technology & Therapeutics*, 5:563-571.

Heller, A. Implanted electrochemical glucose sensors for the management of diabetes. Annu Rev Biomed Eng 1999, 1, 153-175.

Kraver, K.; Gutha , M. R.; Strong, T.; Bird, P.; Cha, G.; Hoeld, W.; Brown, R. A mixed-signal sensor interface microinstrument. Sensors and Actuators A: Physical 2001, 91, 266-277.

Rhodes, et al. 1994. Prediction of pocket-portable and implantable glucose enzyme electrode performance from combined species permeability and digital simulation analysis. *Analytical Chemistry*, 66, (9) 1520-1529.

Sansen, et al. 1990. A smart sensor for the voltammetric measurement of oxygen or glucose concentrations. *Sensors and Actuators*, B 1:298-302.

Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.

Tierney, M. J.; Garg, S.; Ackerman, N. R.; Fermi, S. J.; Kennedy, J.; Lopatin, M.; Potts, R. O.; Tamada, J. A. Effect of acetaminophen on the accuracy of glucose measurements obtained with the GlucoWatch biographer. Diabetes Technol Ther 2000, 2, 199-207.

Updike et al. 1994. Improved long-term performance in vitro and in vivo. *ASAIO Journal*, 40(2):157-163.

Updike et al. 1997. Principles of long-term fully implanted sensors with emphasis on radiotelemetric monitoring of blood glucose from inside a subcutaneous foreign body capsule (FBC). In Fraser, D. M. (Ed.). Biosensors in the Body: Continuous in vivo Monitoring. Chap. 4, pp. 117-137, Hoboken, NJ: John Wiley.

Updike, et al. 2000. A subcutaneous glucose sensor with improved longevity, dynamic range, and stability of calibration. *Diabetes Care*, 23(2):208-214.

Valdes, et al. 2000. In vitro and in vivo degradation of glucose oxidase enzyme used for an implantable glucose biosensor. *Diabetes Technol. Ther.*, 2:367-376.

Wagner, et al. 1998. Continuous amperometric monitoring of glucose in a brittle diabetic chimpanzee with a miniature subcutaneous electrode. *Proc. Natl. Acad. Sci. A*, 95:6379-6382.

Ward, et al. 1999. Assessment of chronically implanted subcutaneous glucose sensors in dogs: The effect of surrounding fluid masses. *ASAIO Journal*, 45:555-561.

Ward, W. K.; Wood, M. D.; Troupe, J. E. Understanding Spontaneous Output Fluctuations of an Amperometric Glucose Sensor: Effect of Inhalation Anesthesia and Use of a Nonenzyme Containing Electrode. ASAIO Journal 2000, 540-546.

Ward, et al. 2000. Rise in background current over time in a subcutaneous glucose sensor in the rabbit: Relevance to calibration and accuracy. *Biosensors & Bioelectronics*, 15:53-61.

Ward et al. 2002. A new amperometric glucose microsensor: In vitro and short-term in vivo evaluation. *Biosensors & Bioelectronics*, 17:181-189.

Wilkins, et al. 1995. Integrated implantable device for long-term glucose monitoring. *Biosens. Bioelectron.*, 10:485-494.

Wientjes, K. J. C. Development of a glucose sensor for diabetic patients. 2000.

Wilkins, E.; Atanasov, P. Glucose monitoring: state of the art and future possibilities. Med Eng Phys 1995, 18, 273-288.

Wilson, et al. 1992. Progress toward the development of an implantable sensor for glucose. *Clin. Chem.*, 38(9):1613-1617.

Wood, W., et al., Hermetic Sealing with Epoxy. Mechanical Engineering Mar. 1990, 1-3.

U.S. Appl. No. 09/447,227, filed Nov. 22, 1999.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/885,476, filed Jul. 6, 2004.
U.S. Appl. No. 10/896,312, filed Jul. 21, 2004.

Answers.com. "xenogenic." The American Heritage Stedman's Medical Dictionary. Houghton Mifflin Company, 2002. Answers.com Nov. 7, 2006 http://www.Answers.com/topic/xenogenic.

Bard et al. 1980. Electrochemical Methods. John Wiley & Sons, pp. 173-175.

Boll, A. W. 1997. A Comparison of Cyclic Voltammetry and Cyclic Staircase Voltammetry Current Separations 16:1, 23-26.

Brauker, et al. 1995. Neovascularization of synthetic membranes directed by membrane Microarchitecture. J. Biomed Mater Res 29:1517-1524.

Brooks, et al. "Development of an on-line glucose sensor for fermentation monitoring," Biosensors, 3:45-56 (1987/88).

Cass, et al. "Ferrocene-mediated enzyme electrodes for amperometric determination of glucose," Anal. Chem., 36:667-71 (1984).

Frohnauer, et al. 2001. Graphical human insulin time-activity profiles using standardized definitions. Diabetes Technology & Therapeutics 3(3):419-429.

Heller, "Electrical wiring of redox enzymes," Acc. Chem. Res., 23:128-134 (1990).

Loffler, et al. 1995. Separation and determination of traces of ammonia in air by means of chromatomembrane cells. Fresenius J Anal Chem 352:613-614.

Moatti-Sirat, D, et al. 1992. Evaluating in vitro and in vivo the interference of ascorbate and acetaminophen on glucose detection by a needle-type glucose sensor. Biosensors and Bioelectronics 7:345-352.

Pickup, et al. "Implantable glucose sensors: choosing the appropriate sensor strategy," Biosensors, 3:335-346 (1987/88).

Pineda, et al. 1996. Bone regeneration with resorbable polymeric membranes. III. Effect of poly(L-lactide) membrane pore size on the bone healing process in large defects. J. Biomedical Materials Research 31:385-394.

Rebrin, et al. "Automated feedback control of subcutaneous glucose concentration in diabetic dogs," Diabetologia, 32:573-76 (1989).

Sieminski, et al. 2000. Biomaterial-microvasculature interactions. Biomaterials 21:2233-2241.

Turner and Pickup, "Diabetes mellitus: biosensors for research and management," Biosensors, 1:85-115 (1985).

Office Action dated Apr. 9, 2003 in U.S. Appl. No. 09/916,386.
Office Action dated Sep. 5, 2006 in U.S. Appl. No. 09/916,711.
Office Action dated Feb. 14, 2006 in U.S. Appl. No. 09/916,711.
Office Action dated Jul. 1, 2005 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Feb. 11, 2004 in U.S. Appl. No. 09/916,711.
Office Action dated Sep. 24, 2003 in U.S. Appl. No. 09/916,711.
Office Action dated Dec. 7, 1998 in U.S. Appl. No. 08/811,473.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Aug. 14, 2001 in U.S. Appl. No. 09/489,588.
Office Action dated Feb. 27, 2002 in U.S. Appl. No. 09/489,588.
Office Action dated Jun. 12, 2003 in U.S. Appl. No. 09/489,588.
Office Action dated Sep. 21, 2004 in U.S. Appl. No. 10/657,843.
Office Action dated Sep. 30, 2002 in U.S. Appl. No. 09/633,369.
Office Action dated Sep. 21, 2004 in U.S. Appl. No. 09/916,858.
Office Action dated Mar. 22, 2004 in U.S. Appl. No. 09/916,858.
Office Action dated Aug. 14, 2006 in U.S. Appl. No. 11/039,269.
Office Action datd Feb. 24, 2006 in U.S. Appl. No. 11/039,269.
Office Action dated Nov. 2, 2005 in U.S. Appl. No. 11/039,269.
Office Action dated May 4, 2005 in U.S. Appl. No. 11/039,269.
Office Action dated Feb. 24, 2006 in U.S. Appl. No. 10/646,333.
Office Action dated Jun. 6, 2003 in U.S. Appl. No. 10/646,333.
Office Action dated Sep. 22, 2004 in U.S. Appl. No. 10/646,333.
Office Action dated Oct. 16, 2006 in U.S. Appl. No. 10/647,065.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated May 11, 2006 in U.S. Appl. No. 10/897,377.
Office Action dated Oct. 18, 2005 in U.S. Appl. No. 10/897,377.
Office Action dated Feb. 9, 2006 in U.S. Appl. No. 10/897,312.
Office Action dated Jan. 27, 2006 in U.S. Appl. No. 11/007,635.
Office Action dated May 23, 2007 in U.S. Appl. No. 11/055,779.
Office Action dated Nov. 27, 2006 in U.S. Appl. No. 10/789,359.
Office Action dated Sep. 21, 2007 in U.S. Appl. No. 10/838,912.
Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Sep. 25, 2007 in U.S. Appl. No. 11/334,876.
IPRP for PCT/US05/014696 filed May 2, 2005.

* cited by examiner

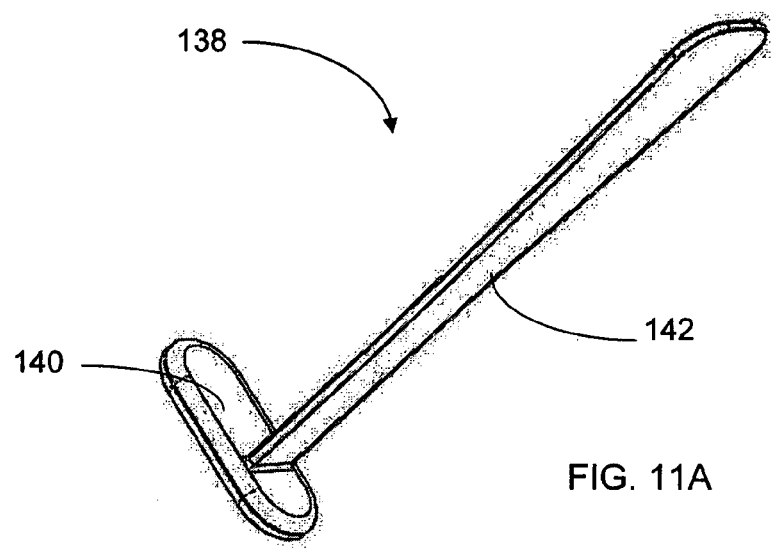
FIG. 11A
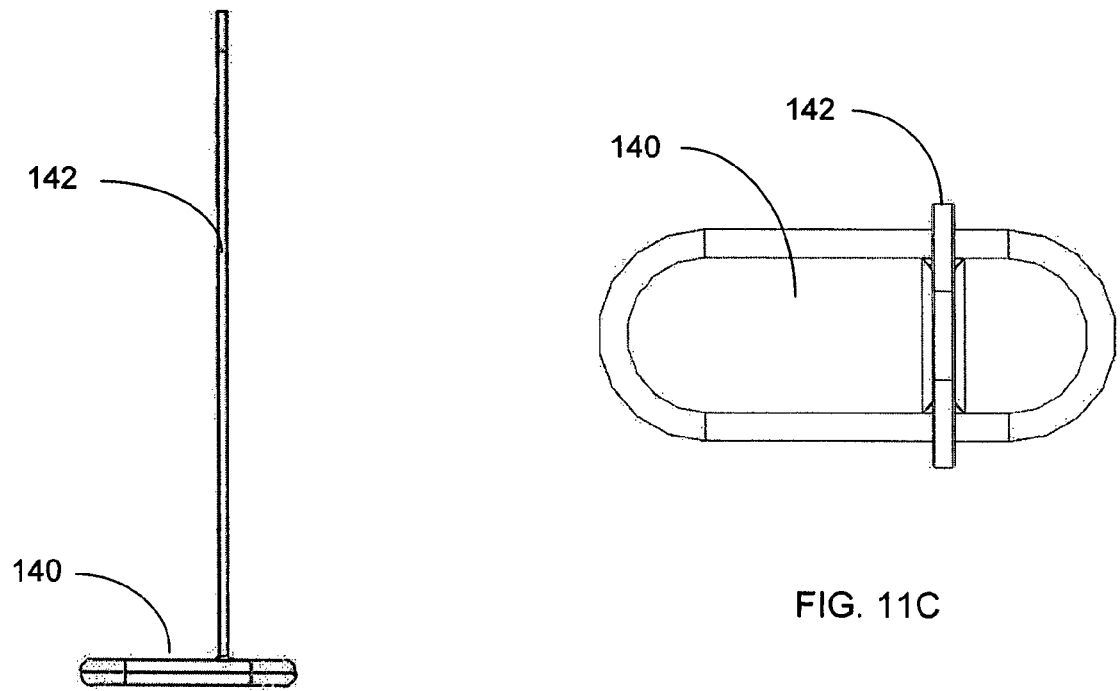
FIG. 11B
FIG. 11C

IMPLANTABLE ANALYTE SENSOR

FIELD OF THE INVENTION

The present invention relates generally to systems and methods for making and using an implantable analyte sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

The prior art discloses a variety of analyte sensors that provide complex, short-term, transcutaneous, or partially implantable analyte sensors. Unfortunately, each of these sensors suffers from various disadvantages, such as lack of continuous care (short-term sensors), discomfort (transcutaneous and partially implantable sensors), and inconvenience (sensors with multiple components).

SUMMARY OF THE INVENTION

There is a need for a device a long-term, implantable analyte sensor that functions accurately and reliably, to provide improved patient convenience and care.

Accordingly, in a first embodiment, an implantable analyte sensor for measuring an analyte in a host is provided, the sensor including: a sensor body including a sensing region for measuring the analyte and a non-sensing region for immobilizing the sensor body in the host; a first biointerface material adjacent to the sensing region, wherein the first biointerface material includes a porous architecture that promotes vascularized tissue ingrowth and interferes with barrier cell layer formation, for allowing analyte transport to the sensing region in vivo; and a second biointerface material adjacent to at least a portion of the non-sensing region, wherein the second biointerface material includes a porous architecture that promotes tissue ingrowth for anchoring the sensor in vivo.

In an aspect of the first embodiment, the first biointerface material further includes a domain proximal to the sensing region that is impermeable to cells or cell processes and is permeable to the passage of the analyte.

In an aspect of the first embodiment, the second biointerface material and the first biointerface material include porous silicone, and wherein first biomaterial material includes porous silicone with a through porosity substantially across the entire material.

In an aspect of the first embodiment, the sensing region is on a first surface of the sensor body, and wherein the sensor body includes a second surface opposite the first surfaces, and wherein the second biointerface material is disposed on a substantial portion of the first and second surfaces of the sensor body.

In a second embodiment, an analyte sensor for short-term and long-term immobilization in a host's soft tissue is provided, the sensor including: a short-term anchoring mechanism for providing immobilization of the sensor in the soft tissue prior to substantial formation of the foreign body capsule; and a long-term anchoring mechanism for providing immobilization of the sensor in the soft tissue during and after substantial formation of the foreign body capsule.

In an aspect of the second embodiment, the short-term anchoring mechanism includes a suture tab on the sensor body. In an aspect of the second embodiment, the short-term anchoring mechanism includes a suture. In an aspect of the second embodiment, the short-term anchoring mechanism includes at least one of prongs, spines, barbs, wings, and hooks. In an aspect of the second embodiment, the short-term anchoring mechanism includes a geometric configuration of the sensor body. In an aspect of the second embodiment, the geometric configuration includes at least one of a helical, tapered, and winged configuration.

In an aspect of the second embodiment, the long-term anchoring mechanism includes an anchoring material disposed on the sensor body. In an aspect of the second embodiment, the anchoring material includes a fibrous material. In an aspect of the second embodiment, the anchoring material includes a porous material. In an aspect of the second embodiment, the anchoring material includes a material with a surface topography. In an aspect of the second embodiment, the long-term anchoring mechanism includes a surface topography formed on an outer surface of the sensor body.

In a third embodiment, a method for immobilizing an analyte sensor in soft tissue is provided, the method including: implanting the analyte sensor in a host; anchoring the sensor in the host prior to formation of a foreign body capsule for at least short-term immobilization of the sensor within the soft tissue of the host; and anchoring the sensor within the foreign body capsule for long-term immobilization of the sensor within the soft tissue of the host.

In an aspect of the third embodiment, the short-term immobilization step includes suturing the sensor to the host's tissue. In an aspect of the third embodiment, the suturing step includes suturing the sensor such that the sensor is in compression. In an aspect of the third embodiment, the short term immobilization step includes utilizing at least one of prongs, spines, barbs, wings, and hooks on the sensor to anchor the sensor into the host's tissue upon implantation.

In an aspect of the third embodiment, the long-term immobilization step includes disposing an anchoring material on the sensor body that allows host tissue ingrowth into the material. In an aspect of the third embodiment, the anchoring material includes a fibrous material. In an aspect of the third embodiment, the anchoring material includes a porous material. In an aspect of the third embodiment, the anchoring material includes a material with a surface topography. In an aspect of the third embodiment, the long-term immobilization step includes utilizing a surface topography formed on an outer surface of the sensor body that allows tissue ingrowth into the surface of the sensor body.

In a fourth embodiment, a method for continuous measurement of an analyte in a host is provided, the method including: implanting an analyte sensor in a host; and measuring the concentration of the analyte in the host before and after formation of a foreign body capsule around the sensor.

In an aspect of the fourth embodiment, the analyte sensor is wholly implanted into the host. In an aspect of the fourth embodiment, the method further includes explanting the analyte sensor from the host. In an aspect of the fourth embodiment, the method further includes implanting another analyte sensor in the host. In an aspect of the fourth embodiment, the another analyte sensor is wholly implanted into the host.

In an aspect of the fourth embodiment, the method further includes anchoring the analyte sensor in the host prior to formation of a foreign body capsule for at least short-term immobilization of the sensor within the soft tissue of the host. In an aspect of the fourth embodiment, the method further includes anchoring the sensor within the foreign body capsule for long-term immobilization of the sensor within the soft tissue of the host.

In a fifth embodiment, a method for implantation of an analyte sensor in a host is provided, the method including: forming a precisely dimensioned pocket in the subcutaneous space of the host, wherein the pocket is dimensioned no greater than the dimensions of the analyte sensor; inserting the analyte sensor into the precisely-dimensioned pocket so as to minimize movement of the sensor within the pocket.

In an aspect of the fifth embodiment, the step of forming a pocket includes using a tool that allows precise dimensioning of the pocket. In an aspect of the fifth embodiment, the tool includes a head dimensioned substantially similar to the dimensions of the analyte sensor and a handle for guiding the head into the pocket. In an aspect of the fifth embodiment, the tool includes a head dimensioned smaller than the dimensions of the analyte sensor and a handle for guiding the head into the pocket.

In an aspect of the fifth embodiment, the method further includes suturing the analyte sensor to the host tissue.

In an aspect of the fifth embodiment, the pocket is formed adjacent the fascia of the host. In an aspect of the fifth embodiment, the analyte sensor includes a sensing region for measuring an analyte concentration, and wherein the analyte sensor is placed within the pocket such that the sensing region is located adjacent to the fascia.

In an aspect of the fifth embodiment, the method further includes a step of forming a vertical incision prior to the step of forming a pocket. In an aspect of the fifth embodiment, the method further includes a step of forming a horizontal incision prior to the step of forming a pocket. In an aspect of the fifth embodiment, the pocket is formed in the abdominal region of the host.

In a sixth embodiment, an implantable analyte sensor for measuring an analyte concentration in a host is provided, the sensor including: a sensor body substantially formed from a water vapor permeable material; and electrical components encapsulated within the sensor body, wherein the electrical components include RF circuitry and an antenna adapted for RF transmission from the sensor in vivo to a receiver ex vivo, wherein the RF circuitry is spaced a fixed distance from the sensor body so as to support a dielectric constant that enables RF transmission between the sensor in vivo to the receiver ex vivo.

In an aspect of the sixth embodiment, the fixed distance includes a configuration that reduces water permeability therein. In an aspect of the sixth embodiment, the configuration includes conformal coating. In an aspect of the sixth embodiment, the conformal coating includes Parylene.

In an aspect of the sixth embodiment, the configuration includes epoxy. In an aspect of the sixth embodiment, the configuration includes glass. In an aspect of the sixth embodiment, the configuration includes one or more hermetic containers.

In a seventh embodiment, an analyte sensor for RF transmission between the analyte sensor in vivo and a receiver ex vivo is provided, the sensor including: a sensor body including RF circuitry encapsulated within a substantially water vapor permeable body that enables RF transmission therethrough; a sensing region located on an outer surface of the sensor body for measuring an analyte in soft tissue; a biointerface material disposed adjacent to the sensing region that supports vascularized tissue ingrowth for transport of the analyte to the sensing region; and an anchoring material on a non-sensing outer surface of the sensor body that supports tissue ingrowth for immobilization of the sensor body in soft tissue.

In an aspect of the seventh embodiment, the sensor further includes an antenna encapsulated within the sensor body. In an aspect of the seventh embodiment, the sensor further includes a power source encapsulated within the sensor body.

In an aspect of the seventh embodiment, the sensor body is formed from plastic. In an aspect of the seventh embodiment, the plastic includes epoxy.

In an aspect of the seventh embodiment, the sensor body is molded around the RF circuitry. In an aspect of the seventh embodiment, the sensor further includes an electrode system exposed at the sensing region. In an aspect of the seventh embodiment, the electrode system extends through the water vapor permeable body and is operably connected to the RF circuitry.

In an aspect of the seventh embodiment, the biointerface material includes a solid portion with a plurality of interconnected cavities. In an aspect of the seventh embodiment, the biointerface material further includes a domain proximal to the sensing region that is impermeable to cells or cell processes and is permeable to the passage of the analyte.

In an eighth embodiment, an electrochemical analyte sensor for measuring an analyte concentration is provided, the sensor including: a sensor body including electronic circuitry encapsulated within the sensor body; and a plurality of electrodes that extend from an outer surface of the sensor body to the encapsulated electronic circuitry, wherein the electrodes are mechanically and electrically connected and aligned to the electronic circuitry prior to encapsulation within the sensor body.

In an aspect of the eighth embodiment, the electrodes are swaged to the electronic circuitry. In an aspect of the eighth embodiment, the electrodes are welded using a technique selected from the group consisting of spot welding, ultrasonic welding, and laser welding.

In an aspect of the eighth embodiment, the electrodes and electronic circuitry are encapsulated in the sensor body by a molding process. In an aspect of the eighth embodiment, the sensor body includes a water vapor permeable material.

In an aspect of the eighth embodiment, the electronic circuitry is spaced from the water vapor permeable sensor body, such that water vapor penetration within a fixed distance from the electronic circuitry is inhibited. In an aspect of the eighth embodiment, the electronic circuitry is spaced from the water vapor permeable sensor body by epoxy. In an aspect of the eighth embodiment, the electronic circuitry is spaced from the water vapor permeable sensor body by a glass tube. In an aspect of the eighth embodiment, the electronic circuitry is spaced from the water vapor permeable sensor body by Parylene. In an aspect of the eighth embodiment, the electronic circuitry is spaced from the water vapor permeable sensor body by one or more hermetic containers.

In an aspect of the eighth embodiment, the sensor body includes a substantially seamless exterior with the electrodes extending through the sensor body to the outer surface thereof.

In a ninth embodiment, a method for manufacturing an electrochemical analyte sensor is provided, the method including: providing electronic circuitry designed to process signals from the sensor; swaging a plurality of electrodes to the electronic circuitry; and molding a plastic material around the electronic circuitry to form the sensor body.

In a tenth embodiment, a method for manufacturing an analyte sensor is provided, the method including: providing sensor electronics designed to process signals from the sensor; conformally coating the sensor electronics with a material that has a first water permeability rate; and molding a water vapor permeable material that has a second water permeability rate around the coated sensor electronics to form a substantially seamless sensor body, wherein the second water permeability rate is greater than the first water penetration rate.

In an aspect of the tenth embodiment, the molding includes a two-step molding process to form the substantially seamless sensor body.

In an aspect of the tenth embodiment, the two-step molding process includes: holding a first portion of the coated sensor electronics and molding around a second portion of the coated sensor electronics; and holding a portion of the cured sensor body and molding around the first portion of the coated sensor electronics.

In an eleventh embodiment, a method for manufacturing a multilayer membrane for an analyte sensor is provided, the method including: serially casting and subsequently curing each of a plurality of layers to form the multilayer membrane onto a liner, wherein the layers include a resistance layer for limiting the passage of an analyte and an enzyme layer including an enzyme for reacting with the analyte; and releasing the multilayer membrane from the liner for application onto the analyte sensor.

In an aspect of the eleventh embodiment, the multilayer membrane further includes an interference layer that substantially prevents passage of potentially electrochemically interfering substances.

In an aspect of the eleventh embodiment, the multilayer membrane further includes an electrolyte layer including a hydrogel for maintaining hydrophilicity at electrochemically reactive surfaces of the analyte sensor.

In a twelfth embodiment, a method for casting a membrane that regulates the transport of glucose, the method including: forming a solvent solution including a polymer blend and a solvent, wherein the polymer blend includes hydrophilic and hydrophobic components; maintaining the solution at a first elevated temperature for a predetermined time period in order to mix the hydrophilic and hydrophobic components with each other and the solvent, wherein the elevated temperature is above room temperature; applying the composition to a liner to form a film thereon; and curing the film, wherein the curing is accomplished while ramping the temperature at a predetermined ramp rate to a second elevated temperature that is above the first temperature.

In an aspect of the twelfth embodiment, the first elevated temperature is between about 60° C. and about 100° C. In an aspect of the twelfth embodiment, the first elevated temperature is about 80° C.

In an aspect of the twelfth embodiment, the predetermined time period is at least about 24 hours. In an aspect of the twelfth embodiment, the predetermined time period is at least about 44 hours.

In an aspect of the twelfth embodiment, the predetermined ramp rate is between about 3° C. per minute and 12° C. per minute. In an aspect of the twelfth embodiment, the predetermined ramp rate is about 7° C. per minute.

In an aspect of the twelfth embodiment, the second elevated temperature is at least about 100° C.

In a thirteenth embodiment, a method for casting a membrane for use with an electrochemical glucose sensor is provided, wherein the membrane substantially prevents passage of potentially electrochemically interfering substances, the method including: forming a sufficiently diluted solvent solution including a polymer and a solvent, wherein sufficiently diluted solvent solution includes a ratio of polymer to solvent of about 1 to 10 wt. % polymer to about 90 to 99 wt. % solvent; and applying the solvent solution at a sufficiently fast casting speed that substantially avoids film thickness inhomogeneities due to evaporation during casting of the sufficiently diluted solvent solution.

In an aspect of the thirteenth embodiment, the membrane limits the diffusion of hydrophilic species and large molecular weight species.

In an aspect of the thirteenth embodiment, the membrane includes a thickness between about 0.1 and 5 microns. In an aspect of the thirteenth embodiment, the membrane includes a thickness between about 0.5 and 3 microns.

In an aspect of the thirteenth embodiment, the polymer includes polyurethane.

In an aspect of the thirteenth embodiment, the sufficiently fast casting speed is between about 8 to about 15 inches/second. In an aspect of the thirteenth embodiment, the sufficiently fast casting speed is about 11.5 inches/second.

In a fourteenth embodiment, an implantable analyte sensor is provided, the sensor including: a body including a material which is permeable to water vapor, the body further including a sensing region for measuring levels of an analyte; and a transmitter within the body for transmitting the measurements obtained by the sensing region, wherein at least a portion of the transmitter is spaced from the body by a material adapted to reduce water from penetrating therein.

In an aspect of the fourteenth embodiment, the transmitter includes an oscillator and at least a portion of the oscillator is spaced from the body by the material adapted to inhibit fluid from penetrating therein. In an aspect of the fourteenth embodiment, the oscillator includes an inductor and wherein the inductor is spaced from the body by the material adapted to inhibit fluid from penetrating therein. In an aspect of the fourteenth embodiment, the oscillator includes a voltage controlled oscillator.

In a fifteenth embodiment, an implantable analyte sensor is provided, including: electronics encapsulated within a water vapor permeable body, wherein the electronics include a microprocessor module and an RF module that has an RF transceiver with a phase-locked loop, and wherein the microprocessor module is programmed to initiate re-calibration of the PLL responsive to detection of off-frequency shift.

In an aspect of the fifteenth embodiment, an electrochemical glucose sensor including a three-electrode system, the sensor including: an electrochemical cell including a working electrode, reference electrode, and counter electrode; and a potentiostat that controls the potential between the working and reference electrodes, wherein an allowable range for the counter electrode voltage is set sufficiently wide such that the glucose sensor can react with other reducible species when oxygen becomes limited and sufficiently narrow to ensure the circuitry does not allow excessive current draw or bubble formation to occur.

In an aspect of the fifteenth embodiment, limiting the current of at least one of the working or counter electrode amplifiers to a preset current value configures the allowable range. In an aspect of the fifteenth embodiment, setting the op-amp to be offset from battery ground configures the allowable range. In an aspect of the fifteenth embodiment, a reference voltage setting between about +0.6V and +0.8V with respect to battery ground configures the allowable range. In an aspect of the fifteenth embodiment, a reference voltage setting of about +0.7V with respect to battery ground configures the allowable range.

In a sixteenth embodiment, a method for manufacturing an analyte sensor is provided, the method including: providing a sensor body, wherein the sensor body includes a sensing region for measuring the analyte; forming a multilayer membrane on a liner; releasing the multilayer membrane from the liner and onto the sensor body; and attaching the multilayer membrane to the analyte sensor body proximal to the sensing region.

In an aspect of the sixteenth embodiment, the attaching step includes a mechanical attachment. In an aspect of the sixteenth embodiment, the mechanical attachment includes a metal or plastic O-ring adapted to fit around a raised sensing region. In an aspect of the sixteenth embodiment, the mechanical attachment includes a metal or plastic disc adapted to be press-fit into the sensor body. In an aspect of the sixteenth embodiment, the mechanical attachment includes a metal or plastic clip adapted to be snap-fit into the sensor body.

In a seventeenth embodiment, a method for manufacturing an analyte sensor is provided, the method including: providing a sensor body, wherein the sensor body includes a sensing region for measuring the analyte; forming a multilayer membrane on a liner; releasing the multilayer membrane from the liner and placing onto the sensor body; and attaching the multilayer membrane to the analyte sensor body proximal to the sensing region.

In an aspect of the seventeenth embodiment, the attaching step includes a mechanical attachment. In an aspect of the seventeenth embodiment, the mechanical attachment includes a metal or plastic O-ring adapted to fit around a raised sensing region. In an aspect of the seventeenth embodiment, the mechanical attachment includes a metal or plastic disc adapted to be press-fit into the sensor body. In an aspect of the seventeenth embodiment, the mechanical attachment includes a metal or plastic clip adapted to be snap-fit into the sensor body.

BRIEF DESCRIPTION OF THE DRAWINGS

FIG. 11A is a perspective view of a sizing tool in one embodiment, including a head and a handle.

FIG. 11B is a side view of the sizing tool of FIG. 11A showing the offset placement of the handle on the head in some embodiments.

FIG. 11C is a top view of the sizing tool of FIG. 11A showing a curvature substantially similar to that of the sensor body.

DETAILED DESCRIPTION OF THE PREFERRED EMBODIMENT

Figure 1A:
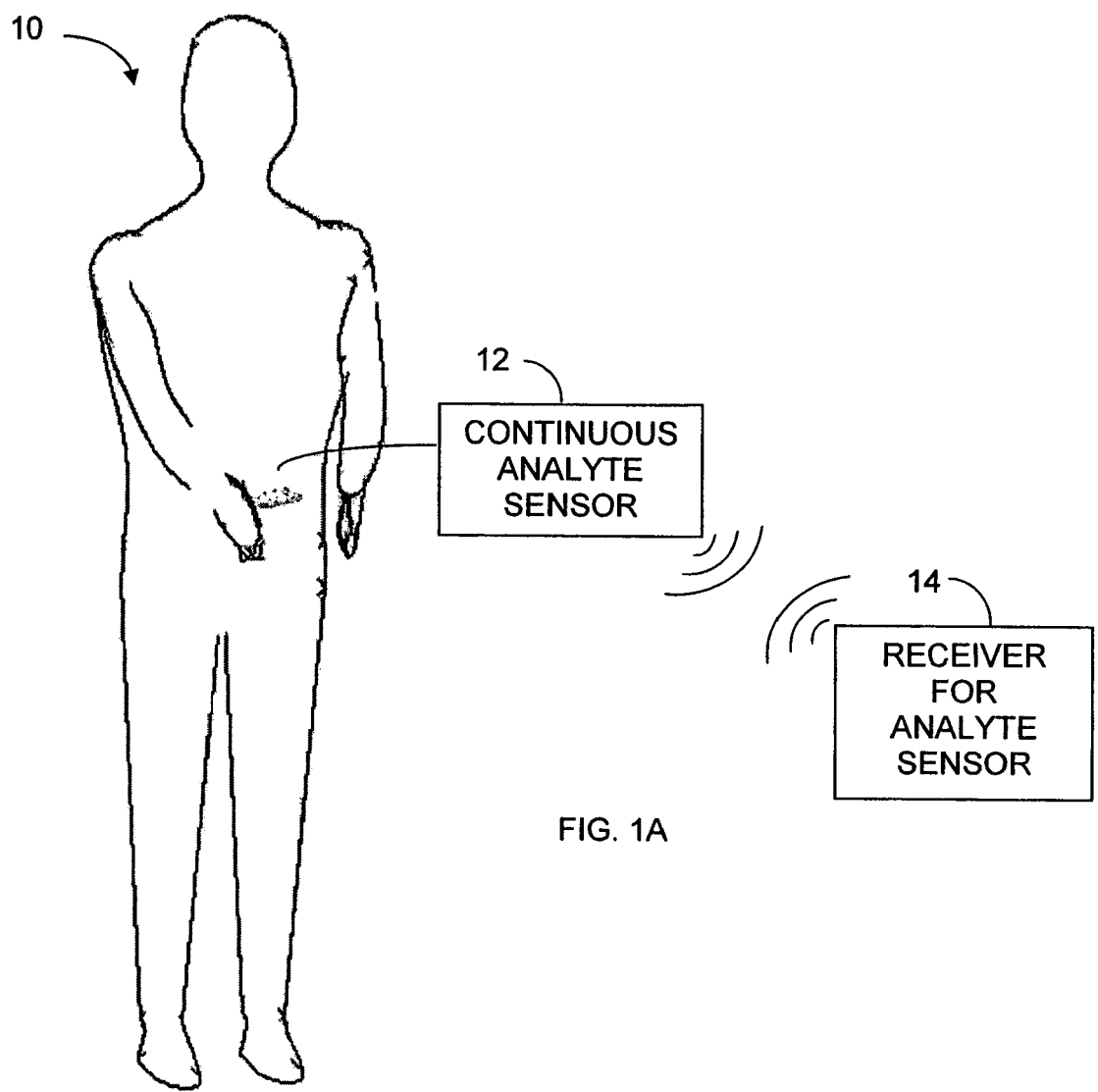
FIG. 1A is a perspective view of a system of the preferred embodiments, including a continuous analyte sensor implanted within a human and a receiver for processing and displaying sensor data.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the disclosed invention, a number of terms are defined below.

The term "ROM," as used herein, is a broad term and is used in its ordinary sense, including, without limitation, read-only memory. The term is inclusive of various types of ROM, including EEPROM, rewritable ROMs, flash memory, or the like.

The term "RAM," as used herein, is a broad term and is used in its ordinary sense, including, without limitation, random access memory. The term is inclusive of various types of RAM, including dynamic-RAM, static-RAM, non-static RAM, or the like.

The term "A/D Converter," as used herein, is a broad term and is used in its ordinary sense, including, without limitation, hardware and/or software that converts analog electrical signals into corresponding digital signals.

The term "microprocessor," as used herein, is a broad term and is used in its ordinary sense, including, without limitation a computer system or processor designed to perform arithmetic and logic operations using logic circuitry that responds to and processes the basic instructions that drive a computer.

The term "RF transceiver," as used herein, is a broad term and is used in its ordinary sense, including, without limitation, a radio frequency transmitter and/or receiver for transmitting and/or receiving signals.

The terms "raw data stream" and "data stream," as used herein, are broad terms and are used in their ordinary sense, including, without limitation, an analog or digital signal directly related to the measured glucose from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "potentiostat," as used herein, is a broad term and is used in its ordinary sense, including, without limitation, an electrical system that controls the potential between the working and reference electrodes of a three-electrode cell at a preset value. It forces whatever current is necessary to flow between the working and counter electrodes to keep the desired potential, as long as the needed cell voltage and current do not exceed the compliance limits of the potentiostat.

The term "electrical potential," as used herein, is a broad term and is used in its ordinary sense, including, without limitation, the electrical potential difference between two points in a circuit which is the cause of the flow of a current.

The term "physiologically feasible," as used herein, is a broad term and is used in its ordinary sense, including, without limitation, the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min/min are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data.

The term "ischemia," as used herein, is a broad term and is used in its ordinary sense, including, without limitation, local and temporary deficiency of blood supply due to obstruction of circulation to a part (for example, sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The term "biointerface membrane" as used herein is a broad term and is used in its ordinary sense, including, without limitation, a permeable membrane that functions as a device-tissue interface comprised of two or more domains. In some embodiments, the biointerface membrane is composed of two domains. The first domain supports tissue ingrowth, interferes with barrier cell layer formation, and includes an open cell configuration having cavities and a solid portion. The second domain is resistant to cellular attachment and impermeable to cells (for example, macrophages). The biointerface membrane is made of biostable materials and can be constructed in layers, uniform or non-uniform gradients (i.e., anisotropic), or in a uniform or non-uniform cavity size configuration.

The term "sensing membrane," as used herein, is a broad term and is used in its ordinary sense, including, without limitation, a permeable or semi-permeable membrane that can be comprised of two or more domains and is typically constructed of materials of a few microns thickness or more, which are permeable to oxygen and may or may not be permeable to glucose. In one example, the sensing membrane comprises an enzyme, for example immobilized glucose oxidase enzyme, which enables an electrochemical reaction to occur to measure a concentration of analyte.

The term "domain" as used herein is a broad term and is used in its ordinary sense, including, without limitation, regions of a membrane that can be layers, uniform or non-uniform gradients (for example, anisotropic) or provided as portions of the membrane. The term is broad enough to include one or more functions one or more (combined) domains, or a plurality of layers or regions that each provide one or more of the functions of each of the various domains.

The term "barrier cell layer" as used herein is a broad term and is used in its ordinary sense, including, without limitation, a cohesive monolayer of cells (for example, macrophages and foreign body giant cells) that substantially block the transport of at least some molecules across the second domain and/or membrane.

The term "cellular attachment," as used herein is a broad term and is used in its ordinary sense, including, without limitation, adhesion of cells and/or mechanical attachment of cell processes to a material at the molecular level, and/or attachment of cells and/or cell processes to micro- (or macro-) porous material surfaces. One example of a material used in the prior art that allows cellular attachment due to porous surfaces is the BIOPORE™ cell culture support marketed by Millipore (Bedford, Mass.) (see Brauker '330, supra).

The phrase "distal to" as used herein is a broad term and is used in its ordinary sense, including, without limitation, the spatial relationship between various elements in comparison to a particular point of reference. For example, some embodiments of a device include a biointerface membrane having a cell disruptive domain and a cell impermeable domain. If the sensor is deemed to be the point of reference and the cell disruptive domain is positioned farther from the sensor, then that domain is distal to the sensor.

The term "proximal to" as used herein is a broad term and is used in its ordinary sense, including, without limitation, the spatial relationship between various elements in comparison to a particular point of reference. For example, some embodiments of a device include a biointerface membrane having a cell disruptive domain and a cell impermeable domain. If the sensor is deemed to be the point of reference and the cell impermeable domain is positioned nearer to the sensor, then that domain is proximal to the sensor.

The term "cell processes" as used herein is a broad term and is used in its ordinary sense, including, without limitation, pseudopodia of a cell.

The term "solid portions" as used herein is a broad term and is used in its ordinary sense, including, without limitation, a solid material having a mechanical structure that demarcates the cavities, voids, or other non-solid portions.

The term "substantial" as used herein is a broad term and is used in its ordinary sense, including, without limitation, a sufficient amount that provides a desired function. For example, in the micro-architecture of the preferred embodiments, a substantial number of cavities have a size that allows a substantial number of inflammatory cells to enter therein, which may include an amount greater than 50 percent, an amount greater than 60 percent, an amount greater than 70 percent, an amount greater than 80 percent, and an amount greater than 90 percent of cavities within a preferred nominal pore size range.

The term "co-continuous" as used herein is a broad term and is used in its ordinary sense, including, without limitation, a solid portion wherein an unbroken curved line in three dimensions exists between any two points of the solid portion.

The term "biostable" as used herein is a broad term and is used in its ordinary sense, including, without limitation, materials that are relatively resistant to degradation by processes that are encountered in vivo.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operably connected" and "operably linked" as used herein are broad terms and are used in their ordinary sense, including, without limitation, one or more components being linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The phrase "continuous (or continual) analyte sensing" as used herein is a broad term and is used in its ordinary sense, including, without limitation, the period in which monitoring of analyte concentration is continuously, continually, and or intermittently (regularly or irregularly) performed, for example, about every 5 to 10 minutes.

The term "sensing region" as used herein is a broad term and is used in its ordinary sense, including, without limitation, the region of a monitoring device responsible for the detection of a particular analyte. The sensing region generally comprises a non-conductive body, a working electrode (anode), a reference electrode and a counter electrode (cathode) passing through and secured within the body forming an electrochemically reactive surface at one location on the body and an electronic connective means at another location on the body, and a multi-region membrane affixed to the body and covering the electrochemically reactive surface. The counter electrode has a greater electrochemically reactive surface area than the working electrode. During general operation of the sensor a biological sample (for example, blood or interstitial fluid) or a portion thereof contacts (directly or after passage through one or more membranes or domains) an enzyme (for example, glucose oxidase); the reaction of the biological sample (or portion thereof) results in the formation of reaction products that allow a determination of the analyte (for example, glucose) level in the biological sample. In some embodiments, the multi-region membrane further comprises an enzyme domain (for example, and enzyme layer), and an electrolyte phase (i.e., a free-flowing liquid phase comprising an electrolyte-containing fluid described further below).

The term "electrochemically reactive surface" as used herein is a broad term and is used in its ordinary sense, including, without limitation, the surface of an electrode where an electrochemical reaction takes place. In the case of the working electrode, the hydrogen peroxide produced by the enzyme catalyzed reaction of the analyte being detected reacts creating a measurable electric current (for example, detection of glucose analyte utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "electronic connection" as used herein is a broad term and is used in its ordinary sense, including, without limitation, any electronic connection known to those in the art that can be utilized to interface the sensing region electrodes with the electronic circuitry of a device such as mechanical (for example, pin and socket) or soldered.

The term "oxygen antenna domain" as used herein is a broad term and is used in its ordinary sense, including, without limitation, a domain composed of a material that has higher oxygen solubility than aqueous media so that it concentrates oxygen from the biological fluid surrounding the biointerface membrane. The domain can then act as an oxygen reservoir during times of minimal oxygen need and has the capacity to provide on demand a higher oxygen gradient to facilitate oxygen transport across the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

The term "casting" as used herein is a broad term and is used in its ordinary sense, including, without limitation, a process where a fluid material is applied to a surface or surfaces and allowed to cure. The term is broad enough to encompass a variety of coating techniques, for example, using a draw-down machine, dip coating, or the like.

The term "water vapor permeable" as used herein is a broad term and is used in its ordinary sense, including, without limitation, characterized by permitting water vapor to permeate therethrough.

The following abbreviations apply herein: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); and ° C. (degrees Centigrade).

Overview

FIG. 1A is a perspective view of a system of the preferred embodiments, including a continuous analyte sensor 12 implanted within a human 10 and a receiver 14 for processing and displaying sensor data. The system of the preferred embodiments provides improved convenience and accuracy because of its discrete design that enables acceptance into a host's tissue with minimum invasive trauma, while providing reliable wireless transmissions through the physiological environment, and thereby increases overall patient comfort, confidence, safety, and convenience.

The continuous analyte sensor 12 measures a concentration of an analyte or a substance indicative of the concentration or presence of the analyte. Although some of the following description is drawn to a glucose sensor, the analyte sensor 12 may be any sensor capable of determining the level of any analyte in the body, for example oxygen, lactase, insulin, hormones, cholesterol, medicaments, viruses, or the like. Additionally, although much of the description of the analyte sensor is focused on electrochemical detection methods, the systems and methods may be applied to analyte sensors that utilize other measurement techniques, including enzymatic, chemical, physical, spectrophotometric, polarimetric, calorimetric, radiometric, or the like.

Figure 2:
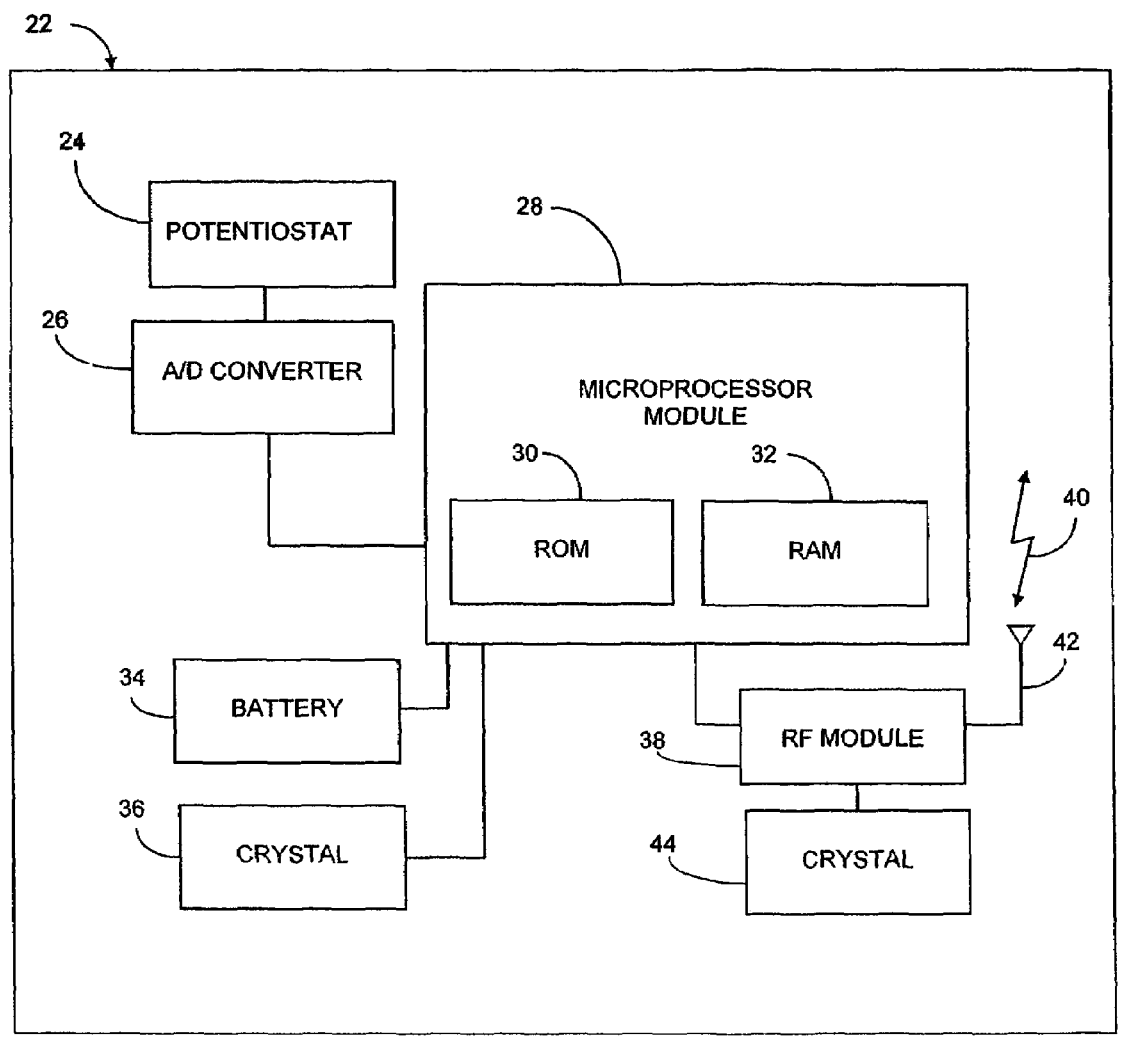
FIG. 2 is a block diagram that illustrates the electronics associated with the implantable glucose sensor in one embodiment.

FIGS. 2 to 13 describe the systems and methods associated with the manufacture, configuration, and implantation of the analyte sensor of the preferred embodiments. FIG. 2 describes systems and methods for measuring an analyte concentration and providing an output signal indicative of the concentration of the analyte, in one embodiment. This output signal is typically a raw data stream that is used to provide a useful value of the measured analyte concentration to a patient or doctor, for example. Accordingly, a receiver 14 is provided that receives and processes the raw data stream, including calibrating, validating, and displaying meaningful glucose values to a patient, such as described in co-pending U.S. patent application Ser. No. 10/633,367, which is incorporated herein by reference in its entirety.

Figure 1B:
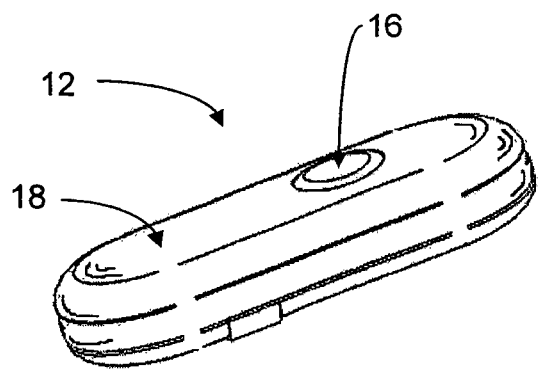
FIG. 1B is a perspective view of the implantable analyte sensor of the preferred embodiments.

Reference is now made to FIG. 1B, which is a perspective view of the implantable analyte sensor 12 of the preferred embodiments. In this embodiment, a sensing region 16 and a non-sensing region 18 are shown on the analyte sensor 12. Electronics associated with the analyte sensor 12 are described in more detail below with reference to FIGS. 2 and 3. The sensor electronics are preferably encapsulated within a molded plastic body, for example, a thermoset, such as described in more detail below with reference to FIGS. 4 and 5. The sensor electronics include an electrode system that extends through the molded body and is exposed at the sensing region 16, such as described in more detail below with reference to FIG. 3. A sensing membrane covers the exposed electrodes, which is described in more detail below with reference to FIG. 7. A biointerface membrane, which covers the sensing membrane, is configured to support tissue ingrowth, disrupt contractile forces typically found in a foreign body response, encourage vascularity, and interfere with barrier cell layer formation, and is described in more detail below with reference to FIG. 8. An anchoring material covers at least a portion of the non-sensing region of the analyte sensor 12 for long-term anchoring of the sensor to the host tissue, which is described in more detail below with reference to FIGS. 10 and 13. A suture strip or other component for short-term anchoring of the sensor to the host tissue may optionally be provided. In some embodiments, the component for short-term anchoring of the sensor to the host tissue may be on a portion of the non-sensing region, as described in more detail below with reference to FIGS. 10 and 12.

In one preferred embodiment, the analyte sensor is a glucose sensor, wherein the sensing region 16 comprises electrode system including a platinum working electrode, a platinum counter electrode, and a silver/silver chloride reference electrode, for example. However a variety of electrode materials and configurations may be used with the implantable analyte sensor of the preferred embodiments. The top ends of the electrodes are in contact with an electrolyte phase (not shown), which is a free-flowing fluid phase disposed between a sensing membrane and the electrodes. In one embodiment, the counter electrode is provided to balance the current generated by the species being measured at the working electrode. In some embodiments, the sensing membrane includes an enzyme, for example, glucose oxidase, and covers the electrolyte phase. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

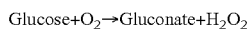

Glucose+$O_2$→Gluconate+$H_2O_2$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

A potentiostat (FIG. 3C) is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

DESCRIPTION

Sensor Electronics

FIG. 2 is a block diagram that illustrates the electronics 22 associated with the implantable glucose sensor 12 in one embodiment. In this embodiment, a potentiostat 24 is shown, which is operably connected to an electrode system (such as described above) to obtain a current value, and includes a resistor (not shown) that translates the current into voltage. An A/D converter 26 digitizes the analog signal into "counts" for processing. Accordingly, the resulting raw data stream in counts is directly related to the current measured by the potentiostat 24.

A microprocessor module 28 includes the central control unit that houses ROM 30 and RAM 32 and controls the processing of the sensor electronics 22. It is noted that certain alternative embodiments can utilize a computer system other than a microprocessor to process data as described herein. In some alternative embodiments, an application-specific integrated circuit (ASIC) can be used for some or all the sensor's central processing as is appreciated by one skilled in the art. The ROM 30 provides semi-permanent storage of data, for example, storing data such as sensor identifier (ID) and programming to process data streams (for example, programming for data smoothing and/or replacement of signal artifacts such as described in copending U.S. patent application Ser. No. 10/648,849 and entitled, "SYSTEMS AND METHODS FOR REPLACING SIGNAL ARTIFACTS IN A GLUCOSE SENSOR DATA STREAM," filed Aug. 22, 2003, which is incorporated herein by reference in its entirety). The RAM 32 can be used for the system's cache memory, for example for temporarily storing recent sensor data. In some alternative embodiments, memory storage components comparable to ROM 30 and RAM 32 may be used instead of or in addition to the preferred hardware, such as dynamic-RAM, static-RAM, non-static RAM, EEPROM, rewritable ROMs, flash memory, or the like.

A battery 34 is operably connected to the sensor electronics 22 and provides the necessary power for the sensor 12. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. In yet other embodiments, the sensor can be transcutaneously powered via an inductive coupling, for example. In some embodiments, a quartz crystal 36 is operably connected to the microprocessor 28 and maintains system time for the computer system as a whole.

An RF module 38 is operably connected to the microprocessor 28 and transmits the sensor data from the sensor 12 to a receiver 14 within a wireless transmission 40 via antenna 42. In some embodiments, a second quartz crystal 44 provides the system time for synchronizing the data transmissions from the RF transceiver. The RF transceiver generally includes a register and a phase-locked loop (PLL) with an oscillator, phase discriminator (PD), loop filter (LPF), and a voltage-controlled oscillator (VCO) as is appreciated by one skilled in the art. In some alternative embodiments, however, other mechanisms such as optical, infrared radiation (IR), ultrasonic, or the like may be used to transmit and/or receive data.

It is noted that the preferred embodiments advantageously encapsulate the electronics in a water vapor permeable material, such as described in more detail with reference to FIGS. 4 to 5, below. It has been observed, however, that a change of the electrical properties of the water permeable sensor body contributes to a changing dielectric loading of the RF, causing shifting of the carrier frequency that may prohibit a receiver (for example, listening in a particular frequency range) from receiving the data transmissions. Although conventional PLL's are designed to run a standard calibration to compensate for dielectric loading changes over time, it has been seen that certain situations occur in an implantable water vapor permeable sensor, wherein the water penetration rate increases more quickly than can be compensated for in a standard calibration cycle. Accordingly, the preferred embodiments are programmed to monitor the PLL to determine when the carrier frequency has shifted outside of the predetermined range and to run a re-calibration cycle upon an indication of "off-frequency." While not wishing to be bound by theory, it is believed that re-calibrating the PLL responsive to detection of off-frequency reduces or eliminates missing data transmissions that result from a shifting carrier frequency in an implantable water vapor permeable sensor.

Electronics Subassembly

Figure 3A:
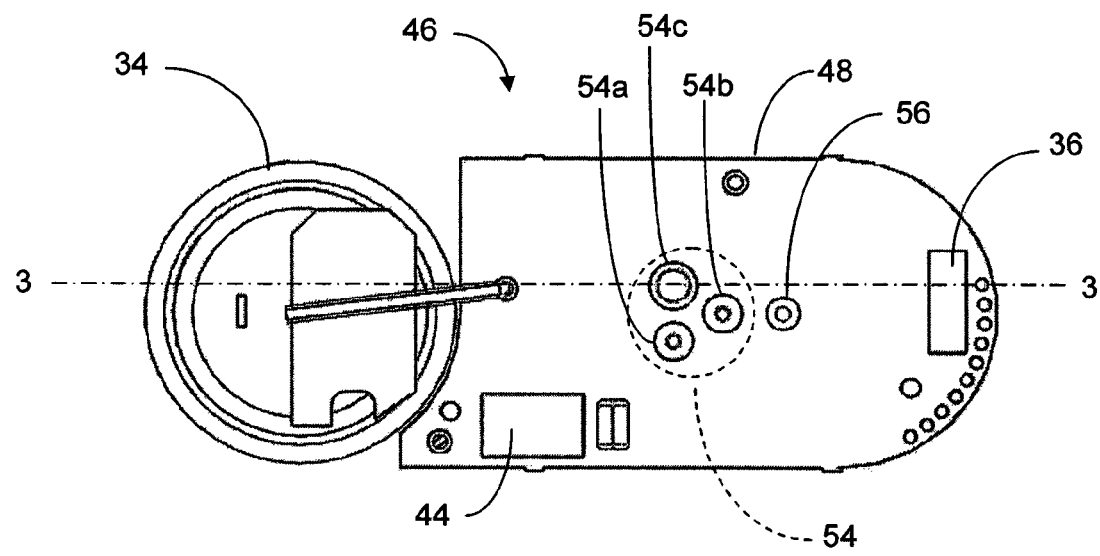
FIG. 3A is a top view of the electronics subassembly of the analyte sensor, which shows the electrode system.
Figure 3B:
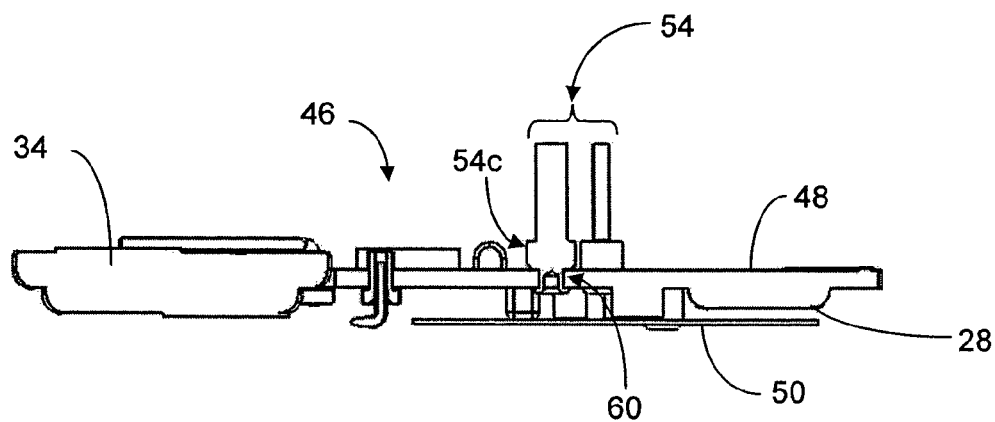
FIG. 3B is a side cross-sectional view of the electronics subassembly taken through line 3-3 on FIG. 3A.

FIGS. 3A and 3B are top (FIG. 3A) and side cross-sectional (FIG. 3B) views of the electronic subassembly 46 associated with the sensor 12 in one exemplary embodiment, which includes the hardware and software that provides for the functionality of sensor electronics as described above. Particularly, FIGS. 3A and 3B illustrate the electronics subassembly 46 prior to encapsulation in a moldable plastic material.

The electronics subassembly 46 generally includes hardware and software designed to support the functions described above; additionally, the electronics subassembly of the preferred embodiments is configured to accommodate certain preferred design parameters described herein, which facilitate analyte sensor immobilization within the subcutaneous pocket. Immobilization of the sensor within the host tissue is advantageous because motion (for example, acute and/or chronic movement of the sensor in the host tissue) has been found to produce acute and/or chronic inflammation, which has been shown to result in poor short-term and/or long-term sensor performance. For example, during an experiment wherein larger, bulkier versions of the analyte sensor were implanted in humans for an average of 44 days+/−14 days [See Garg, S.; Schwartz, S.; Edelman, S. "Improved Glucose Excursions Using an Implantable Real-Time Continuous Glucose Sensor in Adults with Type I Diabetes." *Diabetes Care* 2004, 27, 734-738], it was discovered that movement of the sensor resulted in thicker foreign body capsule formation, which correlated with decreased sensor performance. While not wishing to be bound by theory, it is believed that size optimization (for example, miniaturization) of the analyte sensor enables more discrete and secure implantation, and is believed to reduce macro-motion of the sensor induced by the patient and micro-motion caused by movement of the sensor within the subcutaneous pocket, and thereby improve sensor performance.

Additionally, in contrast to devices made from hermetic materials, the preferred embodiments of the present invention advantageously encapsulate the electronics in a material that is water vapor permeable. The use of a water vapor permeable material, for example moldable plastic, is advantageous for a variety of reasons described elsewhere herein, for example, ease of design changes, security and alignment of the electronics during and after the molding process, and the ability to machine the device with precise curvatures. In some embodiments, the electronic subassembly possesses features that maintain the frequency of the voltage controlled oscillator (VCO) if water vapor penetrates into the water vapor permeable sensor body. For example, in some embodiments, the electronics subassembly reduces changes in the inductor parameters, which may otherwise occur as a result of water vapor within the electromagnetic field of the inductor (for example, which may result in a shift in the carrier frequency of the VCO). Such field effects may cause the VCO to transmit off of its tuned carrier frequency, which degrades the RF telemetry capabilities of the sensor. Furthermore, the carrier frequency of the sensor of the preferred embodiments is optimized for sensor longevity.

Additionally, the analyte sensor of the preferred embodiments supports a high frequency, low power operation, which supports miniaturization of the analyte sensor with optimized functionality. Accordingly, the design of the electronics subassembly 46 of the preferred embodiments provides a discrete, efficient configuration, while maintaining long-term power supply and functional RF telemetry within the water vapor permeable body in vivo.

FIGS. 3A and 3B generally show the electronics subassembly 46 of the preferred embodiments including a printed circuit board (PCB) 48, an antenna board 50, a battery 34, and a plurality of interconnections therebetween, which are configured to provide the above described functionality, as is appreciated by one skilled in the art. FIG. 3A is a top view of the electronics subassembly of the analyte sensor 12, which shows the electrode system 54 described in the Overview section, above. FIG. 3B is a side cross-sectional view of the electronics subassembly taken from line 3-3 on FIG. 3A.

The PCB 48 supports the components, for example microprocessor module 28, including ROM 30 and RAM 32, the potentiostat 24, A/D converter 26, RF module 38, two crystals 36, 44, and a variety of other supporting components, deposited bonding pads, and conductors, which provide the necessary functionality described above. Additionally, the electronics subassembly 46 supports an electrode system 54 including a working electrode 54a, a reference electrode 54b, and a counter electrode 54c in one embodiment, such as described in more detail above in the Overview section, however alternative electrode systems and/or measurement techniques may be implemented.

The antenna board 50, on which the antenna (42 in FIG. 2) is disposed (not shown on FIG. 3A or FIG. 3B), is connected to the PCB 48 via antenna feed 56. Preferably the antenna 42 is surface mounted to the antenna board 50 to further support the reduction of size of the subassembly 46. The PCB 48 and antenna board 50 may be formed in any typical manner such as epoxy-glass and polyamide flex printed wiring boards, ceramic, or silicon substrates. One skilled in the art may appreciate other hardware components, software configurations, and interconnections not described herein.

Electrode System

Figure 3C:
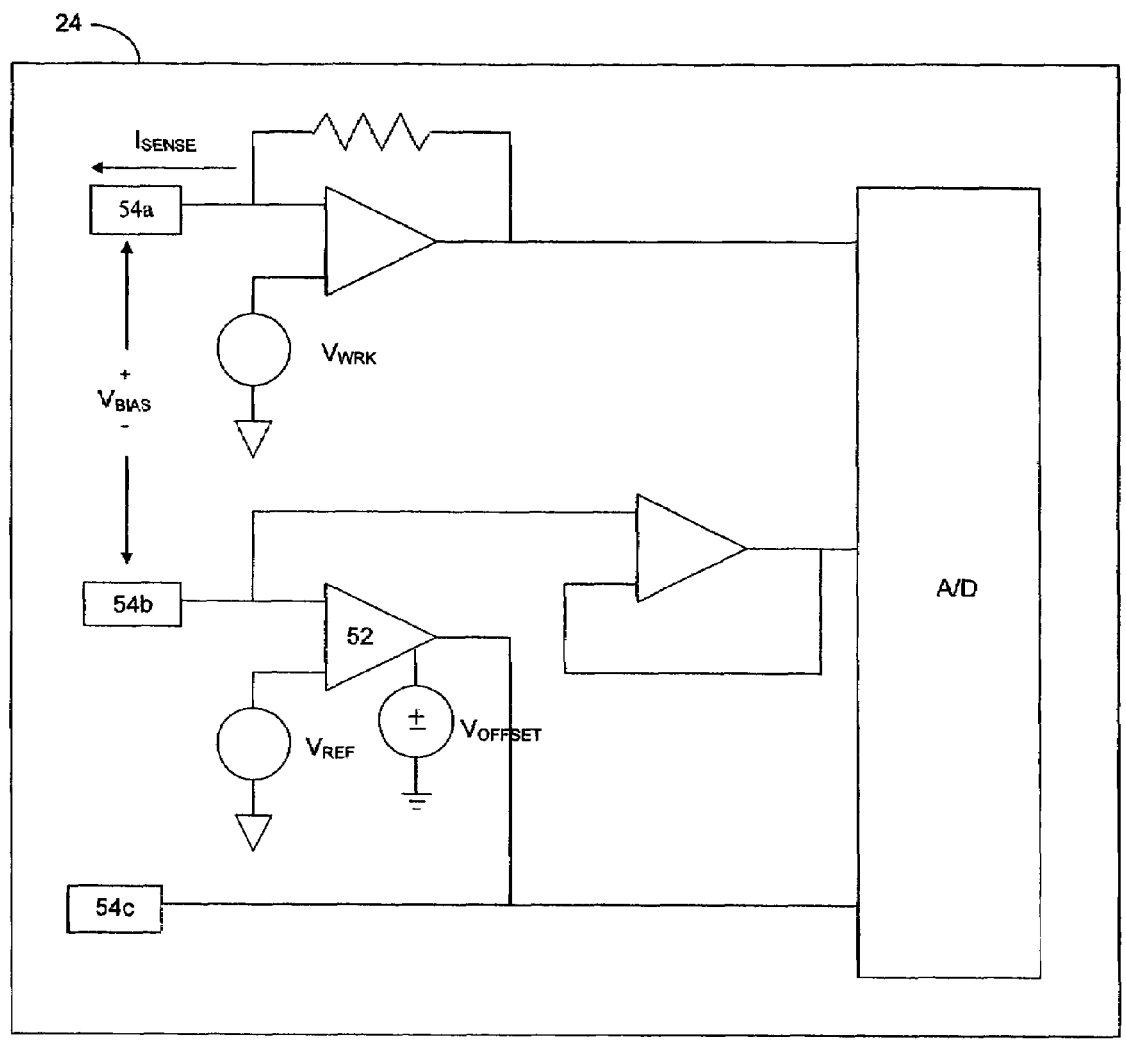
FIG. 3C is a circuit diagram of the potentiostat that controls the three-electrode system of the preferred embodiments.

Reference is now made to the electrode system 54 of the preferred embodiments, including the working electrode (anode) 54a, the reference electrode 54b, and the counter electrode (cathode) 54c, such as shown in FIGS. 3A and 3C. Although alternative electrode configurations and measurement techniques may be used with the preferred embodiments, the following description is focused on the preferred three-electrode system, which is described above in the Overview section.

The working electrode 54a and counter-electrode 54c of a glucose oxidase-based glucose sensor 12 require oxygen in different capacities. Within the enzyme layer above the working electrode 54a, oxygen is required for the production of $H_2O_2$ from glucose. The $H_2O_2$ produced from the glucose oxidase reaction further reacts at the surface of the working electrode 54a and produces two electrons. The products of this reaction are two protons ($2H^+$), two electrons ($2e^-$), and one oxygen molecule ($O_2$) (See Fraser, D. M. "An Introduction to In Vivo Biosensing: Progress and problems." In "Biosensors and the Body," D. M. Fraser, ed., 1997, pp. 1-56 John P. Wiley and Sons, New York). In theory, the oxygen concentration near the working electrode 54a, which is consumed during the glucose oxidase reaction, is replenished by the second reaction at the working electrode 54a; therefore, the net consumption of oxygen is zero. In practice, however, not all of the $H_2O_2$ produced by the enzyme diffuses to the working electrode surface nor does all of the oxygen produced at the electrode diffuse to the enzyme domain.

Additionally, the counter electrode 54c utilizes oxygen as an electron acceptor. The most likely reducible species for this system are oxygen or enzyme generated peroxide (Fraser, D. M. supra). There are two main pathways by which oxygen may be consumed at the counter electrode 54c. These are a four-electron pathway to produce hydroxide and a two-electron pathway to produce hydrogen peroxide. Oxygen is further consumed above the counter electrode by the glucose oxidase. Due to the oxygen consumption by both the enzyme and the counter electrode, there is a net consumption of oxygen at the surface of the counter electrode 54c. Thus, in the domain of the working electrode 54a there may be significantly less net loss of oxygen than in the region of the counter electrode 54c. Furthermore, it is noted that there is a close correlation between the ability of the counter electrode 54c to maintain current balance and sensor performance. Taken together, it is believed that counter electrode 54c function becomes limited before the enzyme reaction becomes limited when oxygen concentration is lowered. When this occurs, the counter electrode limitation begins to manifest itself as this electrode moves to increasingly negative voltages in the search for reducible species. Thus, when a sufficient supply of reducible species, such as oxygen, is not available to a conventional sensor, the counter electrode voltage reaches a circuitry limit, resulting in compromised sensor performance.

In order to overcome the above-described limitations, the diameter of the counter electrode is at least twice the diameter of the working electrode, resulting in an approximately 6-fold increase in the exposed surface area of the counter electrode of the preferred embodiment. Preferably, the surface area of the electrochemically reactive surface of the counter electrode is not less than about 2 times the surface area of the working electrode. More preferably, the surface area of the electrochemically reactive surface of the counter electrode is between about 2 and about 50, between about 2 and about 25, or between about 2 and about 10 times the surface area of the working electrode.

Reference is now made to FIG. 3C, which is a circuit diagram of the potentiostat 24 that controls the three-electrode system 54 of the preferred embodiments. The potentiostat includes electrical connections to the working electrode 54a, the reference electrode 54b, and the counter electrode 54c. The voltage applied to the working electrode 54a is a constant value and the voltage applied to the reference electrode is also set at a constant value such that the potential ($V_{BIAS}$) applied between the working and reference electrodes is maintained at a constant value. The counter electrode 54c is configured to have a constant current (equal to the current being measured by the working electrode 54a), which is accomplished by varying the voltage at the counter electrode in order to balance the current going through the working electrode 54a such that current does not pass through the reference electrode 54c. A negative feedback loop 52 is constructed from an operational amplifier (OP AMP), the reference electrode 54b, the counter electrode 54c, and a reference potential ($V_{REF}$), to maintain the reference electrode at a constant voltage.

Thus, potentiostat 24 creates current in the counter electrode by controlling the voltage applied between the reference and the working electrode. The reaction that occurs on the counter electrode is determined by how much voltage is applied to the counter electrode. By increasing the voltage applied to the counter electrode, increased amount and type of species may react in order to create the necessary current, which may be advantageous for the same reasons as described above with reference to the electrode configuration of the preferred embodiments.

In addition to the net oxygen loss described above, implantable glucose sensors face an additional challenge in maintaining sensor output during ischemic conditions, which may occur either as short-term transient events (for example, compression caused by postural effects on the device) or as long-term low oxygen conditions (for example, caused by a thickened FBC or barrier cells). When the sensor is in a low oxygen environment, the potentiostat will react by decreasing the voltage relative to the reference electrode voltage applied to the counter electrode, which may result in other less electro-active species reacting at the counter electrode.

In some embodiments, the potentiostat settings are configured to allow the counter electrode to react with other reducible species when oxygen concentration is low. In some circumstances, glucose sensors may suffer from a negative voltage setting that is too low, particularly in low oxygen environments. For example, as the voltage on the counter electrode becomes more negative, it will begin to create current, by reacting with other reducible species, a byproduct of this reaction is $H_2$. Two potential problems can occur because of the production of Hydrogen at the counter electrode: 1) bubble formation, which disconnects the counter from the current carrying buffer and causes the sensor to lose function and 2) an interfering signal at the working electrode.

In order to overcome the potential problems, the preferred embodiments optimize the potentiostat settings to enable functionality of the potentiostat even in low oxygen conditions while limiting the counter electrode to ensure that the sensor does not create conditions that could damage it. Namely, such that when oxygen concentration decreases, the counter electrode is pushed negative enough to allow it to react with the next most abundant reducible species, for example water, which is not typically limited (for example, in vivo).

In one embodiment, the potentiostat settings are optimized by setting the allowable range for the counter electrode voltage sufficiently wide such that the sensor can react with other reducible species when oxygen becomes limited, while setting the range sufficiently narrow to ensure the circuitry does not allow excessive current draw or bubble formation to occur. The counter electrode is preferably restricted such that the species that will react at the counter electrode electroactive surface do not restrict the contact of the counter electrode, while causing excess current flow and potential current damage. Thus, the negative voltage range is preferably wide enough to function in low oxygen environments, while being limited enough to prevent the sensor from applying a voltage to the counter electrode that would cause bubble formation. The limit also provides a fail-safe mechanism for prevention of a $H_2$ feedback loop. If hydrogen diffuses to the working electrode and creates current the counter electrode would be pushed to its electronic limit. When the potentiostat reaches the electronic limit it is no longer able to maintain the potential applied between the working and the reference electrode and the applied potential is decreased. At this point, a maximum limiting electrode current condition is attained. Additionally, the optimized potentiostat settings of the preferred embodiments provide a failsafe mechanism that prevents a cascade reaction that could cause damage to the sensor.

In one implementation of an implantable glucose sensor, a reference voltage between about +0.6V and +0.8V, and preferably about +0.7V, with respect to battery ground is chosen to ensure functionality even in low oxygen conditions yet limiting the counter electrode to a minimum of potential equal to ground potential to ensure that the sensor does not create conditions that could damage it. However, one skilled in the art appreciates that the ratio of the electroactive surface areas of the working and counter electrodes will influence the voltage operating point of the counter electrode with larger counter electrode areas requiring a less negative voltage relative to the reference electrode voltage for the same working electrode current. Additionally, one skilled in the art appreciates that optimization of the potentiostat to produce the above-described results can be attained by limitations other than on the reference voltage, for example, by limiting the current of the working or counter electrode amplifiers to a preset current limit or by setting or the op-amp offset ($V_{OFFSET}$) from battery ground (see FIG. 3C).

Figure 3D:
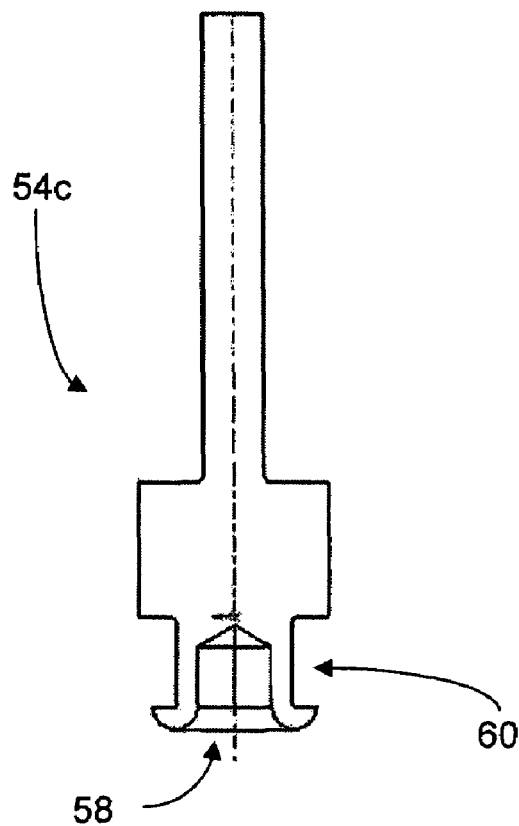
FIG. 3D is an expanded cross-sectional view of a swaged electrode in one embodiment.

Reference is now made to FIGS. 3B and 3D, which illustrate the electrode system of the preferred embodiments configured for secure electrical connection and secure mechanical alignment to the PCB 48. Although other methods for forming electrodes may be used, the preferred embodiments provide bulk metal electrodes, which provide for optimum quality and function of the electrodes in the analyte sensor. It is noted that even slightly insecure attachment and alignment of the electrodes to the board (for example, as has been seen with soldering) may jeopardize the superior performance of bulk metal electrodes due to slippage, disconnect, or the like. Additionally, there is a concern that heat may cause damage to the sensitive PCB electronics if subjected to a heat-bonding type process. Furthermore, the subsequent manufacturing steps (for example, molding) could alter or damage even slightly insecure components and interconnections.

Therefore, the preferred embodiments provide for a mechanical and electrical connection of the electrodes 54 to the PCB 48 that is extremely secure, robust, and easily reproducible in manufacture. In preferred embodiments, the electrodes 54 are swaged to the PCB 48 prior to assembling the electronics subassembly. Referring to FIG. 3D, which is an expanded cross-sectional view of the swaged electrode 54c shown in FIG. 3B, the lower portion 58 of the electrode 54c has been shaped by force around the PCB 48 (FIG. 3B) such that the electrode is tightly held within the necessary electrical connections 60 therein. It is noted that swaged connections may additionally include a solder bead to provide further reliability of the electrical connector.

Swaging is a process whereby metal is shaped by hammering or pressure with the aid of a form or anvil called a swage block, substantially without heating. Notably, swaging is a solderless attachment with good mechanical accuracy, stability, orientation, and provides a quick and clean method of manufacture. The resulting swaged electrode-to-PCB connection 60 at least in part enables the reliable encapsulation of the electronics subassembly in a molded material and longevity of the device due to reliability and reproducibility of a stable electrode system 54.

In some alternative embodiments the electrodes 54 are welded to the PCB 48, which may include, for example, spot welding, laser welding, ultrasonic welding, or the like. Although these techniques include some heating, they are typically cleaner than conventional soldering techniques, for example, and may be advantageous in the some embodiments.

RF Telemetry

Figure 3E:
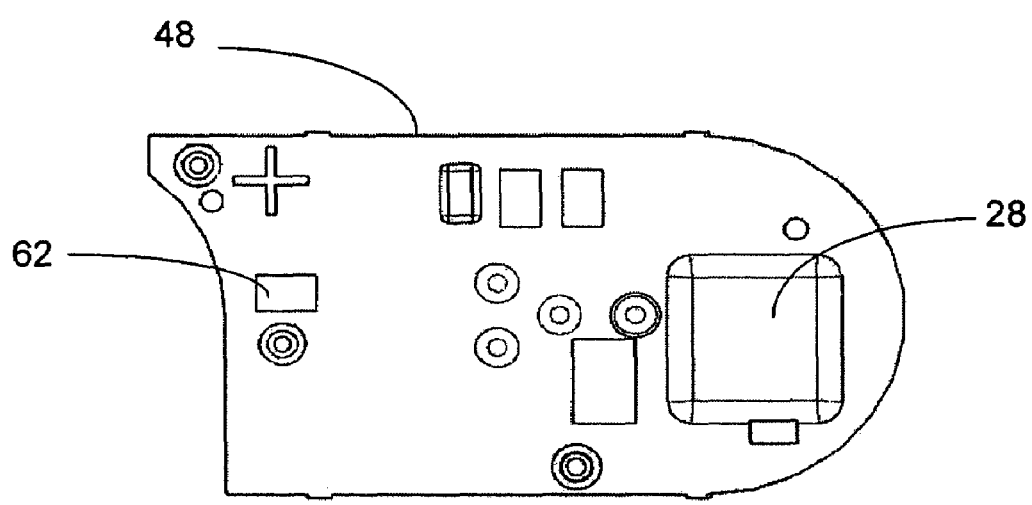
FIG. 3E is a bottom view of the PCB, showing the side of the PCB that faces the antenna board.

FIG. 3E is a bottom view of the PCB 48 only, showing the side of the PCB 48 that faces the antenna board 50 in one embodiment. Notably, the RF module 38 is provided on the PCB 48 and includes VCO circuitry, for example, an inductor 62 that provides a magnetic field suitable for RF telemetry. It is further noted that in some preferred embodiments, the sensor body is substantially formed from a water vapor permeable material, such as described in more detail with reference to FIGS. 4 and 5, below. Unfortunately, if water vapor penetrates through the sensor body to a location that is within the magnetic field produced by the inductor 62, distortion of the electromagnetic field effects may create shifts in the carrier frequency. Generally speaking, when the VCO is unable to provide a stable carrier frequency, the RF transmissions are unlikely or unable to successfully reach their designated receiver (for example, the receiver 14), which has been tuned to the specified carrier frequency. Therefore it is advantageous to reduce or prevent water vapor from entering and distorting the magnetic field created by the inductor in order to maintain a stable dielectric constant within a fixed distance from sensitive RF electronic components.

Figure 3F:
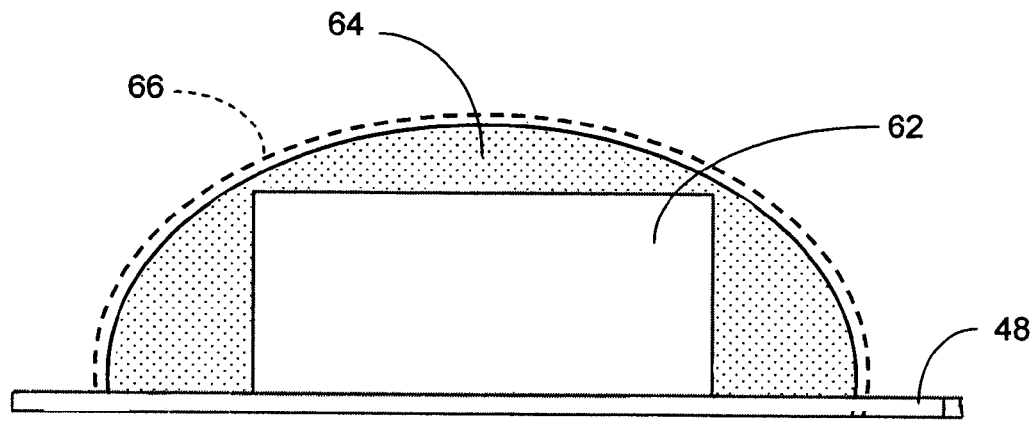
FIG. 3F is a cross-sectional view of an inductor that controls the magnetic field, shown on a cut-away portion of the PCB in one embodiment.
Figure 3G:
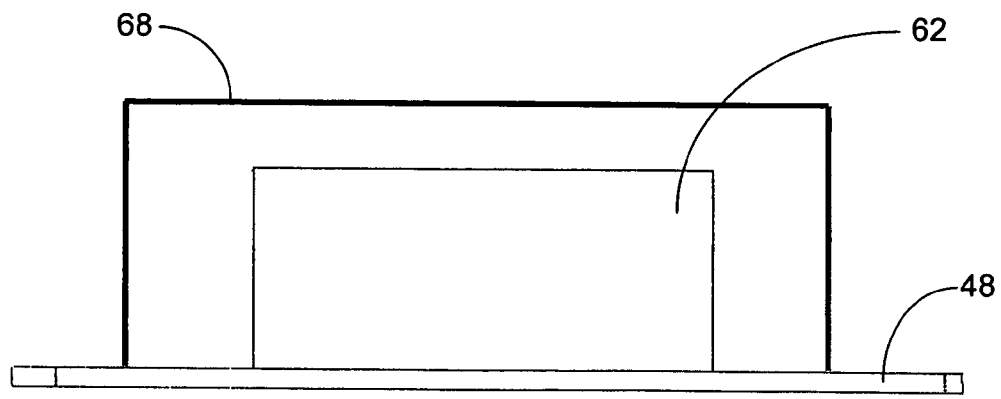
FIG. 3G is a cross-sectional view of an inductor that controls the magnetic field, shown on a cut-away portion of the PCB in an alternative embodiment.

FIGS. 3F and 3G are cross-sectional side views of the inductor 62 on a cut-away portion of the PCB 48, which controls the magnetic field described above. In preferred embodiments, a spacer is provided that substantially prevents or inhibits water vapor from permeating to the magnetic field described above. In one embodiment, such as shown in FIG. 3F, the spacer includes a small volume of a substance 64 applied over the inductor 62 prior to the subsequent manufacturing steps. In one embodiment, the substance 64 is a plastic material, for example, epoxy or silicone. In this case, the purpose of the spacer is to create a fixed space between the inductor 62 and the water vapor permeable sensor body (FIGS. 4 and 5); although epoxy and silicone are known to be water vapor permeable, if desired, an additional less- or minimally-water vapor permeable coating 66 may be applied over part or all of the electronics subassembly 46 including this spacer 64, prior to subsequent manufacture, which is described in more detail below.

In an alternative embodiment, the inductor 62 may be shielded from water vapor by a metal dome, box, or cover 68, for example, such as shown in FIG. 3G. In this embodiment, the metal cover 68 provides the necessary protection from water vapor, however it is noted that the metal cover 68 should be grounded to provide a known, stable potential in the near field of the inductor. Alternatively, the cover 68 may be glass or other hermetic enclosure. Other alternatives for ensuring a stable electromagnetic field may be implemented with the devices of the present invention; for example, a toroidal inductor, which creates a smaller electromagnetic field surrounding the inductor, may be used, thereby decreasing the spacing required. Although two examples are illustrated herein, in general, any design or configuration that provides a substantially water vapor-free space surrounding the magnetic field may be considered a spacer for purposes of the preferred embodiments.

Referring now to the configuration of the RF telemetry module of the preferred embodiments, the hardware and software are designed for low power requirements to increase the longevity of the device (for example, to enable a life of 3 to 24 months) with maximum RF transmittance from the in vivo environment to the ex vivo environment (for example, about one to ten meters). Preferably, a high frequency carrier signal in the range of 402 to 405 MHz is employed in order to maintain lower power requirements. Additionally, the carrier frequency is adapted for physiological attenuation levels, which is accomplished by tuning the RF module in a simulated in vivo environment to ensure RF functionality after implantation. Accordingly, it is believed that the preferred glucose sensor can sustain sensor function for greater than 3 months, greater than 6 months, greater than 12 months, and greater than 24 months.

In some alternative embodiments, hermetic packaging encompasses some parts of the implantable analyte sensor, while water vapor permeable packaging encompasses other parts of the implantable analyte sensor. For example, the implantable analyte sensor body may be formed from a hermetic material (such as Titanium), which encompasses the RF circuitry and/or other water vapor-sensitive components; and a water vapor permeable insert or piece may be incorporated onto the hermetic body, which encompasses the antenna and/or other non-water vapor-sensitive components operably connected thereto. In this way, the RF circuitry and other sensitive components are protected from negative effects that water vapor causes, while allowing unobstructed transmissions and receiving via the antenna.

Protective Coating

In the preferred embodiments, a substantial portion of the electronics 46 is coated with a conformal coating 66. This conformal coating preferably has a water permeability rate that is less than the water permeability rate of the sensor body and enables sufficient spacing for the electromagnetic field as described in more detail above with reference to FIGS. 3F and 3G; additionally the coating protects the PCB 48 and any coated portion of the electronics subassembly 46 from damage during the molding process (FIGS. 4 and 5) and from water permeation that may imbibe through the molded water vapor permeable sensor body over the lifetime of the sensor in vivo.

In one preferred embodiment, one or more conformal Parylene coatings are applied prior to encapsulation in the sensor body. Parylene is known to have a slow water vapor permeability rate and is suitable for biomedical applications. The Parylene coating process exposes product to the gas-phase monomer at low pressure. Through vacuum deposition, Parylene condenses on the object's surface in a polycrystalline fashion, providing a coating that is truly conformal and pinhole free. Compared to liquid processes, the effects of gravity and surface tension are negligible so there is no bridging, thin-out, pinholes, puddling, run-off or sagging; additionally, the process takes place at room temperature so there is no thermal or mechanical stress on the product. Parylene is physically stable and chemically inert within its usable temperature range. Parylene provides excellent protection from water vapor, corrosive vapors, and solvents, for example. In alternative embodiments, other conformal coatings (for example, HumiSeal®, Woodside, N.Y.), spray coatings, or the like, may be used for the less- or minimally-water vapor penetrable layer, which protect the PCB 48 and electronics subassembly 46 from damage during the molding process (FIGS. 4 and 5) and from water penetration through the molded water vapor permeable sensor body in vivo.

In one alternative embodiment, a coating of a secondary material, such as silicone, is applied after the protective coating 66. The secondary coating is preferably made from a material that is able to absorb mechanical stresses that may be translated from the molding process to the sensitive electrical components beneath the protective coating. Thus, silicone, or other similar material with sufficient elasticity or ductility, may be applied to the coated electronics subassembly prior to forming the sensor body, which is described in more detail below.

Sensor Body

In one embodiment, the body of the sensor is preferably formed from a plastic material molded around the sensor electronics, however in alternative embodiments, the body may be formed from a variety of materials, including metals, ceramics, plastics, resins, or composites thereof.

It is noted that conventional prior art implantable sensors that have electronics therein generally use a hermetic material for at least a portion of the body that houses the sensitive electronics. However conventional hermetic implantable devices suffer from numerous disadvantages including: difficulty in RF transmissions through the hermetic material, seams that may allow water vapor penetration if not perfectly sealed, minimal design or shape changes without major manufacturing changes (inability to rapidly iterate on design), and need to mechanically hold and reinforce the electronics inside, increased weight and density, for example.

To overcome the disadvantages of the prior art, the preferred embodiments mold a plastic material around the electronics subassembly 46 (FIG. 4B) to form the sensor body, which enables rapid design iterations (for example, changes in design geometry without mold changes), machining into precise dimensions and curvatures, aids with RF transmissions, adds mechanical integrity to components (for example, because the material fills around the subassembly 46 to form a monolithic piece and hold components in place), allows multiple cures (for example, to provide a seamless exterior), and reinforces fragile electrical components. In preferred embodiments, the material is epoxy, however other plastics may also be used, for example, silicone, urethane, or the like.

Referring now to the molding process for forming the body, a two-step process is preferably used in order to provide a total seal of the components within the device and for forming a seamless device with a desired curvature thereon. The two-step molding process decreases micro-fissures that may form during the initial molding step, while mechanically securing and protecting the electrical components. However, some alternative embodiments may utilize a one-step molding process, for example by injection-molding the device.

Figure 4A:
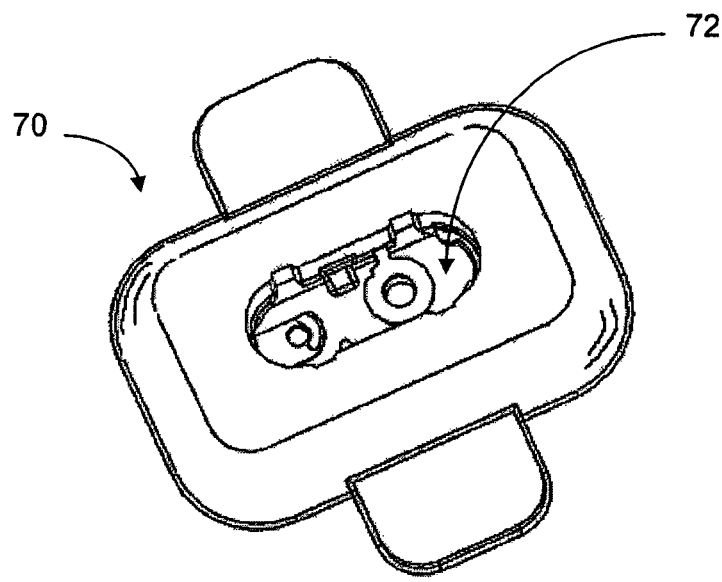
FIG. 4A is a perspective view of the primary mold which is used in the primary casting in one embodiment.
Figure 4B:
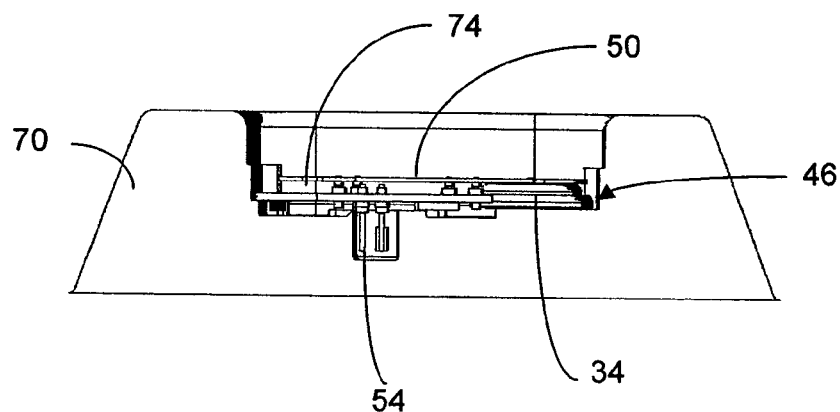
FIG. 4B is a cross-sectional side view of the electronics subassembly during the primary casting process.
Figure 4C:
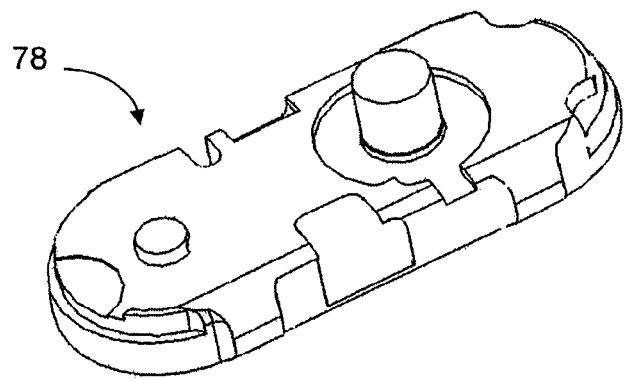
FIG. 4C is a perspective view of the primary potted device after the primary casting process.

FIG. 4A is a perspective view of the primary mold which is used in the primary casting in one embodiment. FIG. 4B is a cross-sectional side view of the electronics subassembly during the primary casting process. FIG. 4C is a perspective view of the primary potted device after the primary casting process.

During the primary casting process, the primary mold 70 is preferably pre-filled with a predetermined amount of a selected plastic material in order to substantially cover the lower portion 72 of the primary mold 70. The electronics subassembly 46 is then pressed into the pre-filled primary mold 70, after which the material 74 is filled around the electronics subassembly 46 to a predetermined fill line or weight amount, ensuring minimal or no air bubbles exist within the material (FIG. 4B). Because of pre-filling, the electrodes 54 are fully encapsulated within the material during the primary cast, which will be machined later to expose electroactive surfaces of the electrodes. This process enables a secure and seamless encapsulation of the electrode system 54 in an insulating material and provides for mechanical alignment, security, and reduces or eliminates leakage of water through the sensing region. Finally, a primary hold down fixture is secured over the device. The material is cured using standard techniques known in the art, for example the plastic material may be placed into a pressure vessel and heated, or the like.

FIG. 4C shows the cured material 74 substantially encapsulating the electronics subassembly 46 after curing, hereinafter referred to as the primary potted device 78. At this point, the components of the electronics subassembly are mechanically aligned and secured with sensitive parts protected from external exposure or damage. However, some parts of the subassembly 46 (for example those parts that were contacting the lower portion of the primary mold) are not encapsulated or covered. Therefore a secondary casting process is provided to fully encapsulate the electronics subassembly, including those portions that are exposed after the primary casting process. Secondary casting enables a seamless and robust sensor body while reinforcing micro-fissures or other microdamage that may have occurred during the primary casting.

Figure 5A:
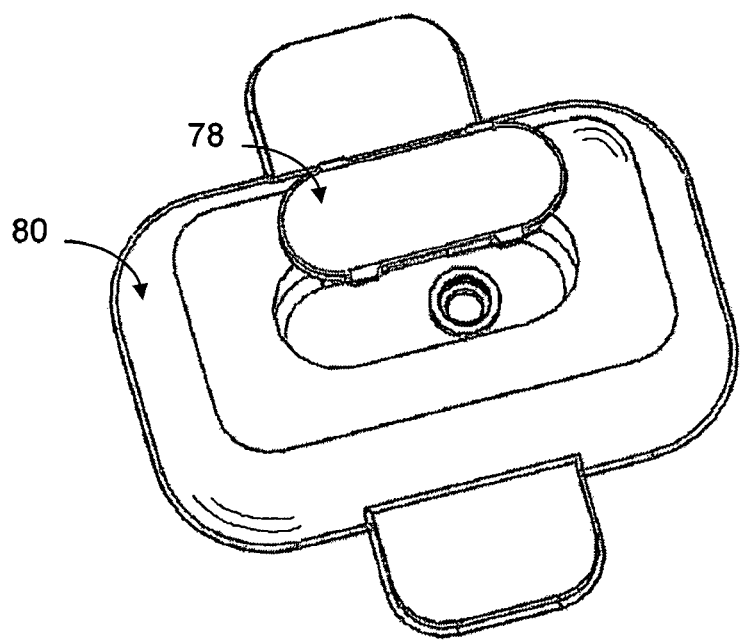
FIG. 5A is a perspective view of inserting the primary potted device into a secondary mold.
Figure 5B:
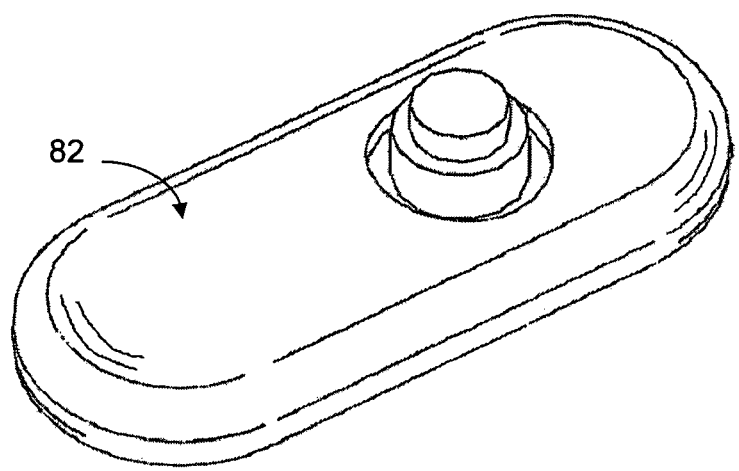
FIG. 5B is a perspective view of the secondary potted device after the secondary casting process.

FIG. 5A is a perspective view of inserting the primary potted device into a secondary mold. FIG. 5B is a perspective view of the secondary potted device after the secondary casting process.

During the secondary casting process, the secondary mold 80 is pre-filled with a predetermined amount of the selected material in order to substantially cover the lower portion of the secondary mold 80. The primary potted device 78 is then pressed into the pre-filled secondary mold 80, after which the material 74 is filled around the primary potted device to a predetermined fill line or weight amount, ensuring minimal or no air bubbles exist within the material. Finally a secondary hold down fixture is secured over the device. The material is cured using standard techniques known in the art, for example the plastic material may be placed into a pressure vessel and heated, or the like. It is noted that this secondary casting is advantageous because it creates additional strength over a primary casting alone, fills in micro-fissures or other damage that may have occurred during or after the primary process, and provides a seamless exterior to prevent leakage into the device.

Reference is now made to FIG. 5B, which shows the secondary potted device 82 prior to final machining. Because of the nature of the plastic material, the sensor can be machined with precise shape and dimensions. For example, the preferred embodiments are machined to a sensor geometry that optimizes healing at the sensor-tissue interface in vivo and is less amenable to accidental movement due to shear and rotational forces than other sensor configurations, such as described in more detail below with reference to FIGS. 6A to 6C. Additionally, machining the molded material to expose the electrodes 54 enables careful exposure of the electroactive surfaces.

It is noted that additional outer coatings may be advantageously applied to the secondary potted device 82, such as one or more Parylene coatings, in order to decrease water vapor penetration, for example. As another example of an outer coating, a silicone layer may be applied to the non-sensing region of the device, which serves to fill in any microfissures or micropores, for example, within the molded material, to provide a smooth outer surface, and/or to enable attachment of additional materials (for example, a silicone anchoring material). Other coatings may be applied as is appreciated by one skilled in the art.

In some alternative embodiments, the electronics subassembly 46 is placed within a pre-formed shell, rather than molding the body around the subassembly. In these alternative embodiments, the shell configuration advantageously provides air space surrounding the electronics, which aids in maintaining a stable dielectric constant surrounding the VCO circuitry, such as described in more detail with reference to FIGS. 3E to 3G. Additionally, the shell provides protection for the electronics subassembly 46 from damage that may occur during a molding process. The pre-formed body shell may be advantageous for manufacture, because it enables the molding process to be separated from the electronics subassembly, reducing the amount of error that may occur to the electronics subassembly in process. It is noted that conformal coatings may be applied to the electronics subassembly prior to encapsulation in the shell, and/or may be applied to the shell itself. Coatings provide a variety of advantages discussed para supra, and with reference to FIG. 3F, for example.

Sensor Geometry

Figure 6A:
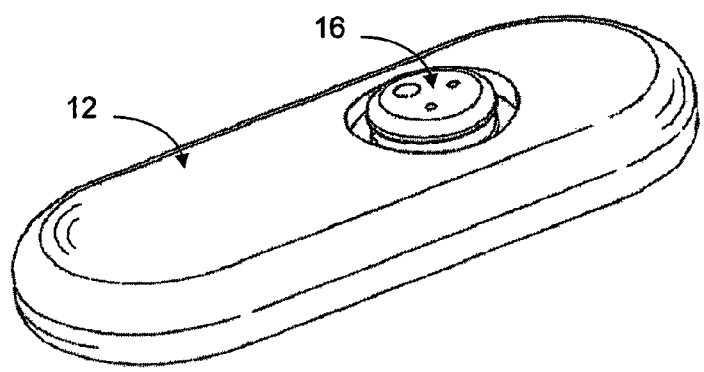
FIG. 6A is a perspective view of an analyte sensor in one embodiment, including a thin substantially oval geometry, a curved sensing region, and an overall curved surface on which the sensing region is located, thereby causing contractile forces from the foreign body capsule to press downward on the sensing region.
Figure 6B:
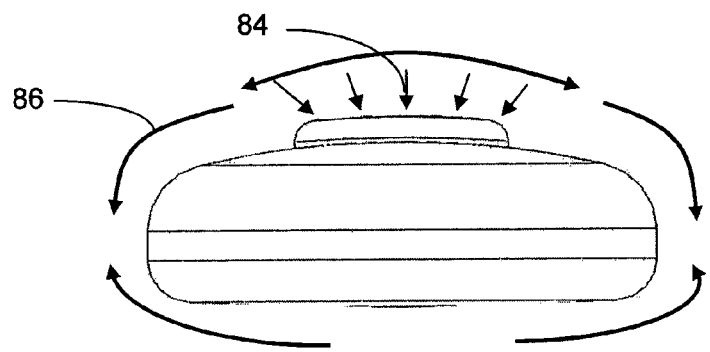
FIG. 6B is an end view of the analyte sensor of FIG. 6A showing the contractile forces that would be caused by a foreign body capsule.
Figure 6C:
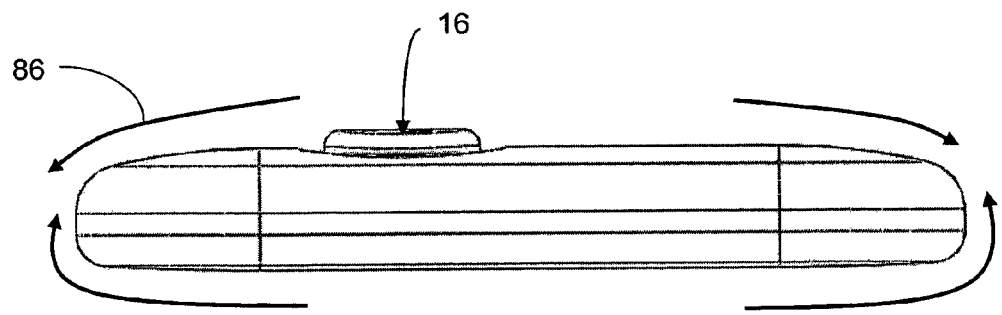
FIG. 6C is a side view of the analyte sensor of FIG. 6A.

FIG. 6A is a perspective view of an analyte sensor in one embodiment, including a thin substantially oval geometry, a curved sensing region, and an overall curved surface on which the sensing region is located, thereby causing contractile forces from the foreign body capsule to press downward on the sensing region. FIG. 6B is an end view of the analyte sensor of FIG. 6A showing the contractile forces that would be caused by a foreign body capsule. FIG. 6C is a side view of the analyte sensor of FIG. 6A.

In this illustration, the analyte sensor 12 is shown without subsequent membrane and anchoring material thereon and is used to illustrate sensor geometry. The analyte sensor 12 includes the sensing region 16 located on a curved portion of the sensor body, and including no abrupt edge or discontinuous surface in the proximity of the sensing region. Additionally, the overall curvature of the surface on which the sensing region is located, including rounded edges, invokes a generally uniform FBC around that surface, decreasing inflammatory response and increasing analyte transport at the device-tissue interface.

Figure 13A:
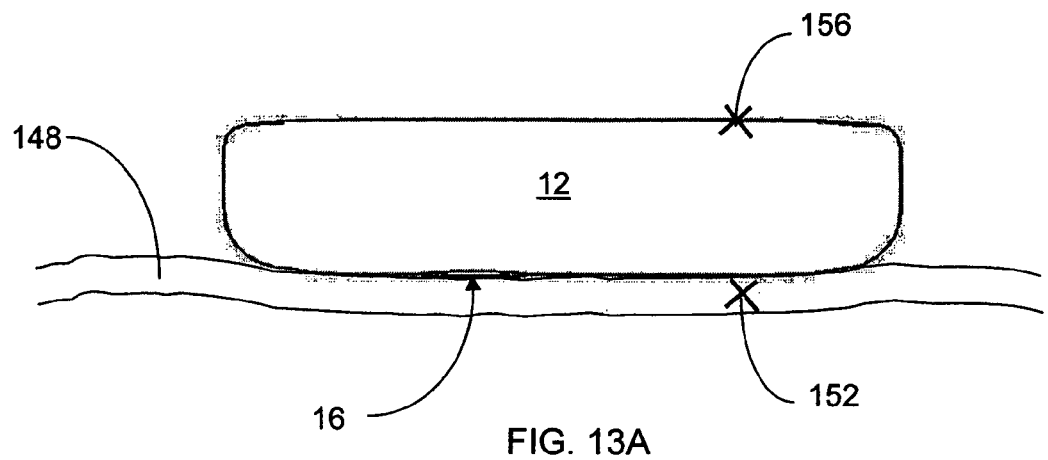
FIG. 13A is a schematic view of the sensor after insertion into the pocket with the sensing region positioned adjacent to the fascia.
Figure 13B:
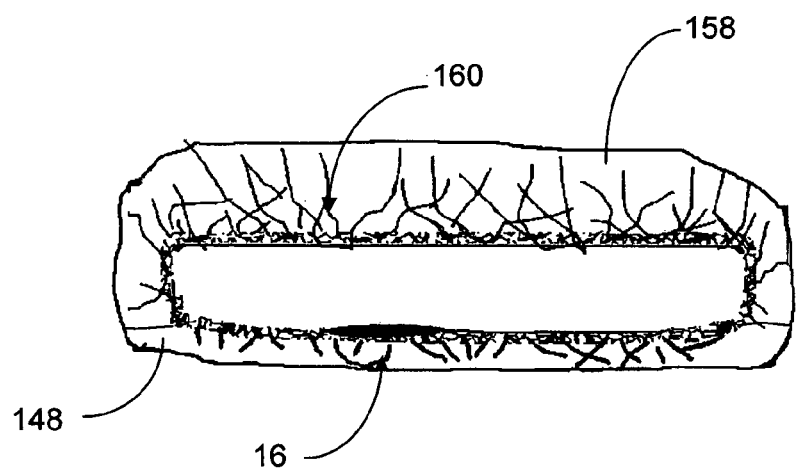
FIG. 13B is a side view of an analyte sensor with long-term anchoring component in the form of an anchoring material on both sides of the sensor.

Perpendicular forces 84, depicted in FIG. 6B by arrows pointing down, represent the forces presented by the foreign body capsule on the device in vivo, which have been found to reduce or eliminate shear forces with the tissue at the sensing region. While lateral forces 86 may appear to create shear forces at the sensing region, several features of the sensor mitigate these forces. For example, the sensor comprises a relatively thin aspect ratio (low profile) and preferably is implanted adjacent to the fascia, underlying the fat, making it less prone to movement. As another example, in some embodiments the sensor may include short-term anchoring components, for example the sensor may be sutured to the tough fascia, which aids in preventing lateral forces from being conveyed to the sensing region (FIG. 13A). In some embodiments, the sensor may include long-term anchoring components, for example an anchoring material may be employed (FIG. 13B). As yet another example, in order to facilitate proper healing, the side of the sensor upon which the sensing region is situated preferably has a curved radius extending from lateral side to lateral side. As depicted in the side view and end view (FIGS. 6B and 6C), the sensing region is positioned at the apex of the radius. When surrounding tissue contracts as it heals, the radius serves to optimize the forces 84 exerted down onto the curved surface, especially the forces in the lateral directions 86, to keep the tissue uniformly in contact with the surface and to produce a thinner foreign body capsule. The curvature ensures that the head is resting against the tissue and that when tissue contraction occurs, forces are generated downward on the head so that the tissue attachment is maintained. It may be noted that the downward forces bring the tissue into contact with porous biointerface materials used for ingrowth-mediated attachment and for biointerface optimization, such as described in more detail with reference to FIGS. 8A to 8B.

Sensing Membrane

In preferred embodiments, the sensing membrane is constructed of two or more domains and is disposed adjacent to the electroactive surfaces of the sensing region 16. The sensing membrane provides functional domains that enable measurement of the analyte at the electroactive surfaces. For example, the sensing membrane includes an enzyme, which catalyzes the reaction of the analyte being measured with a co-reactant (for example, glucose and oxygen) in order to produce a species that in turn generates a current value at the working electrode, such as described in more detail above in the Overview section. The sensing membrane can be formed from one or more distinct layers and can comprise the same or different materials.

In some embodiments, the sensing membrane 88 includes an enzyme, for example, glucose oxidase, and covers the electrolyte phase. In one embodiment, the sensing membrane 88 generally includes a resistance domain 90 most distal from the electrochemically reactive surfaces, an enzyme domain 92 less distal from the electrochemically reactive surfaces than the resistance domain, and an electrolyte domain 96 adjacent to the electrochemically reactive surfaces. However, it is understood that a sensing membrane modified for other devices, for example, by including fewer or additional domains, is within the scope of the preferred embodiments. Co-pending U.S. patent application Ser. No. 09/916,711, entitled, "SENSOR HEAD FOR USE WITH IMPLANTABLE DEVICES" and U.S. patent application Ser. No. 10/153,356 entitled, "TECHNIQUES TO IMPROVE POLYURETHANE MEMBRANES FOR IMPLANTABLE GLUCOSE SENSORS," which are incorporated herein by reference in their entirety, describe membranes that can be used in the preferred embodiments. It is noted that in some embodiments, the sensing membrane 88 may additionally include an interference domain 94 that limits some interfering species; such as described in the above-cited co-pending patent application. Co-pending U.S. patent application Ser. No. 10/695,636, entitled, "SILICONE COMPOSITION FOR BIOCOMPATIBLE MEMBRANE" also describes membranes that may be used for the sensing membrane of the preferred embodiments, and is incorporated herein by reference in its entirety.

In some embodiments, the domains of the sensing membrane are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene difluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers, or the like.

Figure 7A:
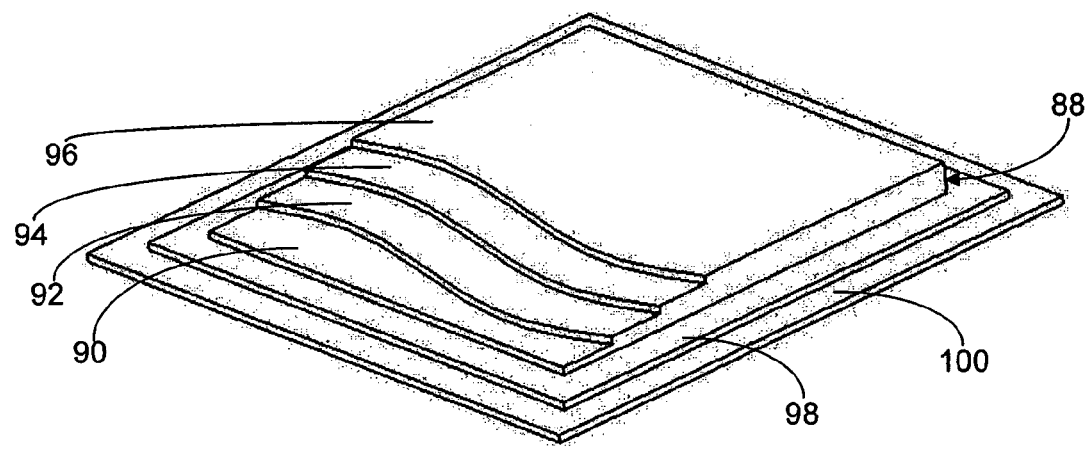
FIG. 7A is an illustration that represents a method of forming the sensing membrane of the preferred embodiments.
Figure 7B:
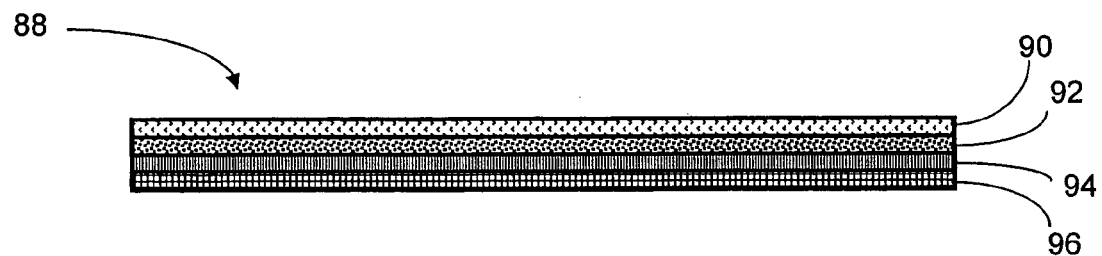
FIG. 7B is a schematic side view of the sensing membrane in one embodiment.

FIG. 7A is an illustration that represents a method of forming the sensing membrane in one embodiment. FIG. 7B is a schematic side view of the sensing membrane in one embodiment. In this embodiment, the sensing membrane 88 includes a resistance domain 90, an enzyme domain 92, an interference domain 94, and an electrolyte domain 96. Preferably, the domains are serially cast upon a liner 98, all of which are formed on a supporting platform 100; however alternative embodiments may form the membrane domains directly on the sensing region 16, for example, by spin-, spray-, or dip-coating.

Referring now to the function of the resistance domain 90, it is noted that there exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based sensor employing oxygen as cofactor should be supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The resistance domain 90 includes a semipermeable membrane that controls the flux of oxygen and glucose to the underlying enzyme domain 92, preferably rendering oxygen in a non-rate-limiting excess. As a result, the upper limit of linearity of glucose measurement is extended to a much higher value than that which is achieved without the resistance domain. In one embodiment, the resistance domain 90 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In some alternative embodiments, a lower ratio of oxygen-to-glucose may be sufficient to provide excess oxygen by using an oxygen antenna domain (for example, a silicone or fluorocarbon based material or domain) to enhance the supply/transport of oxygen to the enzyme domain. In other words, if more oxygen is supplied to the enzyme, then more glucose may also be supplied to the enzyme without creating an oxygen rate-limiting excess. In some alternative embodiments, the resistance domain is formed from a silicone composition, such as described in copending U.S. application Ser. No. 10/685,636 filed Oct. 28, 2003 and entitled, "SILICONE COMPOSITION FOR BIOCOMPATIBLE MEMBRANE," which is incorporated herein by reference in its entirety.

In one preferred embodiment, the resistance layer includes a homogenous polyurethane membrane with both hydrophilic and hydrophobic regions to control the diffusion of glucose and oxygen to an analyte sensor, the membrane being fabricated easily and reproducibly from commercially available materials.

In the preferred embodiment, the hydrophobic polymer component is a polyurethane. In a most preferred embodiment, the polyurethane is polyetherurethaneurea. A polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from 4 to 8 methylene units. Diisocyanates containing cycloaliphatic moieties may also be useful in the preparation of the polymer and copolymer components of the membrane of the present invention. The material that forms the basis of the hydrophobic matrix of the resistance domain may be any of those known in the art as appropriate for use as membranes in sensor devices and having sufficient permeability to allow relevant compounds to pass through it, for example, to allow an oxygen molecule to pass through the membrane from the sample under examination in order to reach the active enzyme or electrochemical electrodes. Examples of materials which may be used to make a non-polyurethane type membrane include vinyl polymers, polyethers, polyesters, polyamides, inorganic polymers such as polysiloxanes and polycarbosiloxanes, natural polymers such as cellulosic and protein based materials and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portion of the copolymer is thermodynamically driven to separate from the hydrophobic portions of the copolymer and the hydrophobic polymer component. The 20% polyethylene oxide based soft segment portion of the copolymer used to form the final blend controls the water pick-up and subsequent glucose permeability of the membrane of the preferred embodiments.

The preferred embodiments additionally provide a method for preparing the resistance domain, which provides a homogeneous and uniform structure. The homogeneous, uniform structure is advantageous in order to ensure that glucose traversing through the resistance domain adequately reaches the electroactive surfaces of the electrode system, which is described in more detail with reference to co-pending U.S. patent application Ser. No. 09/916,711 filed Jul. 27, 2001, entitled "SENSOR HEAD FOR USE WITH IMPLANTABLE DEVICE," and U.S. patent application Ser. No. 10/153,356, entitled, "TECHNIQUES TO IMPROVE POLYURETHANE MEMBRANES FOR IMPLANTABLE GLUCOSE SENSORS," both of which are incorporated herein by reference in their entirety.

The preferred method of casting the resistance domain 90 includes the steps of: (a) forming a solvent solution of a hydrophilic polymer and a hydrophobic polymer; (b) maintaining the composition at a temperature sufficient to maintain the hydrophobic polymer and the hydrophilic polymer substantially soluble; (c) applying the composition at the temperature to a liner 98 to form a film thereon; and (d) permitting the solvent to evaporate from the resultant film to form the membrane.

In the preferred embodiments, the composition is applied to a liner 98, for example, an uncoated Polyethylene Terephthalate (PET), which provides low risk of variability and contamination, for example, in contrast to a coated liner. It is noted that a membrane cured on uncoated PET can be easily removed after 1-hour hydration in room temperature PBS. In some alternative embodiments, other liners and release layers may be used. The platform 100 provides a support for casting and may be for example, the base of a drawdown machine, or the like. While not wishing to be bound by theory, it is believed that the sensing membranes of the preferred embodiments are more consistently produced by casting individual layers serially rather than using a continuous web coating machine, which will be described in more detail throughout the description.

In one embodiment, the forming step includes forming a mixture or a blend of material for the resistance domain. As described above, in preferred embodiments, the first polymer is a polyurethane and the second polymer is a polyurethane comprising a polyethylene oxide. In general, the second polymer may be a random or ordered block copolymer.

The blend is heated substantially above room temperature in order to mix the hydrophilic and hydrophobic components with each other and the solvent. In one embodiment, the composition of the blend of the hydrophilic polymer and the hydrophobic polymer is heated to a temperature of at least about 70° C. for a predetermined time period (for example, at least about 24 hours, preferably at least about 44 hours) to ensure the first and second polymers are substantially intermixed. One skilled in the art appreciates that the level of heating is dependent upon the relative miscibility of the polymer components and may be adjusted accordingly.

The preferred embodiments cure the coated film formed on the liner 98 to dry at an elevated temperature. Additionally, the temperature is ramped up during the curing process. In one embodiment, the coated film is placed in an oven wherein the temperature is ramped at a preferred ramp rate of within the range of 3° C./minute and 12° C./minute, more preferably 7° C. per minute from a first elevated temperature to a second elevated temperature. Preferably, the first elevated temperature is between about 60° C. and 100° C., more preferably about 80° C. Preferably, the second elevated temperature is at least about 100° C. The elevated temperature serves to drive the solvent from the coating as quickly as possible. Ramping of the temperature serves to provide more uniformity and fewer defects in the hydrophobic and hydrophilic domain structures as they cure. While not wishing to be bound by theory, it is believed that elevating the temperature prior to coating and ramping up the temperature during curing inhibits the hydrophilic and hydrophobic portions of the membrane from segregating and forming large undesired structures. Membranes prepared in this way have been shown to provide accurate sensor operation at temperatures from about 30° C. to about 45° C. for a period of time exceeding about 30 days to exceeding about 6 months.

In one experiment, a plurality of resistance membranes (n=5) were prepared as described above, including heating at about 80° C. for greater than 24 hours prior to curing. In this experiment, each of the membranes was cured in an oven where the temperature was ramped at a rate of about 3° C./min., 5° C./min., or 7° C./min. All of the membranes provided sufficient glucose permeability when tested (about 1.24 nA/mg/dL to 2.5 nA/mg/dL). It was noted that the rate of permeability of glucose (namely, the sensitivity) through the membrane decreased as a function of temperature ramp rate. Namely, the glucose permeability of a membrane decreased as the ramp rate used to cure that membrane increased, with a correlation ($R^2$) of 0.58. While not wishing to be bound by theory it is believed that the glucose permeability can be optimized for a variety of design requirements by altering the ramp rate at which the resistance membrane is cured.

In preferred embodiments, the thickness of the resistance domain is from about 10 microns or less to about 200 microns or more. In more preferred embodiments, the thickness of the resistance domain is from about 15, 20, 25, 30, or 35 microns to about 65, 70, 75, 80, 85, 90, 95, or 100 microns. In more preferred embodiments, the thickness of the resistance domain is from about 30 or 35 microns to about 40 or 45 microns.

In the preferred embodiments, the enzyme domain 92 provides a catalyst to catalyze the reaction of the analyte and its co-reactant, as described in more detail above. Preferably, the enzyme domain includes glucose oxidase, however other oxidases, for example, galactose oxidase or uricase, may be used.

For an enzyme-based electrochemical glucose sensor to perform well, the sensor's response must neither be limited by enzyme activity nor cofactor concentration. Because enzymes, including glucose oxidase, are subject to deactivation as a function of time even in ambient conditions, this behavior needs to be accounted for in constructing sensors for long-term use. Preferably, the enzyme domain is constructed of aqueous dispersions of colloidal polyurethane polymers including the enzyme. However, some alternative embodiments construct the enzyme domain from an oxygen antenna material, for example, silicone or fluorocarbons in order to provide a supply of excess oxygen during transient ischemia. Preferably, the enzyme is immobilized within the domain as is appreciated by one skilled in the art. Preferably, the domain is coated onto the resistance domain using casting techniques for a coating thickness between about 2.5 microns and about 22 microns, preferably about 15 microns.

In the preferred embodiments, an interference domain 94 is provided to allow analytes and other substances that are to be measured by the electrodes to pass through, while preventing passage of other substances, including potentially interfering substances. In one embodiment, the interference domain limits the diffusion of hydrophilic species, such as ascorbate, and large molecular weight species. Preferably, the interference domain is constructed of polyurethane, however other materials may be used.

Casting of the interference domain may be important in that an interference layer that is too thick may block desired species from being measured, while an interference domain that is too thin may not block appropriate interfering species. The interference domain has a preferred thickness of not more than about 5 microns, more preferably not less than about 0.1 microns, and not more than about 5 microns and, most preferably, not less than about 0.5 microns, and not more than about 3 microns.

Because of the extremely thin nature of the interference domain, consistently functional interference layers have conventionally been difficult to manufacture due to their susceptibility to variances in the underlying domain (for example, enzyme domain) and casting processes. In order to obtain an interference domain with appropriate and constant thickness, the interference solution of the preferred embodiments is cast by applying a sufficiently diluted interference solution and drawing down at a sufficiently fast speed in order to maintain a constant viscosity of the liquid film with minimal solvent evaporation.

In one embodiment, a "sufficiently diluted interference solution" includes a ratio of about 5 wt. % polymer to about 95 wt. % solvent. However, a ratio of about 1 to 10 wt. % polymer to about 90 to 99 wt. % solvent may be used. Additionally, due to the volatility of solvents used for in the interference solution (for example, solvents with a boiling point slightly greater than room temperature (about 5 to 15° C.)), a sufficiently fast casting speed is advantageous to avoid invariabilities (for example, film thickness inhomogeneities) due to evaporation during casting. In one embodiment, the liquid film is drawn down at a speed of about 8 to about 15 inches/second, and preferably about 11.5 inches/second. While not wishing to be bound by theory, optimization of the solvent dilution and draw down speed limits solvent evaporation and viscosity buildup, which enables a very thin but constant interference domain. Variability in the interference domain has been discovered by the inventors to be a significant contributor in the variability of sensor function.

In preferred embodiments, an electrolyte domain 96 is provided to ensure an electrochemical reaction occurs at the electroactive surfaces. Preferably, the electrolyte domain includes a semipermeable coating that maintains hydrophilicity at the electrochemically reactive surfaces of the sensor interface. The electrolyte domain enhances the stability of the interference domain 94 by protecting and supporting the material that makes up the interference domain. The electrolyte domain also assists in stabilizing the operation of the sensor by overcoming electrode start-up problems and drifting problems caused by inadequate electrolyte. The buffered electrolyte solution contained in the electrolyte domain also protects against pH-mediated damage that may result from the formation of a large pH gradient between the substantially hydrophobic interference domain and the electrodes due to the electrochemical activity of the electrodes.

In one embodiment, the electrolyte domain 96 includes a flexible, water-swellable, substantially solid hydrogel film having a "dry film" thickness of from about 5 microns to about 15 microns, more preferably from about 3, 3.5, 4, 4.5, 5, or 5.5 to about 6, 6.5, 7, 7.5, 8, 8.5, 9, 9.5, 10, 10.5, 11, 11.5, or 12 microns. "Dry film" thickness refers to the thickness of a cured film cast from a coating formulation onto the surface of the membrane by standard coating techniques.

In some embodiments, the electrolyte domain is formed of a curable mixture of a urethane polymer and a hydrophilic film-forming polymer. Particularly preferred coatings are formed of a polyurethane polymer having anionic carboxylate functional groups and non-ionic hydrophilic polyether segments, which is crosslinked in the presence of polyvinylpyrrolidone and cured at a moderate temperature of about 50° C. Underlying the electrolyte domain is an electrolyte phase is a free-fluid phase including a solution containing at least one compound, typically a soluble chloride salt, which conducts electric current. In one embodiment wherein the biocompatible membrane is used with an analyte sensor such as is described herein, the electrolyte phase flows over the electrodes and is in contact with the electrolyte domain. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

Underlying the electrolyte domain is an electrolyte phase, which is a free-fluid phase including a solution containing at least one compound, typically a soluble chloride salt, which conducts electric current. In one embodiment wherein the biocompatible membrane is used with an analyte sensor such as is described herein, the electrolyte phase flows over the electrodes and is in contact with the electrolyte domain. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

Although the preferred embodiments provide for serially casting of the sensing membrane, alternative embodiments may utilize known thin or thick film fabrication techniques known in the art (for example, continuous web or deposition techniques). In various embodiments, any of these domains may be omitted, altered, substituted for, and/or incorporated together without departing from the spirit of the preferred embodiments. For example, the interference domain may not be necessary in some embodiments, such as when the analyte sensor is designed to reduce interfering species using electrochemical techniques. Additionally, the various domains may be combined in function; for example, one discrete layer may function both as the resistance and enzyme domain. In another such example, an oxygen antenna domain may be individually formed from an oxygen reserving material (for example, silicone or fluorocarbon), or may be combined with some or all of the biointerface membrane. Additionally, the sensing membrane may be combined with some or all of the domains of the biointerface membrane, such as the bioprotective (cell impermeable) domain, which is described in more detail below.

Biointerface Membrane

The preferred embodiments provide a biointerface membrane disposed more distal to the electroactive surface than the sensing membrane. Preferably, the biointerface membrane 106 supports tissue ingrowth, serves to interfere with the formation of a barrier cell layer, and protects the sensitive regions of the device from host inflammatory response. In some embodiments, the biointerface membrane is composed of one or more domains.

In one embodiment, the biointerface membrane 106 generally includes a cell disruptive domain 108 most distal from the electrochemically reactive surfaces and a cell impermeable domain 110 less distal from the electrochemically reactive surfaces than the cell disruptive domain 108. The cell disruptive domain 108 comprises an architecture, including a cavity size, configuration, and overall thickness that encourages vascular tissue ingrowth and disrupts barrier cell formation in vivo, and a cell impermeable domain that comprises a cell impermeable layer that is resistant to cellular attachment and has a robust interface that inhibits attachment of barrier cells and delamination of the domains.

Figure 8A:
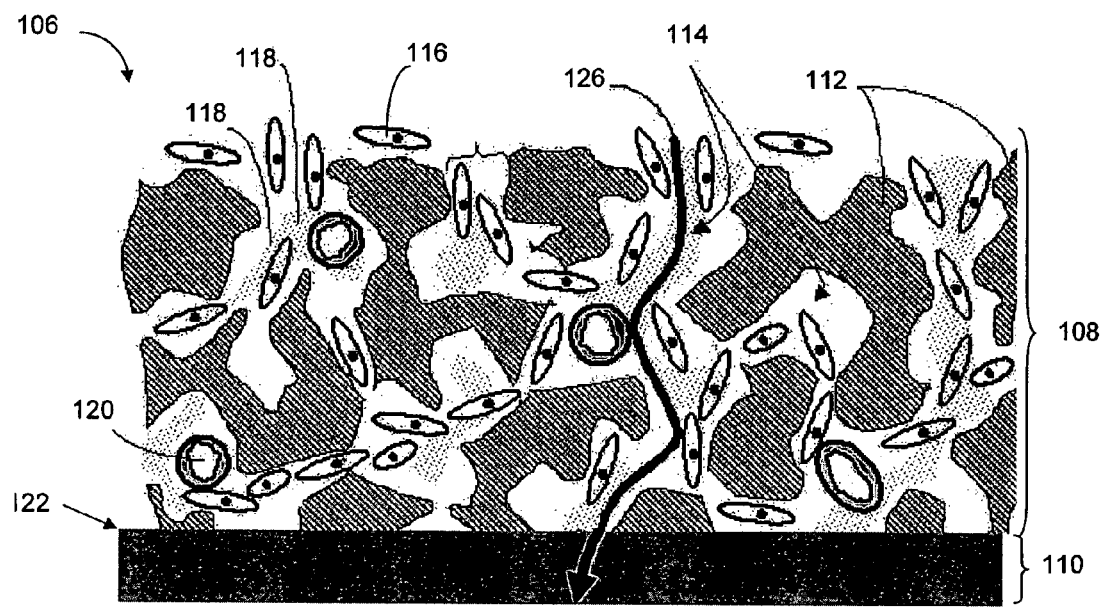
FIG. 8A is a cross-sectional schematic view of a biointerface membrane in vivo in one embodiment, wherein the membrane comprises a cell disruptive domain and cell impermeable domain.

FIG. 8A is a cross-sectional schematic view of a membrane 106 in vivo in one embodiment, wherein the membrane comprises a cell disruptive domain 108 and cell impermeable domain 110. The architecture of the membrane 106 provides a robust long-term implantable membrane that allows the transport of analytes through vascularized tissue ingrowth without the formation of a barrier cell layer.

The cell disruptive domain 108 comprises a solid portion 112 and a plurality of interconnected three-dimensional cavities 114 formed therein. The cavities 114 have sufficient size and structure to allow invasive cells, such as fibroblasts 116, fibrous matrix 118, and blood vessels 120 to completely enter into the apertures 40 that define the entryway into each cavity 114, and to pass through the interconnected cavities toward the interface 122 between the cell disruptive and cell impermeable domains (cells and blood vessels are disproportionately large in the illustration). The cavities 114 comprise an architecture that encourages the ingrowth of vascular tissue in vivo as indicated by the blood vessels 120 formed throughout the cavities. Because of the vascularization within the cavities, solutes 126 (for example, oxygen, glucose and other analytes) can pass through the first domain with relative ease and/or the diffusion distance (i.e., distance that the glucose diffuses) can be reduced.

The cell impermeable domain 110 comprises a cell impermeable layer that may be resistant to cellular attachment and thus provides another mechanism for resisting barrier cell layer formation (indicated in FIG. 8A by few macrophages and/or giant cells at the interface 122 between the domains). Because the cell impermeable domain 110 is resistant to cellular attachment and barrier cell layer formation, the transport of solutes such as described above can also pass through with relative ease without blockage by barrier cells as seen in the prior art.

Figure 8B:
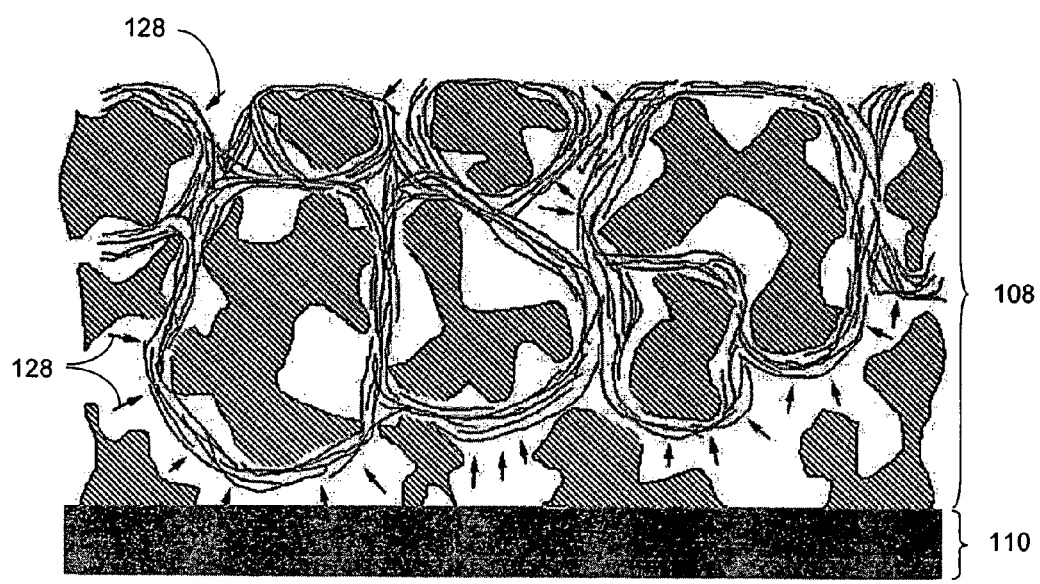
FIG. 8B is an illustration of the membrane of FIG. 8A, showing contractile forces caused by the fibrous tissue of the FBR.

Reference is now made to FIG. 8B, which is an illustration of the membrane of FIG. 8A, showing contractile force lines caused by the fibrous tissue (for example, from the fibroblasts and fibrous matrix) of the FBR. Particularly, the architecture of the cell disruptive domain 108, including the cavity interconnectivity and multiple-cavity depth, (i.e., two or more cavities in three dimensions throughout a substantial portion of the first domain) can affect the tissue contracture that typically occurs around a foreign body.

It is noted that a contraction of the FBC around the device as a whole produces downward forces on the device, such as shown in FIGS. 6B and 6C, which can be helpful in reducing motion artifacts such as described with reference to copending U.S. patent application Ser. No. 10/646,333 entitled "OPTIMIZED SENSOR GEOMETRY FOR AN IMPLANTABLE GLUCOSE SENSOR," which is incorporated herein in its entirety by reference. However, the architecture of the first domain described herein, including the interconnected cavities and solid portion, are advantageous because the contractile forces caused by the downward tissue contracture that can otherwise cause cells to flatten against the device and occlude the transport of analytes, is instead translated to, disrupted by, and/or counteracted by the forces 128 that contract around the solid portions 112 (for example, throughout the interconnected cavities 114) away from the device. That is, the architecture of the solid portions 112 and cavities 114 of the cell disruptive domain cause contractile forces 128 to disperse away from the interface between the cell disruptive domain 108 and cell impermeable domain 110. Without the organized contracture of fibrous tissue toward the tissue-device interface typically found in a FBC, macrophages and foreign body giant cells substantially do not form a monolayer of cohesive cells (i.e., barrier cell layer) and therefore the transport of molecules across the second domain and/or membrane is substantially not blocked (indicated by free transport of analytes 126 through the domains in FIG. 8A).

Co-pending U.S. patent application Ser. No. 09/916,386, entitled, "MEMBRANE FOR USE WITH IMPLANTABLE DEVICES," U.S. patent application Ser. No. 10/647,065, entitled, "POROUS MEMBRANES FOR USE WITH IMPLANTABLE DEVICES," and U.S. Provisional Patent Application 60/544,722, entitled "BIOINTERFACE WITH INTEGRATED MACRO- AND MICRO-ARCHITECTURES," describe biointerface membranes that may be used in conjunction with the preferred embodiments, and are incorporated herein by reference in their entirety.

The cell disruptive and cell impermeable domains can be formed from materials such as silicone, polytetrafluoroethylene, polyethylene-co-tetrafluoroethylene, polyolefin, polyester, polycarbonate, biostable, homopolymers, copolymers, terpolymers of polyurethanes, polypropylene (PP), polyvinylchloride (PVC), polyvinyl alcohol (PVA), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers.

The cell disruptive domain and cell impermeable domain of the biocompatible membrane can be formed together as one unitary structure. Alternatively, the cell disruptive and cell impermeable domains of the biocompatible membrane can be formed as two layers mechanically or chemically bonded together. In yet another embodiment, the cell impermeable domain is chemically or mechanically attached to the sensing membrane. In some embodiments, the bioprotective function of the cell impermeable domain is inherent in the structure of the sensing membrane and therefore no discrete cell impermeable domain is required.

Membrane Attachment

Figure 9A:
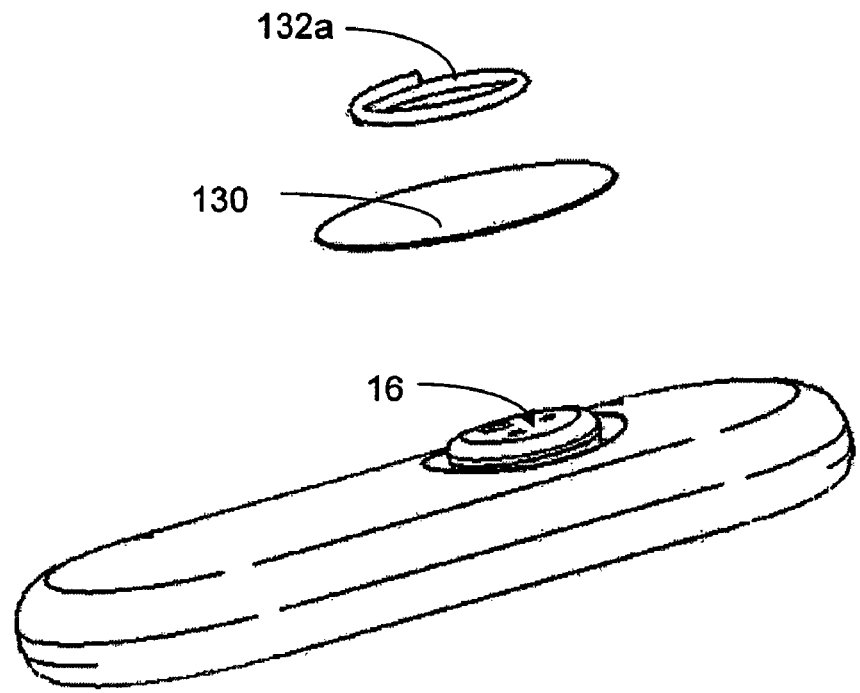
FIG. 9A is an exploded perspective view of the analyte sensor prior to membrane attachment.
Figure 9B:
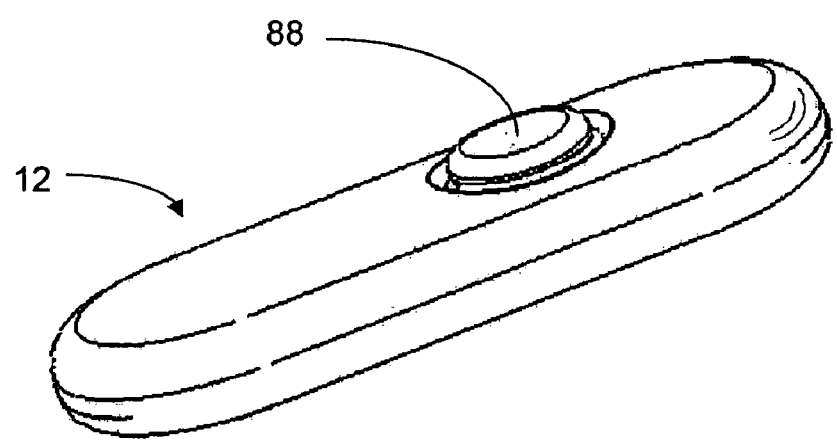
FIG. 9B is a perspective view of the analyte sensor after membrane systems and methods.

FIG. 9A is an exploded perspective view of the analyte sensor prior to membrane attachment. FIG. 9B is a perspective view of the analyte sensor after membrane attachment. In preferred embodiments, the membrane 130 is attached to the sensing region 16 of the sensor 12 via a mechanical fastener 132, which in the illustrated embodiment of FIGS. 9A and 9B is a clip 132a.

In some embodiments, both the sensing membrane 88 and biointerface membranes 106 are placed to together and the membrane 130 attached to the sensing region 16 via the mechanical fastener 132. In some alternative embodiments, some portion of the biointerface membrane 106 (for example, the cell disruptive domain 108) may be attached without the mechanical fastener 132. In preferred embodiments, the cell impermeable domain 110 is formed separately from the cell disruptive domain 108 and the cell impermeable domain 110 is attached to the sensing region 16 simultaneously with the sensing membrane 88 via the mechanical fastener 132.

In attaching the membrane 130 to the sensing region 16, it is desirable to avoid over-stretching of the membranes, which may create cracks or fissures that allows cells to penetrate to the sensing membrane. It is also desirable to avoid lack of tension in the membrane, which may create excess spacing under the membrane (for example, bubbles), which distorts device function.

The preferred embodiments provide an advantageous method of attachment, wherein the membrane 130 is applied to the sensing region 16 with appropriate tension to optimize sensor performance; namely, by minimizing tearing or excess spacing. Preferably, the membranes are hydrated prior to attachment, which minimizes or avoids distortion of the membrane. Preferably, the hydrated sensing membrane 88 is first placed over the sensing region 16 (after being released from the liner 98). Next, the cell impermeable domain 110 is placed over the sensing membrane 88, ensuring no wrinkles or bubbles exist (in embodiments wherein the cell disruptive domain is attached to the sensing region under the mechanical fastener 132, the cell disruptive domain would also be disposed over the cell impermeable domain). Finally the mechanical fastener is applied over the sensing region 16 and preferably into a groove surrounding the sensing region 16. In general, the mechanical fastener 132 (for example, a metal or plastic O-ring in FIGS. 9A and 9B) is designed provide sufficient tension to the combined membrane 130 in order to maintain tautness and provide a seal that prevents cellular ingrowth. Advantageously, this combined membrane 130 may be unattached, and a new membrane 130 attached as necessary, making the system and method reusable and cost-effective.

FIGS. 9C to 9H are exploded and collapsed perspective views of alternative membrane attachment embodiments. In each embodiment, the mechanical fastener 132 is provided for attaching the membrane 130 to the sensing region 16 substantially as described above. It is noted that although chemical attachment techniques (such as an adhesive or solvent) may be used to enhance the mechanical attachment, it is believed that the preferred mechanical attachments provide appropriate tension to enable a sufficient seal of the membrane 130 on the sensing region 16 without chemically altering the membrane 130. Additionally, mechanical attachment of the membrane makes the system and method reusable and cost-effective as described above.

Figure 9C:
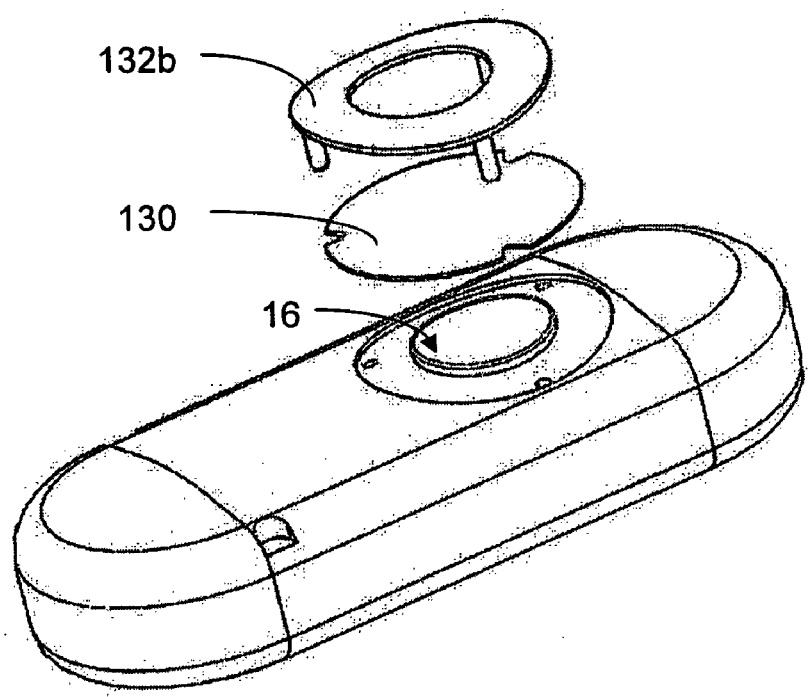
FIGS. 9C to 9H are exploded and collapsed perspective views of a variety of alternative embodiments that utilize alternative membrane attachment techniques.
Figure 9D:
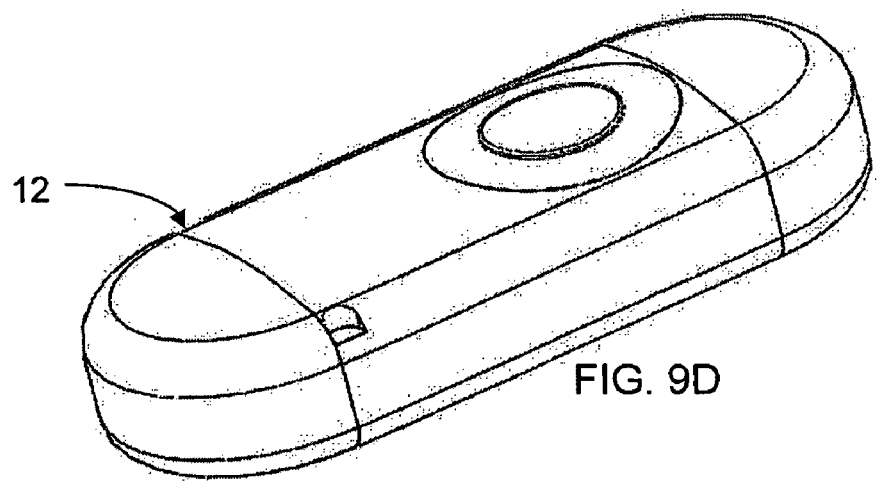

FIGS. 9C and 9D are perspective views of one alternative embodiment, wherein the mechanical fastener 132 is a metal or plastic disc 132b adapted to be press- or snap-fit into the device body 12. Namely, the disc 132b has a plurality of legs, which are designed to securely fit into holes in the sensor body 12. The disc 132b has a central aperture sized and arranged to provide access to the sensing region 16 of the device so that analytes may pass therethrough. The membrane 130 may be any appropriate configuration, such as described in more detail above. The membrane attachment of FIGS. 9C and 9D is advantageous for the reasons described above and further may enable a lower profile of the sensing region 16 as compared to the embodiment of FIGS. 9A and 9B, for example. While not wishing to be bound by theory, it is believed that design optimization (for example, reduction of size, mass, and/or profile) of the device enables a more discrete and secure implantation than a larger device, and is believed to reduce macro-motion of the device induced by the patient (for example, fiddling) and micro-motion caused by movement of the device (for example, which produces chronic inflammation) within the subcutaneous pocket, and thereby improves overall device performance.

Figure 9E:
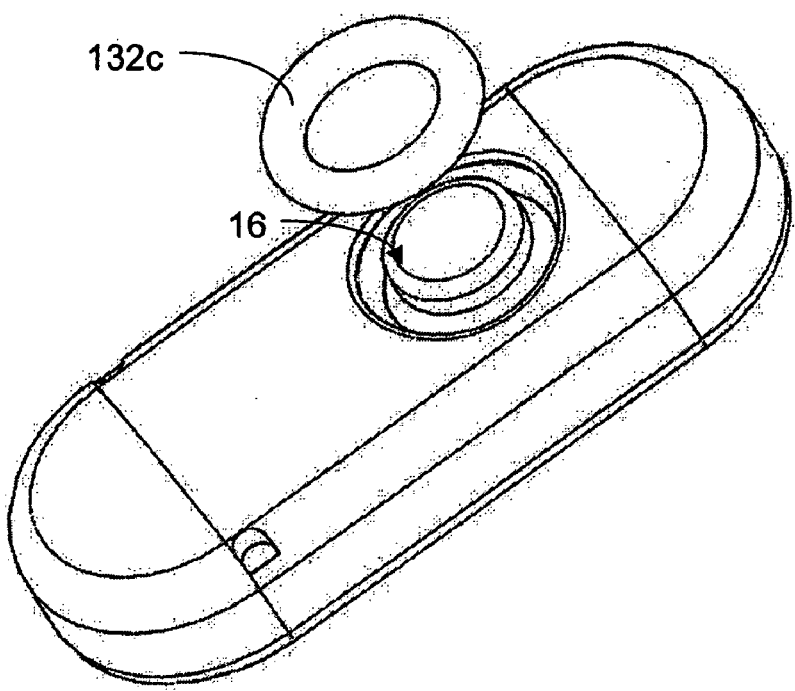
Figure 9F:
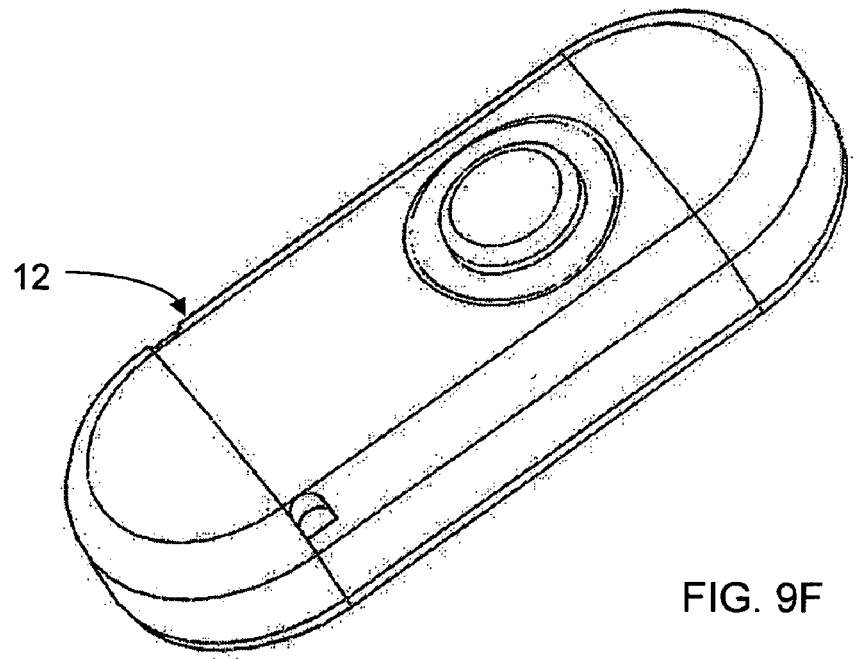

FIGS. 9E and 9F are perspective views of another alternative embodiment, wherein the mechanical fastener 132 is a metal or plastic, ring or donut 132c adapted to be press- or snap-fit into the device body 12. In this embodiment, the donut 132c is designed to substantially fill the aperture surrounding the sensing region 16. While this embodiment is similar to that of FIGS. 9A and 9B, the sizing of the donut to substantially fill the aperture provides an optimized seal of the membrane edges and device body, and reduces opportunity for cellular ingrowth.

Figure 9G:
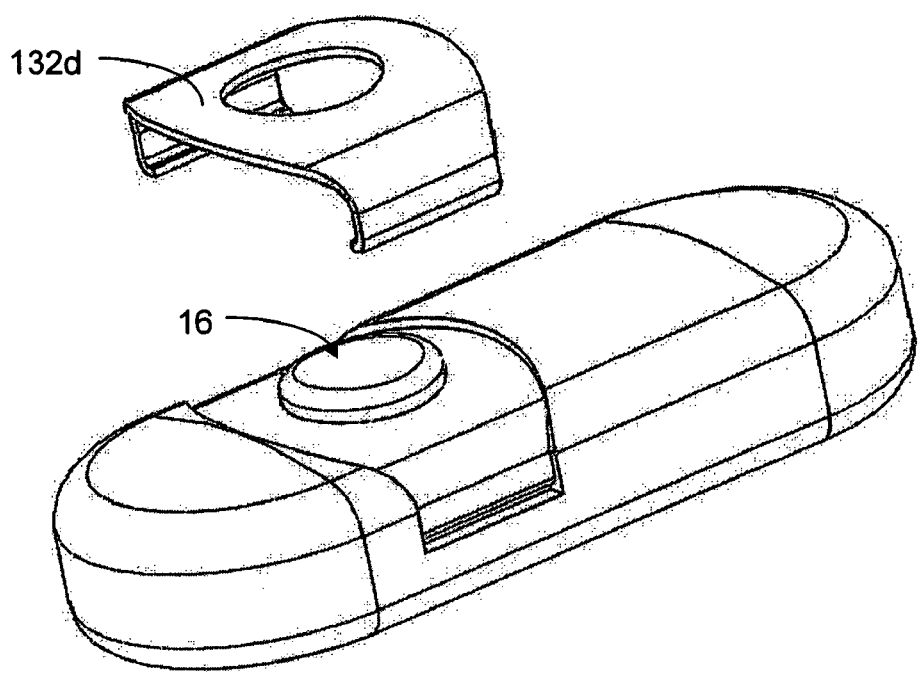
Figure 9H:
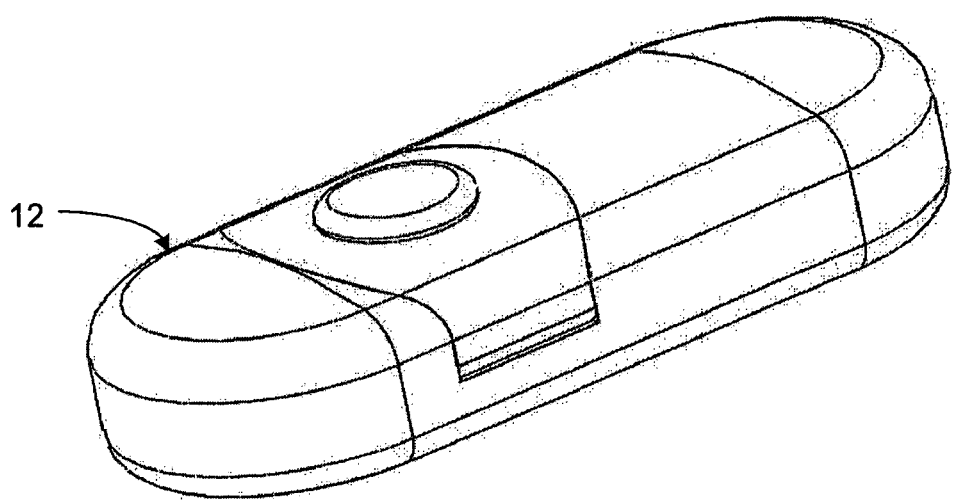

FIGS. 9G and 9H are perspective views of yet another alternative embodiment, wherein the mechanical fastener 132 is a metal or plastic clip 132d adapted to be press- or snap-fit into sides of the device body 12. This embodiment provides advantages of a low profile body with a substantially flat, smooth upper surface of the device body. It is believed the a smoother upper surface provides less opportunity for inflammation proximal the sensing region in vivo, such a described in co-pending U.S. patent application Ser. No. 10/646,333, which is incorporated herein by reference in its entirety.

Long- and Short-Term Anchoring

The final step in the assembly of the implantable sensor includes attaching the outermost layers, which serve as the device-tissue interface and may play a critical role in device stabilization in vivo. The preferred embodiments may be designed with short- and/or long-term anchoring systems and methods in order to ensure stabilization of the device in vivo. As discussed above and in more detail below, stabilization of the device in the subcutaneous tissue is believed to impact the performance of the sensor short- and long-term. In one preferred embodiment, the sensor comprises a short-term anchoring component configured to anchor the sensor to the tissue and thereby minimize motion-related damage at the device-tissue interface, which is believed to cause local inflammation and poor wound healing during the initial tissue ingrowth phase. Additionally, the preferred embodiments comprise a long-term anchoring component on the sensor to ensure long-term stabilization of the sensor in the subcutaneous pocket. Although both long- and short-term anchoring are preferred, some embodiments may utilize only one or the other, for example, when the sensor is sufficiently miniaturized such that the sensor body substantially "floats" within the subcutaneous space, or when a precise pocket forming or implantation technique is utilized, at least one of short- and long-term anchoring may not be required for sufficient sensor performance.

Figure 10A:
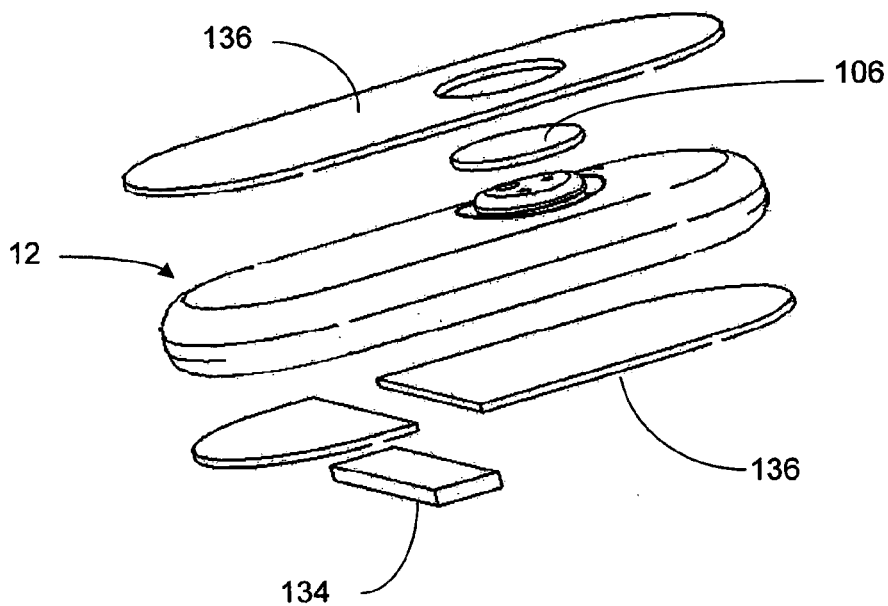
FIG. 10A is an exploded perspective view of a sensor, illustrating the tissue-facing components of the sensor prior to attachment.
Figure 10B:
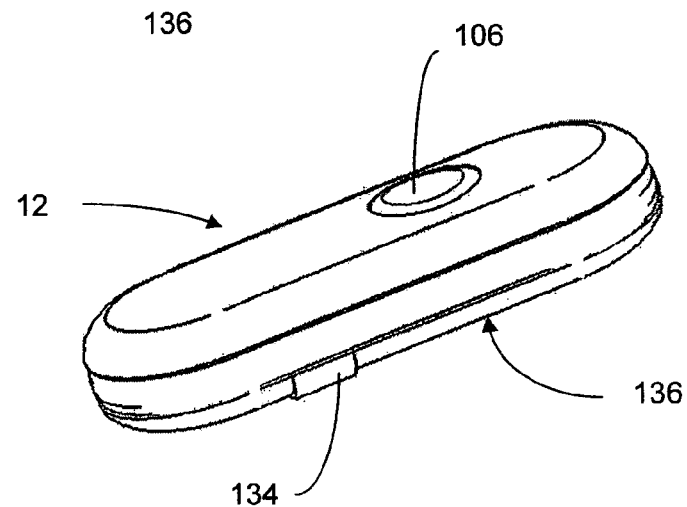
FIG. 10B is a perspective view of the assembled analyte sensor, including the tissue-facing components attached thereto.
Figure 10C:
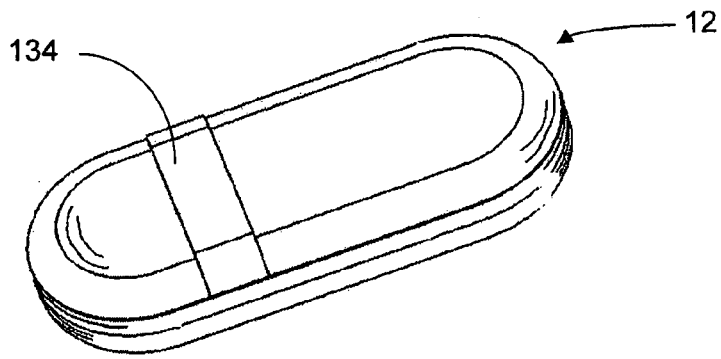
FIG. 10C is a perspective view of the non-sensing side of the assembled analyte sensor, showing a short-term anchoring device in one embodiment.

FIG. 10A is an exploded perspective view of the machined sensor geometry of FIG. 6 and the tissue-facing components of the sensor. FIG. 10B is a perspective view of the assembled analyte sensor, including the tissue-facing components attached thereto. FIG. 10C is a perspective view of the non-sensing side of the assembled analyte sensor, showing a short-term anchoring device in one embodiment.

Referring now to FIG. 10A, the tissue-facing components, including the biointerface membrane 106, which is described in more detail with reference to FIG. 10, a short-term anchoring component 134, and a long-term anchoring component 136 are shown. Each of these components is securely attached to the sensor body as described in more detail below.

A variety of attachment methods are contemplated for attaching the biointerface membrane 106 to the sensor 12, including mechanical attachment (such as under clip 132) and chemical attachment (such as laser welding, ultrasonic welding, solvent welding, or the like). In the preferred embodiments, the biointerface membrane 106, namely the cell disruptive domain 108, is adhered to the sensor body using an adhesive, such as a silicone adhesive, which may be particularly advantageous when the biointerface membrane 106 is formed from a silicone material, for example. It is noted that the silicone adhesive is preferably applied on the circumference of the biointerface membrane 108 to avoid blockage of the interconnected cavities 114 of the cell disruptive domain 108. In one preferred embodiment, the biointerface membrane 106 shown in FIG. 10A represents only a cell disruptive domain 108 because the cell impermeable domain 110 is mechanically attached under clip 132 (FIG. 9).

In the illustrated embodiment, the short-term anchoring component includes a suture strip 134, which is used by a surgeon to immobilize the sensor against the fascia or other substantially tough tissue after insertion, such as described in more detail with reference to FIGS. 12 and 13, below. Alternatively, other short-term anchoring components that may be used include prongs, spines, barbs, wings, hooks, helical surface topography, gradually changing diameter, or the like, which may be disposed on the sensor body. For example, when an oblong or cylindrical type sensor is implanted within the subcutaneous tissue, it may tend to slip along the pocket that was formed during implantation, particularly if some additional space exists within the pocket. This slippage can lead to increased inflammatory response and/or movement of the sensor prior to or during tissue ingrowth. Accordingly, a short-term anchoring component can aid in immobilizing the sensor in place, particularly prior to formation of a mature foreign body capsule.

Generally, short-term anchoring provides a system and method for immobilizing the sensor within the soft tissue during the acute wound-healing phase immediately following the implantation surgery. While not wishing to be bound by theory, it is believed that the short-term anchoring component prevents the sensor from movement within any remaining space in a subcutaneous pocket or space immediately under the incision, thereby minimizing tissue trauma and its associated inflammation and foreign body response. By minimizing tissue trauma, a healthy vascularized tissue bed is more likely to heal within the biointerface membrane, which is believed to optimize analyte transport to the sensing region, such as described in more detail with reference to FIG. 8.

In the illustrated embodiment, the long-term anchoring component 136 is an anchoring material. The term "anchoring material," as used herein, is a broad term and is used in its ordinary sense, including, without limitation, biocompatible material or surface that is non-smooth, and particularly comprises an architecture that supports tissue ingrowth in order to facilitate anchoring of the material into bodily tissue in vivo. Some examples of anchoring materials include polyester, velours, polypropylene cloth, expanded polytetrafluoroethylene, and porous silicone, for example. However, anchoring material may be built into the sensor body, for example, by texturizing the non-sensing region 18 of the analyte sensor 12. In one embodiment, the entire surface of the sensor is covered with an anchoring material to provide for strong attachment to the tissues. In another embodiment, only the sensing side of the sensor incorporates anchoring material, with the other sides of the sensor lacking fibers or porous anchoring structures and instead presenting a very smooth, non-reactive biomaterial surface to prevent attachment to tissue and to support the formation of a thicker capsule.

Other configurations may also be suitable for use in certain embodiments, including configurations with different degrees of surface coverage. For example, from less than about 5, 10, 15, 20, 25, 30, 35, 40, 45, or 50% to more than about 55, 60, 65, 70, 75, 80, 85, 90, or 95% of the surface of the device may be covered with anchoring material. The anchoring material may cover one surface, two surfaces, three surfaces, four surfaces, five surfaces, or six surfaces. The anchoring material may cover only a portion of one or more sides, for example, strips, dots, weaves, fibers, meshes, and other configurations or shapes of anchoring material may cover one or more sides. It may be noted that the optimum amount of anchoring material that may be used for any particular sensor is dependent upon one or more of the following parameters: implantation site (for example, location in the host), surface area, shape, size, geometry, mass, density, volume, surface area-to-volume, surface area-to-density, and surface area-to-mass. For example, a device with a greater density as compared to a device with a lesser density may require more anchoring material.

Generally, long-term anchoring provides a system and method for immobilizing the sensor long-term in vivo, which is believed to reduce or eliminate the effects of chronic movement on the sensor (for example, macro- or micro-motion). Immobilization of the sensor long-term in vivo sustains sensor performance, for example, sensitivity of the sensor to the analyte, at least in part by minimizing the inflammation and associated foreign body response that is known to block analytes from freely diffusing to the sensing region, for example.

Implantation

Sizing Tool

The preferred embodiments employ implantation techniques that exploit the knowledge gained by the inventors in experimentation with implantation techniques. In one study, nineteen glucose sensors were implanted in humans, wherein the sensors were designed with a cylindrical configuration with the sensing region on one end thereof. It was observed that of the nineteen patients participating in the study, acceptable efficacy was observed for only about half. The study is described in more detail with reference to co-pending U.S. Provisional Patent Application 60/460,825. In summary, surgical methods employed in the clinical study entailed making a 1-inch incision, then forming a pocket lateral to the incision by blunt dissection. After placement of the device, a suture was placed by pulling the connective tissue together at the end of the device proximal to the incision. During the first several weeks after implantation of the sensor in the human test subjects, photographs were taken of the wound site and the position of the device was determined tactilely. It was observed that eighteen of the nineteen sensors migrated in a retrograde fashion from the placement site towards the incision site. Thirteen of these devices moved a significant distance, namely, a distance of 1 cm or more (device movement of 0.5 cm or less is not considered to be significant, based on the resolution of the test measurements utilized). While not wishing to be bound by theory, it is believed that the sutures did not hold in the softer, fatty subcutaneous tissues as healing began and wound contracture formed. This permitted the devices to move into the virtual space remaining after the formation of the pocket, and in some cases even permitted the device to migrate into the space immediately under the incision.

Although the sensors of the above-described experiment included layers of porous anchoring materials and biointerface materials that are designed to be ingrown with tissues, especially blood vessels, during the wound-healing period; it is well known in the literature that devices that do not become anchored well in tissues may become encapsulated by a connective tissue scar much more aggressively than devices that are well-anchored in tissues. It is believed that the gross movement of devices that was observed in the clinical study may have in some cases prevented proper ingrowth of tissues. Delayed ingrowth of tissues or lack of ingrowth of tissues may affect device function in a variety of ways, including lack of glucose sensitivity, delayed start-up of glucose tracking, and compromised function after start-up, including low sensitivity and long time lags. In some cases, empty space left behind after sensor movement has filled with scar tissue as determined by histological examination of explanted sensors.

Additionally, it is believed that certain behavioral issues lead to incomplete healing. Complicating factors included "fiddling" behaviors (namely, feeling and moving the sensor under the skin), and the like. These complicating factors were present to some extent in all of the patients, but were less frequent in patients with working sensors. Thus, the inventors attribute at least some sensor performance issue to patient-related movement.

Taken together, the inventors identified likely contributing factors to these performance issues, including: the location of the sensing region in this experiment on the end of the device may have led to problems with healing if the sensor moves in such a way that even a small gap is produced at the end of the sensor; the high profile of the cylindrical geometry is believed to have caused the sensor to have a high profile, which makes it easier to bump the sensor and can lead to the patient touching and feeling the sensor ("fiddling"); and the sensing region can be disrupted easily if pressure is placed on the opposite end of the device because the sensor may act as a lever, for example, and rotational energy can be applied to the sensor, which can also cause disruption of the sensor-tissue interface.

Accordingly, the preferred embodiments employ sensor geometry, short- and/or long-term anchoring, and implantation techniques that are designed to overcome to the shortcomings observed in the previously described experiment. For example, implantation techniques are disclosed that are believed to reduce the likelihood of device migration, and thereby provide optimized immobilization and healthy wound healing in vivo. Anchoring components are disclosed that are believed to substantially immobilize the device, and thereby provide short- and long-term stability with minimized trauma. Sensor geometry is disclosed that reduces fiddling and improves stability due to its low profile and curved surface(s). All of the above advantages improve analyte transport through the sensing region and thereby improve long-term sensor performance.

FIGS. 11A to 11C are views of a pocket sizing tool in one preferred embodiment, which has been designed to aid a surgeon in forming a precisely sized pocket. As described in more detail above, it has been found that when extra space is formed within soft tissue during implantation (for example, an oversized pocket), post-surgical device migration may result, which is believed to result in suboptimal healing of the tissue into the device. Suboptimal wound healing is believed to lead to increased thickness of foreign body capsule formation and increased barrier cell layer formation, which results in poor analyte transport and sensor performance in vivo. Accordingly, a pocket-sizing tool is provided, which may be utilized by the surgeon in precisely forming a subcutaneous pocket.

FIG. 11A is a perspective view of the sizing tool 138 in one preferred embodiment, including a head 140 and a handle 142. FIG. 11B is a side view of the sizing tool 138 showing the offset placement of the handle 142 on the head 140 in one embodiment. FIG. 11C is a top view of the sizing tool 138 showing a curvature substantially similar to that of the sensor body (FIG. 6).

Referring now to the head 140 of the sizing tool, the preferred embodiments configure the head geometry to be slightly smaller than that of the analyte sensor geometry to be inserted in the host. In some preferred embodiments, the head 140a is dimensioned to be slightly smaller than the dimensions of the analyte sensor 12 such that the sensor inserted into the pocket is in compression within the tissue, thereby immobilizing the sensor body within the subcutaneous pocket. In a preferred embodiment, the x, y, and z dimensions of the head 140 of the sizing tool are about 0.8 times the dimensions of the analyte sensor. It is appreciated by one skilled in the art that the dimensions and geometry of the head 140 of the sizing tool 138 will vary depending on the dimensions and geometry of the implantable analyte sensor.

Referring now to the handle 142 of the sizing tool, in this preferred embodiment, the handle is offset from the center of the head. This design is based on a variety of contributing factors. Firstly, the healing within and adjacent to sensing region 16 is more critical and sensitive than the non-sensing region 18 because analyte transport optimally requires a healthy and well-vascularized tissue bed without barrier cell formation adjacent to the sensing region. Therefore, the offset handle may be provided for an incision that is spaced from the location wherein the sensing region of the sensor is to be located after insertion, which is believed to minimize post-surgical trauma surrounding the sensing region. It is further noted that one preferred embodiment provides a short-term anchoring component 134 at a location offset from and diametrically opposed to the sensing region 16 (FIG. 10C). In this way, the sensor is adapted to be inserted with the short-term anchoring component 134 exposed to the surgeon for suturing to the fascia and diametrically disposed from the sensing region to minimize trauma associated with the incision and suturing adjacent the sensing region 16.

In another preferred embodiment, the handle 142 is centrally located on the head, which may be advantageous in for a variety of implantation techniques. For example, when the analyte sensor is implanted within the fatty tissue of a host, equal sizing on each size of the incision may provide for ease and accuracy of precise subcutaneous pocket formation. However, it is noted that the length, width, thickness, and orientation of the handle may be optimized for various implantation sites and may be adapted for patient size, for example. In general, the sizing tool 138 of the preferred embodiments may be any design that aids a surgeon or doctor in forming a pocket in the soft tissue with minimized tissue trauma adjacent to the sensing region 16 and a precisely sized subcutaneous pocket in a host. It is believed that these factors immobilize the sensor and provide an opportunity for a well healed vascularized tissue bed adjacent to the sensing region of the sensor.

Implantation

Technique

The implantable analyte sensor of the preferred embodiments may be implanted in variety of locations, including: subcutaneous, intramuscular, intraperotoneal, intrafascial, axillary region, soft tissue of a body, or the like. Although the preferred embodiments illustrate implantation within the subcutaneous space of the abdominal region, the systems and methods described herein are limited neither to abdominal nor to subcutaneous implantation. One skilled in the art appreciates that these systems and methods may be implemented and/or modified for other implantation sites and may be dependent upon the type, configuration, and dimensions of the analyte sensor.

Figure 12A:
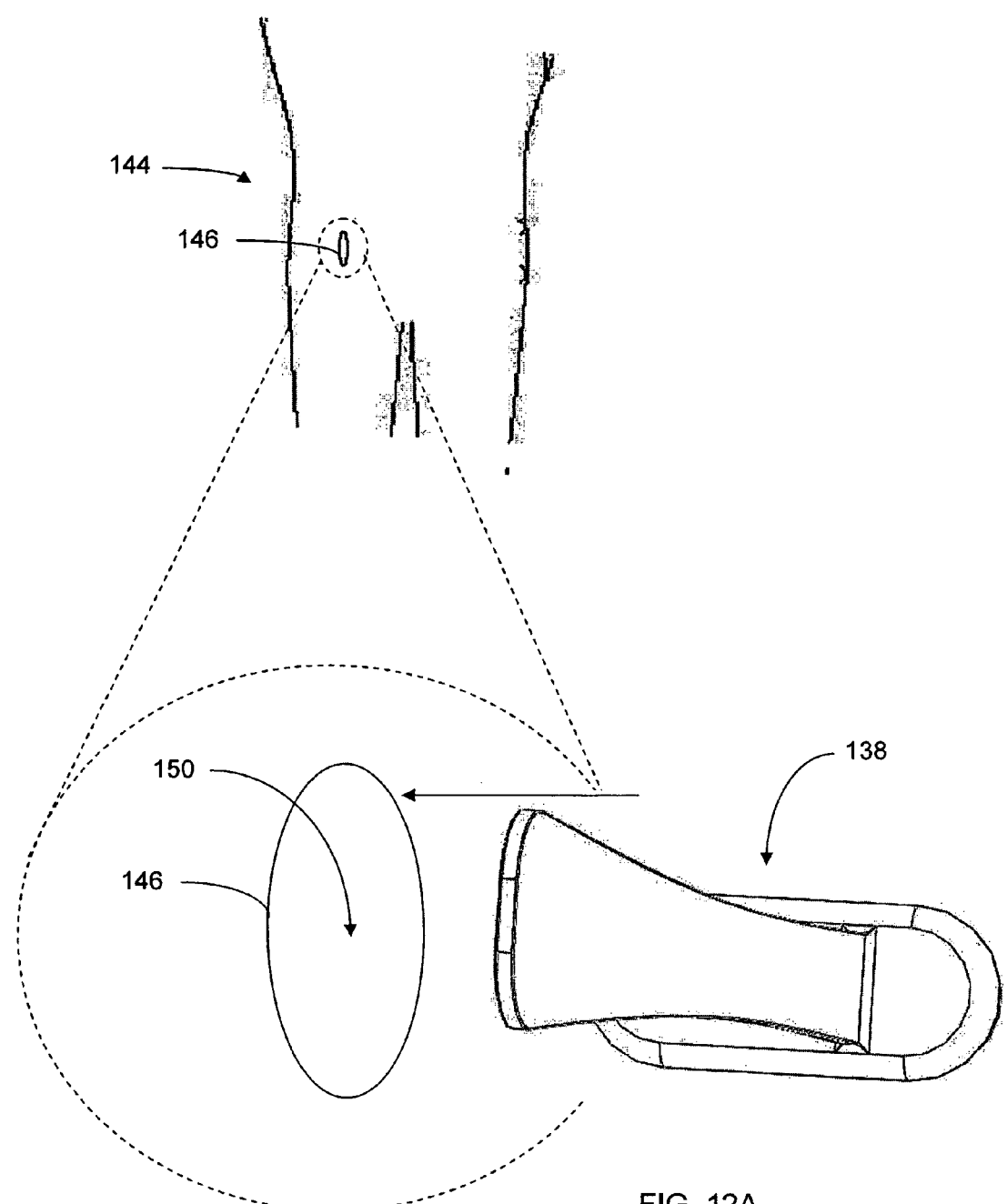
FIG. 12A is a perspective view of an abdominal region of a human, showing an exploded view of the incision and sizing tool that may be used for surgical implantation.

FIG. 12A is a perspective view of the abdominal region 144 of a human, showing the incision 146 and sizing tool 138 that may be used for surgical implantation. In this embodiment, a skin incision 146 is made through to the lower plane of the abdominal subcutaneous fatty layer, preferably avoiding disrupting the muscle fascia 148 (FIG. 13A). Preferably, a surgeon blunt dissects a pocket 150 to the precise size of the analyte sensor 12 using the sizing tool 138 to confirm pocket size. Namely, the surgeon may use a tool or aid for visualization of the pocket during formation and incrementally dissects the pocket using the sizing tool 138 frequently to test the length and width of the pocket. As described in more detail above, it is believed that excess space in the pocket surrounding a sensor 12 provides an opportunity for mobilization and migration of the sensor, which results in wounding and build-up of the thickness of the foreign body capsule and may encourage barrier cell layer formation adjacent to the sensing region 16. It is noted that because analyte transport at the sensing region is critical for sensor performance, the implantation systems and methods are designed to aid the surgeon in forming a precise pocket with minimal tissue trauma.

In one preferred embodiment, the pocket is formed adjacent to the fascia 148 to provide a tough tissue for short term anchoring (for example, suturing). In one aspect of this preferred embodiment, two sutures (FIG. 13A) are placed on the fascia within the pocket directly under the incision, cranial and caudal to where the sensor 12 will be placed. These sutures are preferably placed in a location 152 on the fascia 148 parallel to and as close as possible to the location of the sensor insertion, optionally using the sizing tool to estimate proper suture placement. These sutures are preferably non-resorbable, however resorbable sutures may also be advantageous in some alternative embodiments. Suturing technique will be described in more detail with reference to FIG. 13A, below. Alternatively, other implantation and anchoring techniques are contemplated that may not benefit from suturing, or may not require suturing to a tough tissue.

In another preferred embodiment, the pocket is formed within the fatty tissue or other soft tissue of the host. These embodiments minimize invasive dissection as compared with the above-described embodiment. Namely, by forming the pocket in more shallow location of the host than the fascia, less dissection is required, which is believed to induce less tissue trauma. Additionally, it may be easier for the doctor or surgeon to visually confirm pocket formation (for example, sizing and location). It is noted that these embodiments may or may not include a short-term anchoring mechanism, such as described in more detail with reference to FIG. 10A.

Figure 12B:
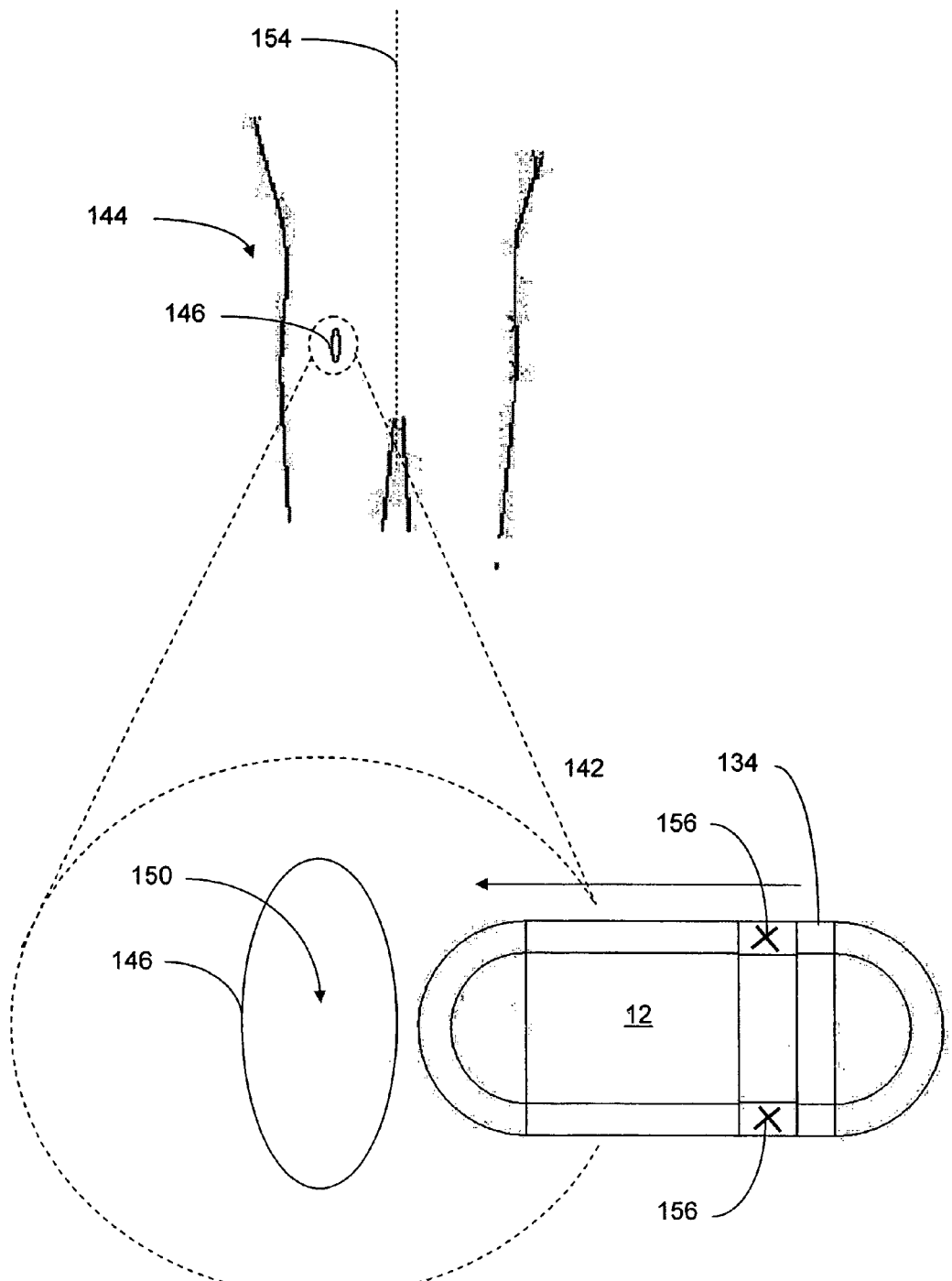
FIG. 12B is a perspective view of a portion of the abdominal region of a human, showing an exploded view of sensor insertion into the precisely formed pocket.

FIG. 12B is a perspective view of a portion of the abdominal region of a human, showing sensor insertion into the precisely formed pocket in one preferred embodiment. In this embodiment, the sensor 12 is placed in a lower plane of the subcutaneous fatty layer as close as possible to the muscle fascia 148 without disrupting the fascia. Additionally, the sensor 12 is placed with the long axis perpendicular to and slightly to one side of the midline 154 of the host. It is noted that in this embodiment, the sensing region 16 is located off-center and is placed within the patient with the sensing region facing the fascia 148 and more distal to the mid-line 154 than the suture strip 134. Thus, in the illustrated embodiment, the sensor 12 is inserted into the pocket so that approximately one-third of the sensor is facing medial to the incision 146 and the other approximately two-thirds is facing lateral to the incision 146. While not wishing to be bound by theory, it is believed that because there exists less connective tissue in this region lateral from the midline 154 than more proximal to the midline, the sensing region may experience less trauma associated with the connective tissue dissection. It is noted, however, that the incision may be centrally or otherwise located in alternative embodiments, which may advantageously simplify the implantation procedure, for example.

FIG. 13A is a schematic view of the sensor after insertion into the pocket with the sensing region positioned adjacent to the fascia. Short-term anchoring may be preferable in this embodiment, in order to immobilize the sensor within the pocket and adjacent to the fascia for providing optimal opportunity for healthy vascularized wound healing. However, alternative preferred embodiments may not include short-term anchoring and/or placement of the sensor adjacent to the fascia, which is described in more detail above.

In the embodiment of FIG. 13A, the sensor body 12 is sutured to the fascia 148 using the short-term anchoring component, namely the suture strip 134. Preferably, the suturing technique maintains the sensor body 12 in compression against the fascia 148 to ensure minimal movement of the sensing region 16 against the tissue 148. In one preferred method of suturing the sensor 12 to the fascia 148, the pre-positioned sutures, which are located on the fascia in a position 152 in line with each side of the suture strip, such as described with reference to FIGS. 12A and 12B, one of which is shown in the side view of FIG. 13A. Two additional sutures are sutured to the suture strip 134, on each side of the suture strip in a position 156 in line with the pre-positioned sutures 152. The sutures are then tied together, preferably tying diametrically opposed sutures to each other, for example the pre-positioned suture on one side with the suture-strip suture on the opposite side, and vice versa. In this way, the sutures and the sensor body are held in compression to ensure immobilization of the sensor 12 within the pocket 150. Alternative methods of suturing the sensor body to the fascia or other tough tissue are appreciated by one skilled in the art and are considered within the scope of the preferred embodiments.

After short-term anchoring is complete, the incision is closed; preferably ensuring the subcutaneous tissue is held snugly around the sensor with resorbable sutures, for example, to minimize vacant space adjacent to the sensor. The skin incision may be closed using standard wound closure techniques.

In one embodiment, the entire surface of the sensor is covered with an anchoring material to provide for strong attachment to the tissues. In another embodiment, only the sensor head side of the sensor incorporates anchoring material, with the other sides of the sensor lacking fibers or porous anchoring structures and instead presenting a very smooth, non-reactive biomaterial surface to prevent attachment to tissue and to support the formation of a thicker capsule. The anchoring material may be polyester, polypropylene cloth, polytetrafluoroethylene felts, expanded polytetrafluoroethylene, porous silicone, or the like.

FIG. 13B is a side view of an analyte sensor with long-term anchoring component in the form of an anchoring material 136 on both sides of the sensor, such as described in more detail with reference to FIG. 10. In this embodiment, the analyte sensor is implanted subcutaneously and is ingrown with fibrous, vascularized tissue after implantation.

In preferred embodiments, the sensor of the described geometry is implanted at the interface between two kinds of tissue, and is preferably anchored to the more robust tissue type. While the sensor geometries of preferred embodiments are particularly preferred for use at tissue interfaces, such sensors are also suitable for use when implanted into a single type of tissue, for example, muscle tissue or adipose tissue. In one alternative embodiment, the sensor may be suspended, with or without sutures, in a single tissue type, or be placed between two tissue types, and anchoring material covering substantially the entire surface of the device may be sufficient to prevent device migration, such as described elsewhere herein.

FIG. 13A illustrates the surface of the sensor 12 in mechanical contact with the overlying tissue 158, as well as the underlying muscle fascia 148, due to the ingrowth of the fibrous tissue and vasculature. In this embodiment, any surface of the sensor 12 covered with anchoring material 136 is typically ingrown with fibrous, vascularized tissue 160, which aids in anchoring the sensor and mitigating motion artifact. It may be noted however, that in some cases, forces applied laterally to this tissue may be translated to the sensor, and likewise to the fascia side of the sensor, causing potential disruption of the interface with the fascia. Therefore, although the radial profile of the side of the sensor incorporating the sensing region assists in preventing forces in the distal subcutaneous tissue from exerting forces on the sensor head side, which is attached to the muscle fascia by an anchoring material, complete coverage of the device with anchoring material may not be preferred in certain embodiments.

It may be noted that other factors of the preferred embodiments aid in immobilizing the sensor within the host, for example the sensor geometry, such as described in more detail with reference to FIG. 6. Additionally, the inventors have designed the sensor with a "low profile" to reduce the possibility of "fiddling" behavior that was seen in the above-described experiment. "Low profile" is loosely defined as an overall configuration, including dimensions, shape, and aspect ratio, that is deliberately inconspicuous when implanted.

Additionally, the preferred embodiments describe a relatively thin, rectangular or oval sensor wherein the sensing region is positioned on one of the large sides of the sensor (for example, rather than at the tip). When implanted, the sensor is preferably oriented such that the sensing region is adjacent to the muscle fascia underlying the subcutaneous space; however other locations are also possible.

Taken together, the preferred sensor substantially does not protrude through the host's skin (which may be somewhat dependent upon the host's body fat) and is less amenable to accidental bumping or movement, and less available for patient "fiddling." It is a thin, oblong shape, not cylindrical, so rotational forces are not as likely to affect the sensor-tissue interface. With the sensing region oriented down towards the fascia, and nearer to the center of the sensor, downward pressure on either end is not transferred as shear force to the sensing region.

In general, miniaturization of the sensor (for example, size and mass) prevents motion of the device and may reduce the time for sensor start-up by minimizing the disruption of the fragile new capillaries necessary to supply analytes (for example, oxygen and glucose) to the sensor. Miniaturization is also believed to reduce the vascular compression/postural effects that have been found to block the transport of oxygen when the host is positioned in such a way as to block proper transport of analytes to the sensing region, for example.

Methods and devices that are suitable for use in conjunction with aspects of the preferred embodiments are disclosed in copending U.S. patent application Ser. No. 10/789,359 filed Feb. 26, 2004 and entitled, "INTEGRATED DELIVERY DEVICE FOR CONTINUOUS GLUCOSE SENSOR"; U.S. application Ser. No. 10/685,636 filed Oct. 28, 2003 and entitled, "SILICONE COMPOSITION FOR BIOCOMPATIBLE MEMBRANE"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug.

22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE." The foregoing patent applications and patents are incorporated herein by reference in their entireties.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein, are hereby incorporated by reference in their entirety.

What is claimed is:

1. An electrochemical glucose sensor comprising a three-electrode system, the sensor comprising:
    an electrochemical cell comprising a working electrode, reference electrode, and counter electrode; and
    a potentiostat that controls the potential between the working and reference electrodes, wherein the potentiostat sets a low voltage limit at which the counter electrode of the glucose sensor reacts with reducible species, other than oxygen, when oxygen becomes limited and at which no substantial bubble formation occurs, wherein the potentiostat comprises an operational amplifier comprising:
    (i) a first input coupled to the reference electrode;
    (ii) a second input coupled to a reference voltage source; and
    (iii) an output coupled to the counter electrode, wherein the reference voltage source is set to a voltage value relative to battery ground such that the low voltage limit at the counter electrode causes the counter electrode to react with reducible species, other than oxygen, when oxygen becomes limited, and substantial bubble formation does not occur at the counter electrode.

2. The sensor of claim 1, wherein the reference voltage setting is between about +0.6V and +0.8V with respect to battery ground.

3. The sensor of claim 2, wherein the reference voltage setting is about +0.7V with respect to battery ground.

4. The sensor of claim 1, wherein the electrochemical cell is configured and arranged for transcutaneous implantation.

5. The sensor of claim 1, further comprising an RF module, wherein the RF module is operably connected to the potentiostat.

6. The sensor of claim 5, further comprising a receiver configured to receive RF transmissions from the RF module.

7. The sensor of claim 6, wherein the receiver comprises a display configured to display sensor data.

8. The sensor of claim 1, wherein the potentiostat comprises a second operational amplifier comprising:
    (i) a first input coupled to the working electrode;
    (ii) a second input coupled to a working voltage source; and
    (iii) an output coupled to the working electrode through a resistor, wherein the potential between the working and reference electrodes is determined by the potential of the working voltage source and reference voltage source.

9. An electrochemical glucose sensor comprising a three-electrode system, the sensor comprising:
    an electrochemical cell comprising a working electrode, reference electrode, and counter electrode; and
    a potentiostat that controls the potential between the working and reference electrodes, wherein the potentiostat comprises an operational amplifier comprising:
    (i) a first input coupled to the reference electrode;
    (ii) a second input coupled to a reference voltage source;
    (iii) an output coupled to the counter electrode;
    (iv) a negative power supply input coupled to a first voltage source; and
    (v) a positive power supply input coupled to a second voltage source, wherein the reference voltage source, first voltage source and second voltage source set a low voltage limit at which the counter electrode reacts with reducible species, other than oxygen, when oxygen becomes limited, and at which no substantial bubble formation occurs.

10. The sensor of claim 9, wherein the reference voltage setting is between about +0.6V and +0.8V with respect to battery ground.

11. The sensor of claim 9, wherein the reference voltage setting is about +0.7V with respect to battery ground.

12. The sensor of claim 9, wherein the negative power supply input is set to a voltage of battery ground.

13. The sensor of claim 9, wherein the potentiostat comprises a second operational amplifier comprising:
    (i) a first input coupled to the working electrode;
    (ii) a second input coupled to a working voltage source; and
    (iii) an output coupled to the working electrode though a resistor, wherein the potential between the working and reference electrodes is determined by the potential of the working voltage source and reference voltage source.

14. The sensor of claim 9, wherein the electrochemical cell is configured and arranged for transcutaneous implantation.

15. The sensor of claim 9, further comprising an RF module, wherein the RF module is operably connected to the potentiostat.

16. The sensor of claim 15, further comprising a receiver configured to receive RF transmissions from the RF module.

17. The sensor of claim 16, wherein the receiver comprises a display configured to display sensor data.

18. An electrochemical glucose sensor comprising a three-electrode system, the sensor comprising:
- an electrochemical cell comprising a working electrode, reference electrode, and counter electrode; and
- a potentiostat that controls the potential between the working and reference electrodes, wherein the potentiostat comprises a current limiter configured to limit the current through at least one of the counter or working electrodes preventing bubble formation from occurring and allow sufficient current through the counter electrode such that it reacts with reducible species, other than oxygen, when oxygen becomes limited.

19. The sensor of claim 18, wherein the electrochemical cell is configured and arranged for transcutaneous implantation.

20. The sensor of claim 18, further comprising an RF module, wherein the RF module is operably connected to the potentiostat.

21. The sensor of claim 20, further comprising a receiver configured to receive RF transmissions from the RF module.

22. The sensor of claim 21, wherein the receiver comprises a display configured to display sensor data.

23. An electrochemical glucose sensor comprising a three-electrode system, the sensor comprising:
- an electrochemical cell comprising a working electrode, reference electrode, and counter electrode; and
- a potentiostat that controls the potential between the working and reference electrodes, the potentiostat comprises an operational amplifier comprising:
  (i) a first input coupled to the reference electrode;
  (ii) a second input coupled to a reference voltage source;
  (iii) an output coupled to the counter electrode; and
  (vi) a voltage offset input coupled to an offset voltage source, wherein the offset voltage source sets a low voltage limit at which the counter electrode reacts with reducible species, other than oxygen, when oxygen becomes limited, and at which no substantial bubble formation occurs.

24. The sensor of claim 23, wherein the voltage applied to the voltage offset input is set to battery ground.

25. The sensor of claim 23, wherein the electrochemical cell is configured and arranged for transcutaneous implantation.

26. The sensor of claim 23, further comprising an RF module, wherein the RF module is operably connected to the potentiostat.

27. The sensor of claim 26, further comprising a receiver configured to receive RF transmissions from the RF module.

28. The sensor of claim 27, wherein the receiver comprises a display configured to display sensor data.

* * * * *

UNITED STATES PATENT AND TRADEMARK OFFICE
CERTIFICATE OF CORRECTION

PATENT NO.      : 7,657,297 B2
APPLICATION NO. : 10/838909
DATED           : February 2, 2010
INVENTOR(S)     : Simpson et al.

It is certified that error appears in the above-identified patent and that said Letters Patent is hereby corrected as shown below:

On the Title Page,

Item [*] Notice: Subject to any disclaimer, the term of this patent is extended or adjusted under 35 U.S.C. by 910 days.

Delete the phrase "by 910 days" and insert --by 1348 days--.

| Issued Patent | | 1. Description of Discrepancy |
|---|---|---|
| Column | Line | |
| (Item 56) Page 4 Col. 1 | 38 | Under Other Publications, change "Boll," to --Bott,--. |
| (Item 56) Page 4 Col. 2 | 35 | Under Other Publications, change "09/633,369." to --09/636,369.--. |
| (Item 56) Page 4 Col. 2 | 39 | Under Other Publications, change "datd" to --dated--. |
| 12 | 17 | Change "andrenostenedione;" to --androstenedione;--. |
| 12 | 31 | Change "diptheria/" to --diphtheria/--. |
| 12 | 38 | Change "perioxidase;" to --peroxidase;--. |
| 12 | 51-52 | Change "duodenalisa," to --duodenalis,--. |
| 12 | 59 | Change "Trepenoma pallidium," to --Treponema pallidum,--. |
| 12 | 60 | Change "stomatis" to --stomatitis--. |
| 13 | 14 | Change "(barbituates," to --(barbiturates,--. |

Signed and Sealed this

Twentieth Day of July, 2010

David J. Kappos
*Director of the United States Patent and Trademark Office*

CERTIFICATE OF CORRECTION (continued)
U.S. Pat. No. 7,657,297 B2

| | | |
|---|---|---|
| 41 | 54 | Change "intraperotoneal," to --intraperitoneal,--. |
| 48 | 9 | In Claim 23, change "(vi)" to --(iv)--. |